(12) United States Patent
Deml et al.

(10) Patent No.: US 9,733,246 B2
(45) Date of Patent: Aug. 15, 2017

(54) METHOD FOR DETECTION, DIFFERENTIATION AND QUANTIFICATION OF T CELL POPULATIONS BY WAY OF REVERSE TRANSCRIPTION QUANTITATIVE REAL TIME PCR (RT-QPCR) TECHNOLOGY

(75) Inventors: Ludwig Deml, Regenstauf (DE);
Kristina Naumann, Amberg (DE);
Kornelia Schlombs, Regensburg (DE);
Sascha Barabas, Bad Abbach (DE)

(73) Assignee: LOPHIUS BIOSCIENCES GMBH, Regensburg (DE)

( * ) Notice: Subject to any disclaimer, the term of this patent is extended or adjusted under 35 U.S.C. 154(b) by 124 days.

(21) Appl. No.: 13/821,537

(22) PCT Filed: Sep. 16, 2011

(86) PCT No.: PCT/DE2011/075225
§ 371 (c)(1),
(2), (4) Date: Jun. 28, 2013

(87) PCT Pub. No.: WO2012/037937
PCT Pub. Date: Mar. 29, 2012

(65) Prior Publication Data
US 2013/0288229 A1    Oct. 31, 2013

(30) Foreign Application Priority Data
Sep. 17, 2010 (DE) .................. 10 2010 037 622

(51) Int. Cl.
*C12P 19/34* (2006.01)
*G01N 33/569* (2006.01)
*C12Q 1/68* (2006.01)

(52) U.S. Cl.
CPC ..... *G01N 33/56972* (2013.01); *C12Q 1/6876* (2013.01); *C12Q 2600/158* (2013.01); *C12Q 2600/16* (2013.01)

(58) Field of Classification Search
CPC ............ C12Q 1/6876; C12Q 2600/158; C12Q 2600/16; G01N 33/56972
USPC ...................................................... 435/91.2
See application file for complete search history.

(56) References Cited

U.S. PATENT DOCUMENTS

| 7,659,058 | B2 * | 2/2010 | Deml ............... | C07K 14/70532 |
| | | | | 435/372 |
| 8,064,240 | B2 | 11/2011 | Takashima | |
| 2002/0193296 | A1 | 12/2002 | Xu et al. | |
| 2005/0112576 | A1 | 5/2005 | Deml | |
| 2009/0275067 | A1 | 11/2009 | Taniguchi | |
| 2009/0317798 | A1 * | 12/2009 | Heid ..................... | B01L 3/5027 |
| | | | | 435/6.12 |
| 2012/0004124 | A1 * | 1/2012 | Schultze et al. ................... | 506/9 |

FOREIGN PATENT DOCUMENTS

| EP | 1 448 781 | 8/2004 |
| JP | 2003-202338 | 7/2003 |
| JP | 2005-524412 | 8/2005 |
| JP | 2008-500052 | 1/2008 |
| JP | 2009-195142 | 9/2009 |
| JP | 2010-514791 | 5/2010 |
| WO | WO 95/08115 | 3/1995 |
| WO | WO 00/57705 | 10/2000 |
| WO | WO 03/012061 | 2/2003 |
| WO | WO 03/095668 | 11/2003 |
| WO | WO 2005/118788 | 12/2005 |
| WO | WO 2008/083174 | 7/2008 |
| WO | WO 2008/104184 | 9/2008 |
| WO | WO 2008/121420 | 10/2008 |
| WO | WO 2009/120891 | 10/2009 |
| WO | WO 2010/027094 | 3/2010 |
| WO | WO 2011084333 | * 7/2011 |

OTHER PUBLICATIONS

Habib-Agahi, et al., "Co-stimulation with 4-1BB ligands allows extended T-cell proliferation, synergizes with CD80/CD86 and can reactivate anergic T cells", *International Immunology*, 19(12):1383-1394, 2007.
PCT International Preliminary Report on Patentability issued in International Application No. PCT/DE2011/075225, issued Mar. 19, 2011.
PCT International Search Report and Written Opinion issued in International Application No. PCT/DE2011/075225, issued Apr. 26, 2012.
Rissoan, et al., "Reciprocal control of T helper cell and dendritic cell differentiation", *Science*, 283(5405):1183-1186, 1999.
Wen, et al., "4-1BB ligand-mediated costimulation of human T cells induces CD4 and CD8 T cell expansion, cytokine production, and the development of cytolytic effector function", *The Journal of Immunology*, 168(10):4897-4906, 2002.

* cited by examiner

*Primary Examiner* — Cynthia B Wilder
(74) *Attorney, Agent, or Firm* — Parker Highlander PLLC

(57) ABSTRACT

The present invention relates to a method for detection, differentiation and quantification of T cell populations, comprising the following steps a) contacting a first aliquot of a body fluid of an individual with at least one antigen, wherein the body fluid contains antigen presenting cells (APC) and T cells, b) incubating the first aliquot with at least one antigen for a certain period of time, c) detection and differentiation of the T cell population by detecting in the first aliquot and in a second aliquot of the body fluid of the individual, which has not been incubated with the at least one antigen, at least a first marker of the APC induced by T cells in a specific T cell population using reverse transcription quantitative real time-time polymerase chain reaction (RT-qPCR), and d) detection and quantification of the T cell population by determining the ratio of the detected marker of the APC of the first aliquot to the second aliquot as well as a kit for performing the method.

18 Claims, 24 Drawing Sheets

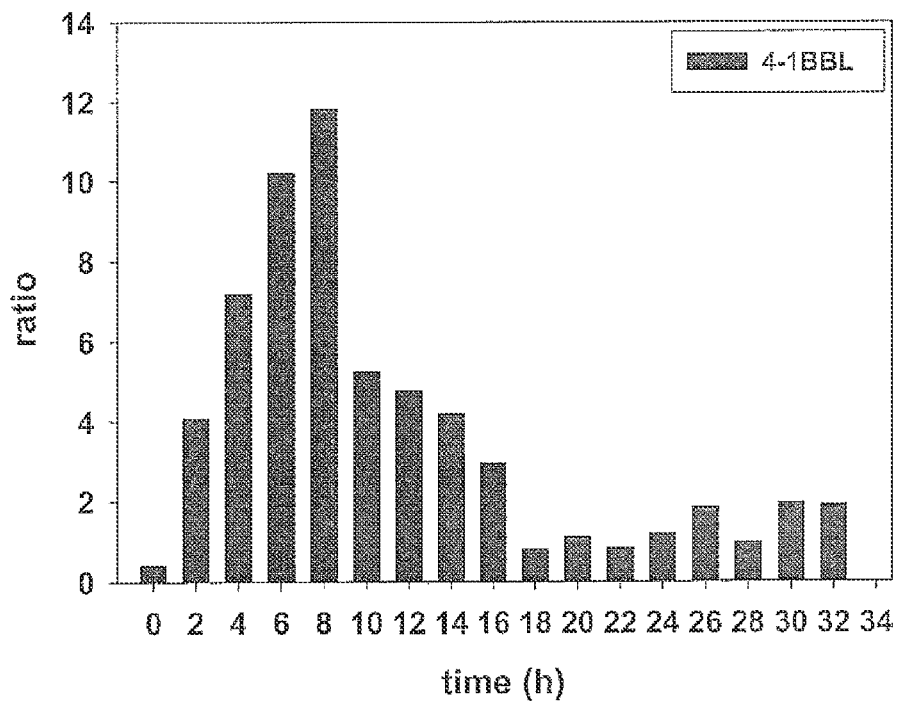
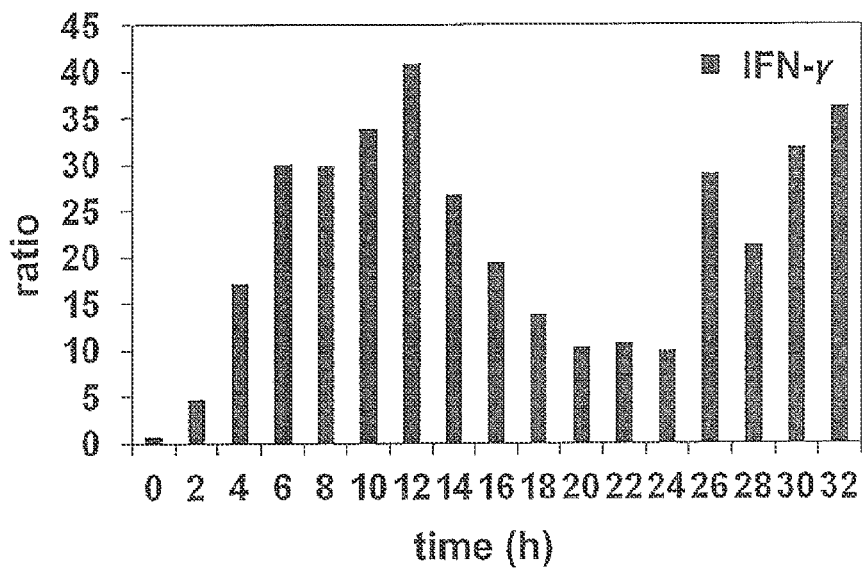

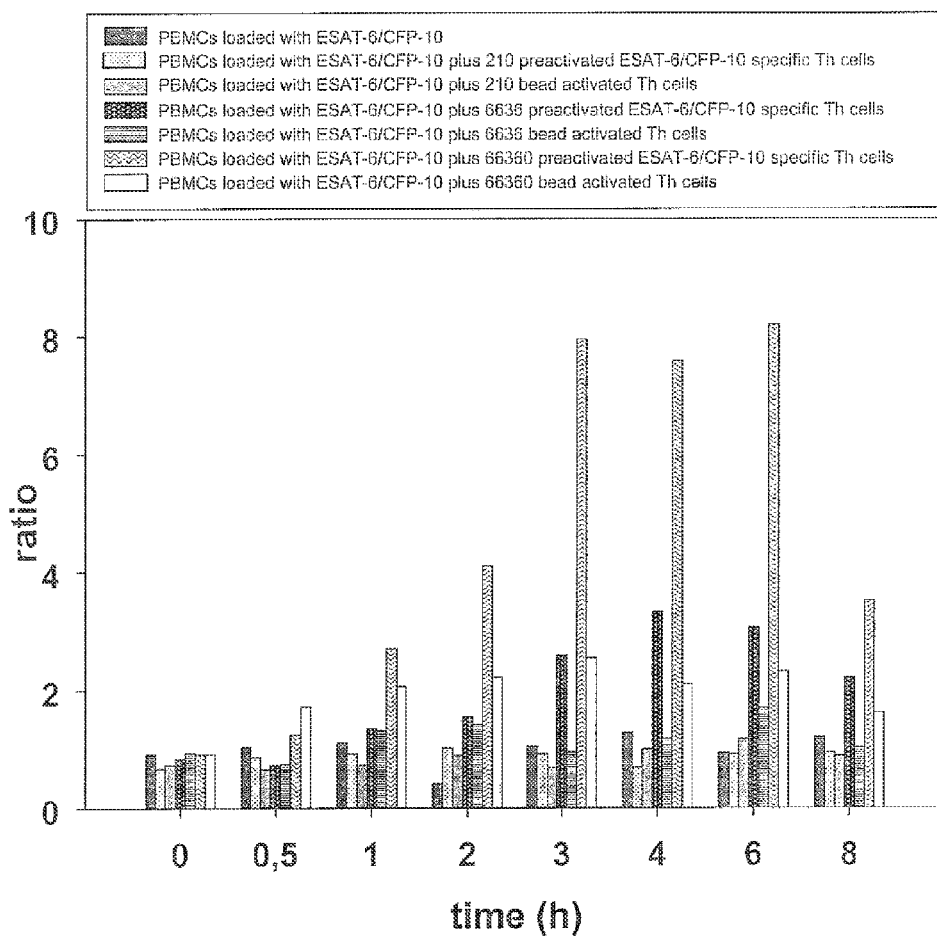

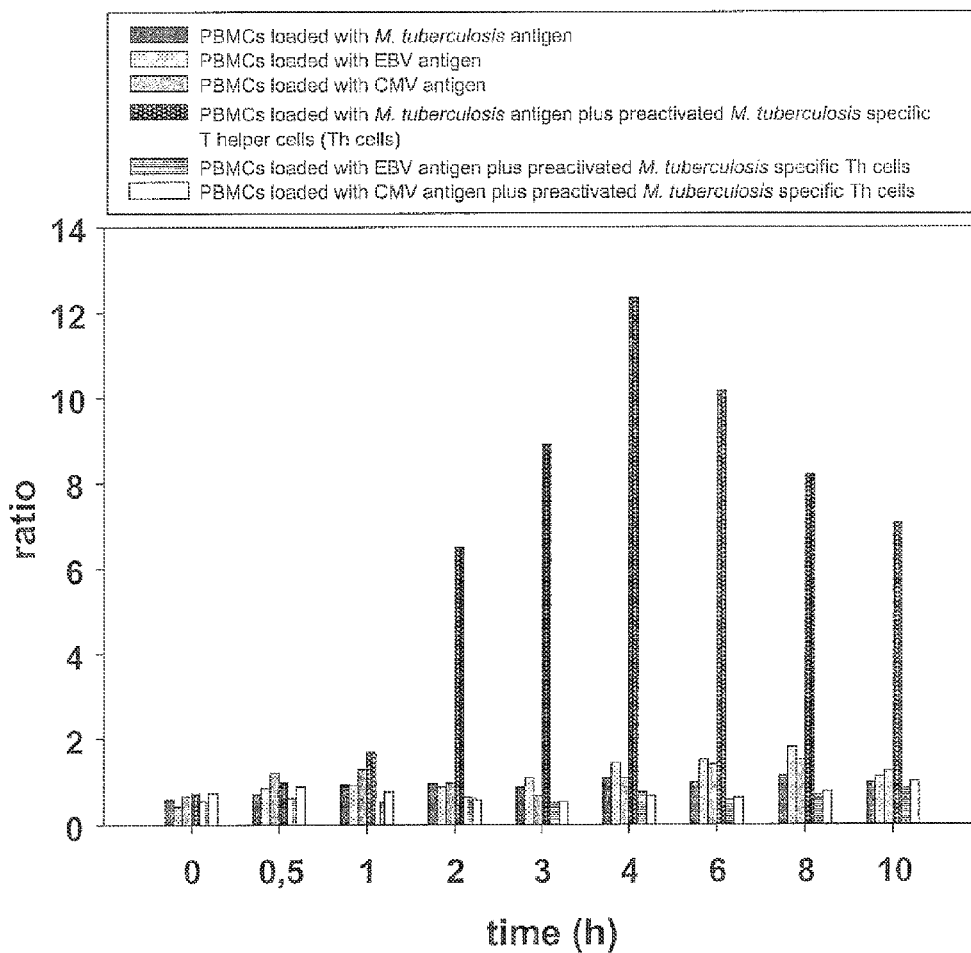

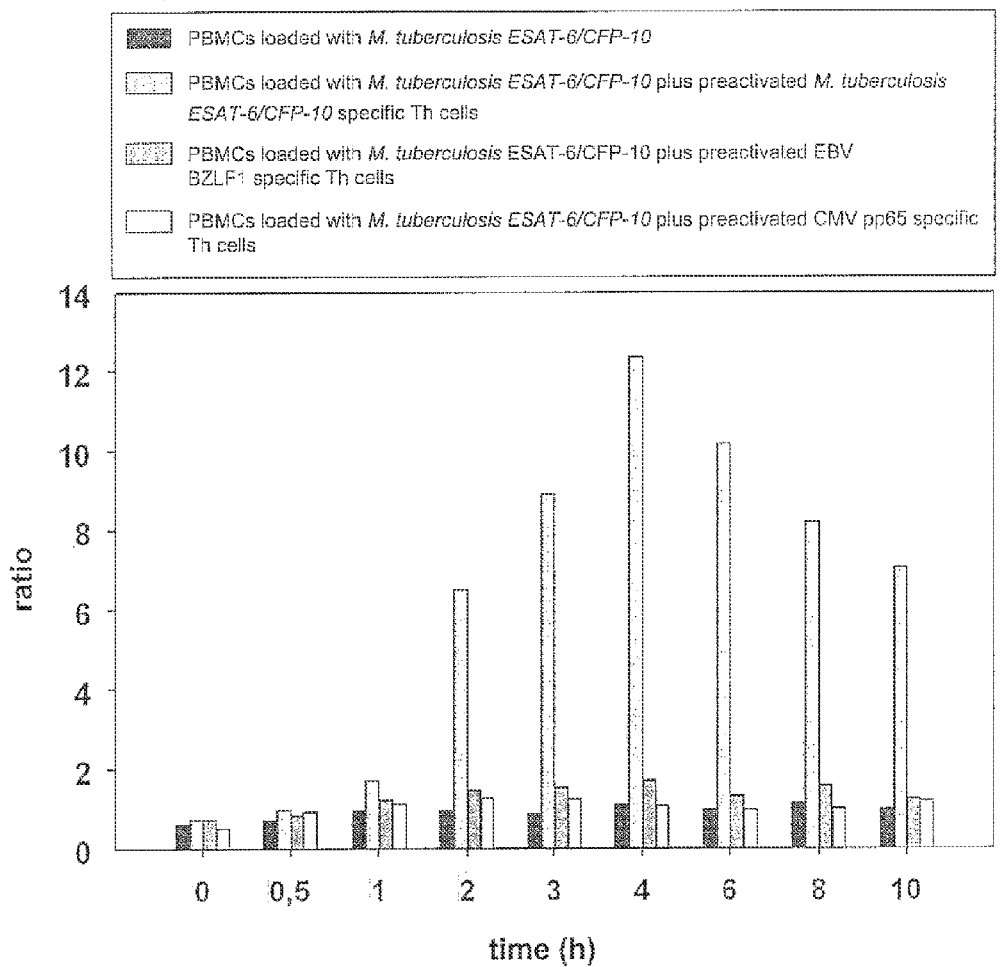

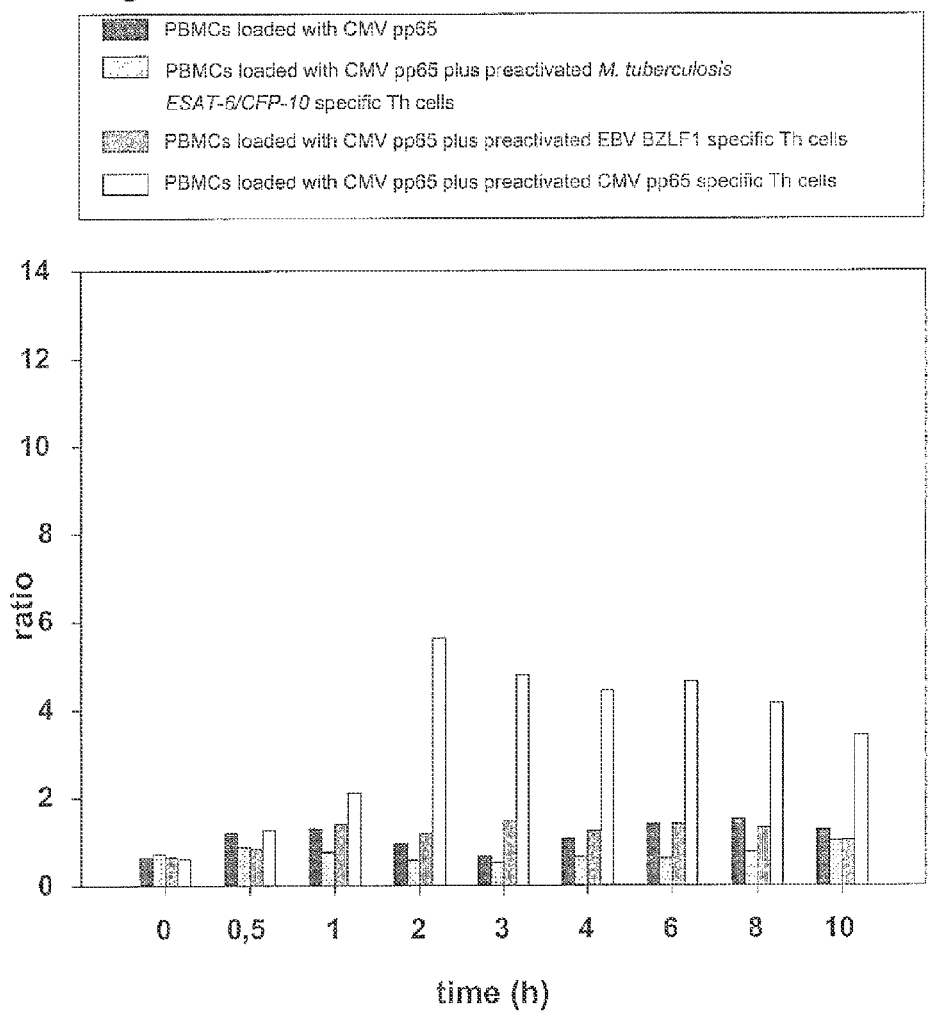

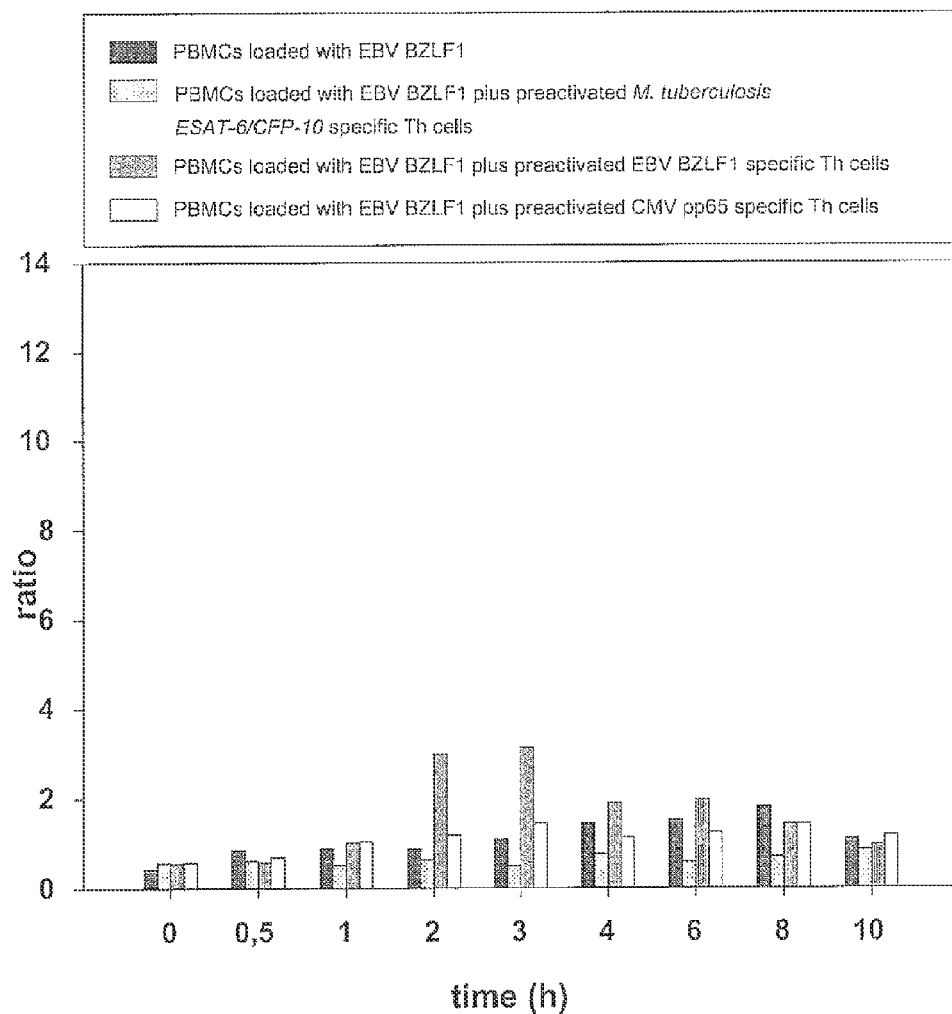

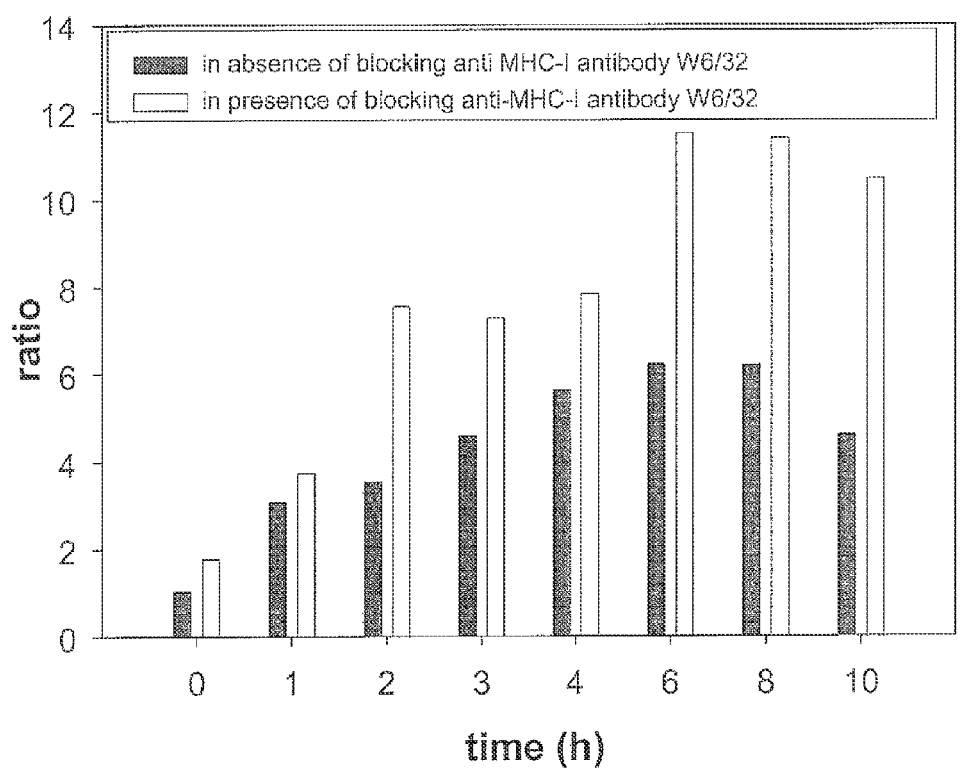

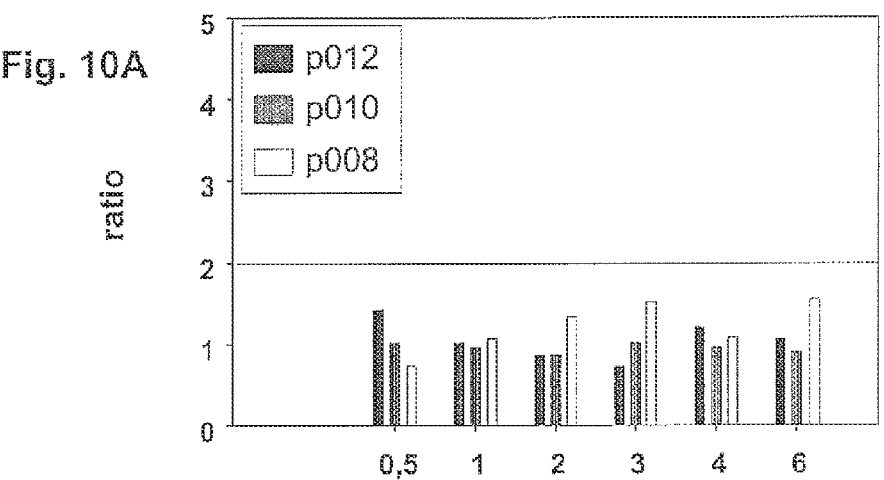
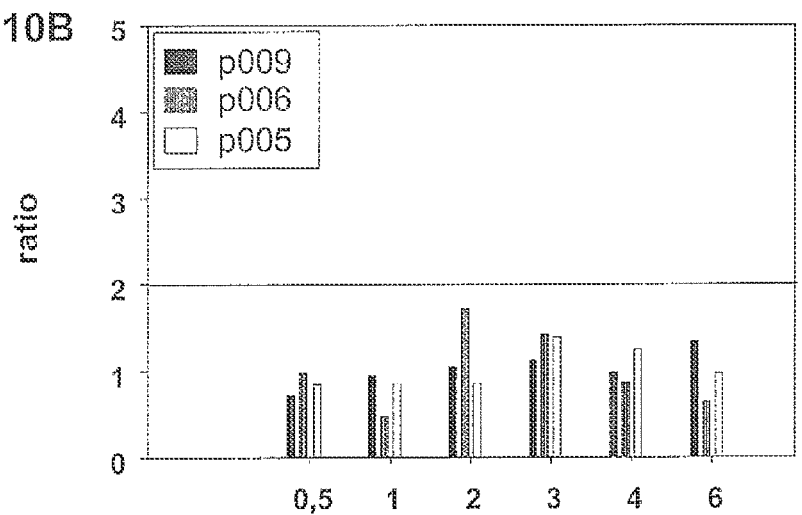
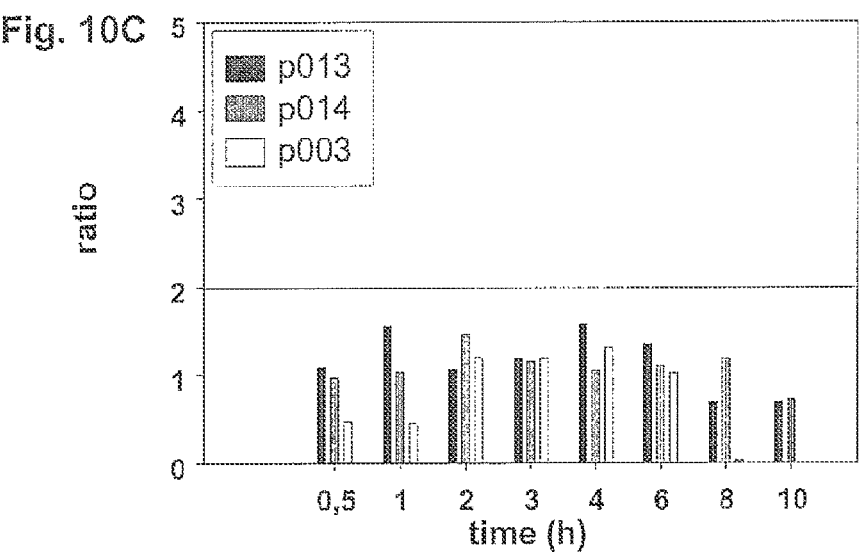

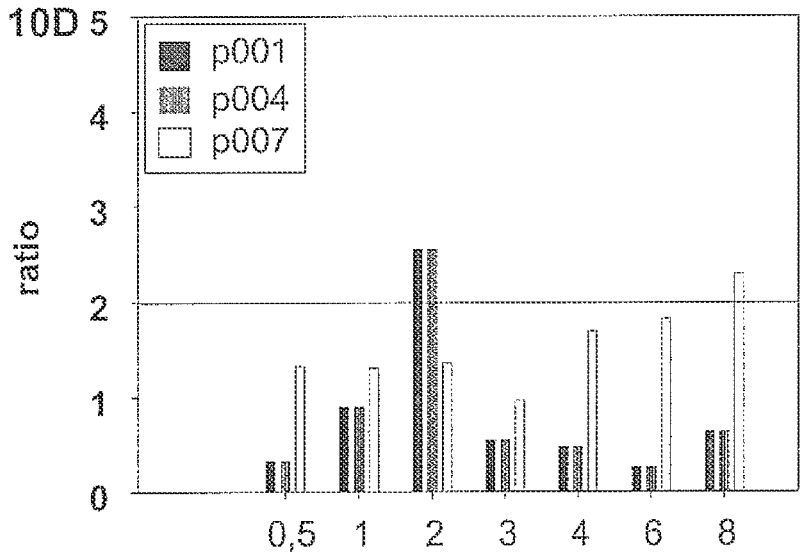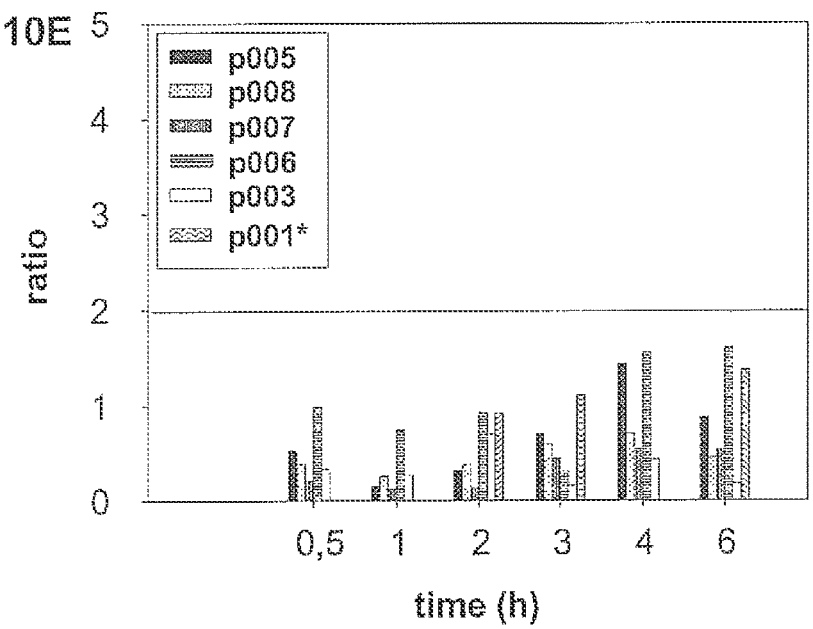

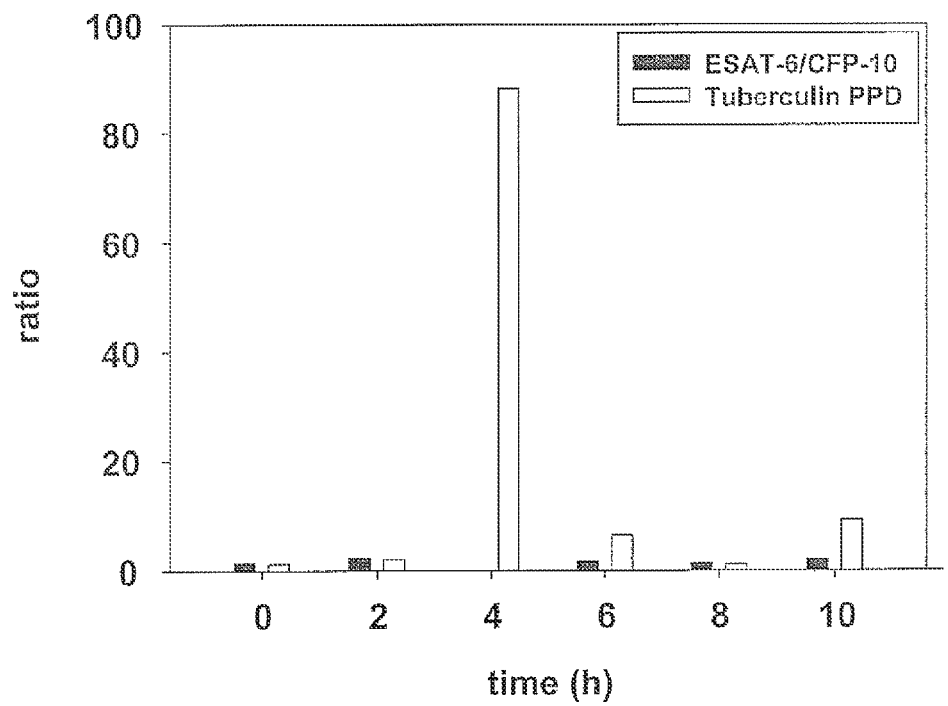
Fig. 11A
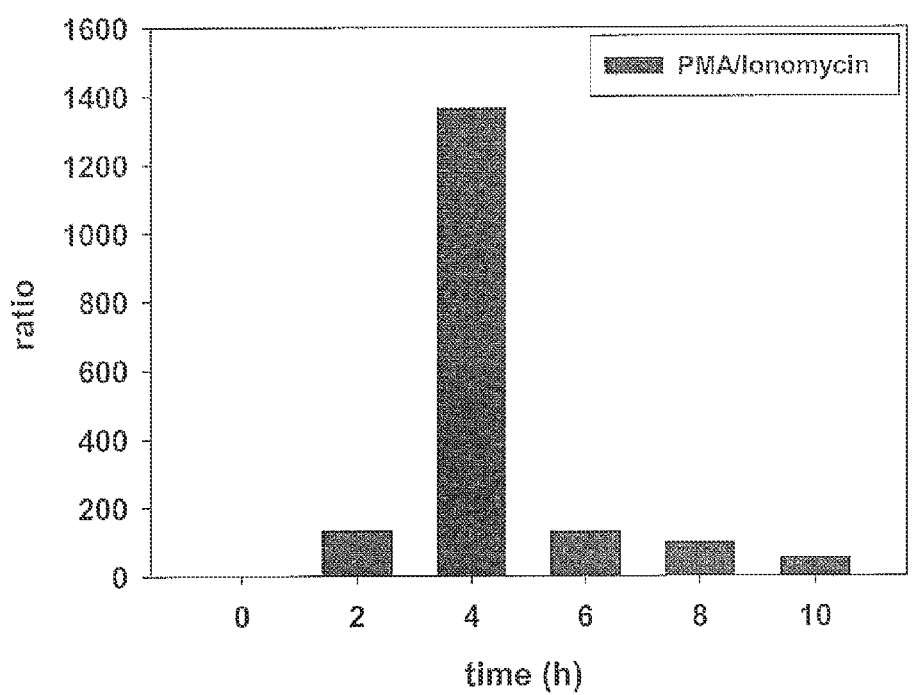

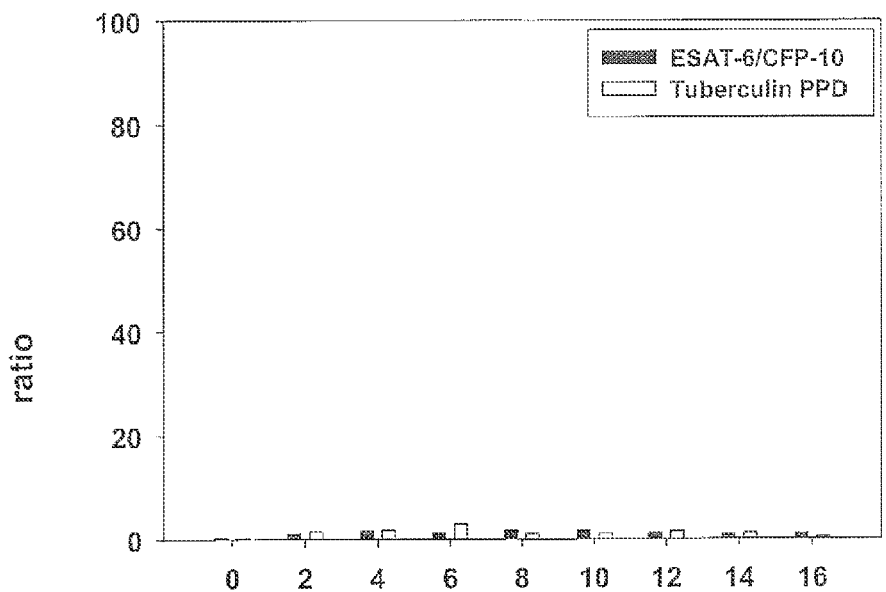
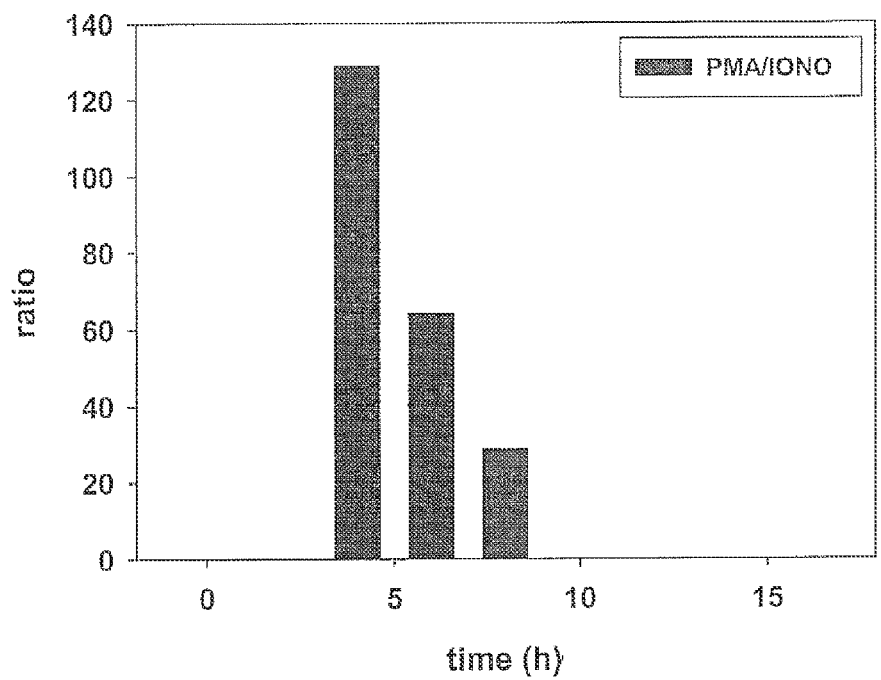
Figure 11B

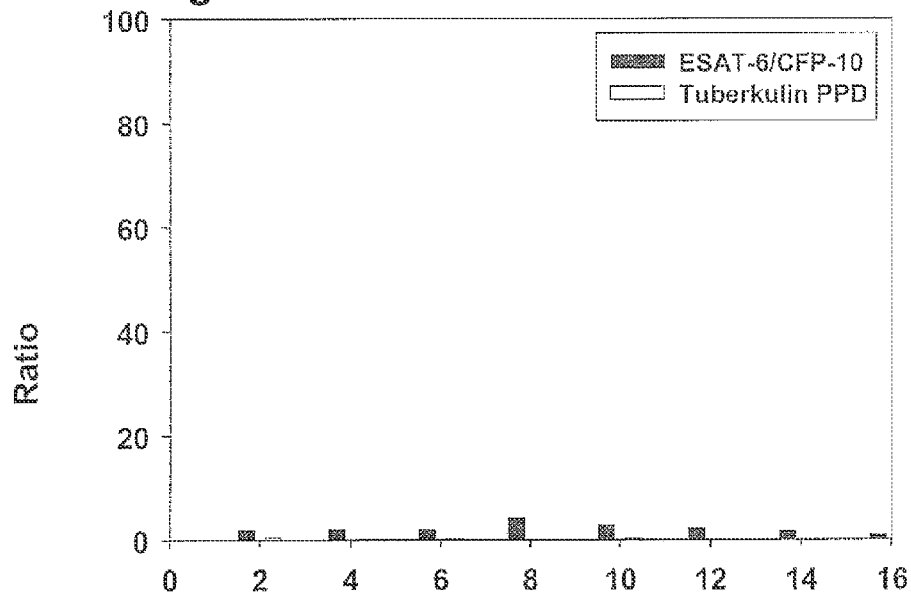
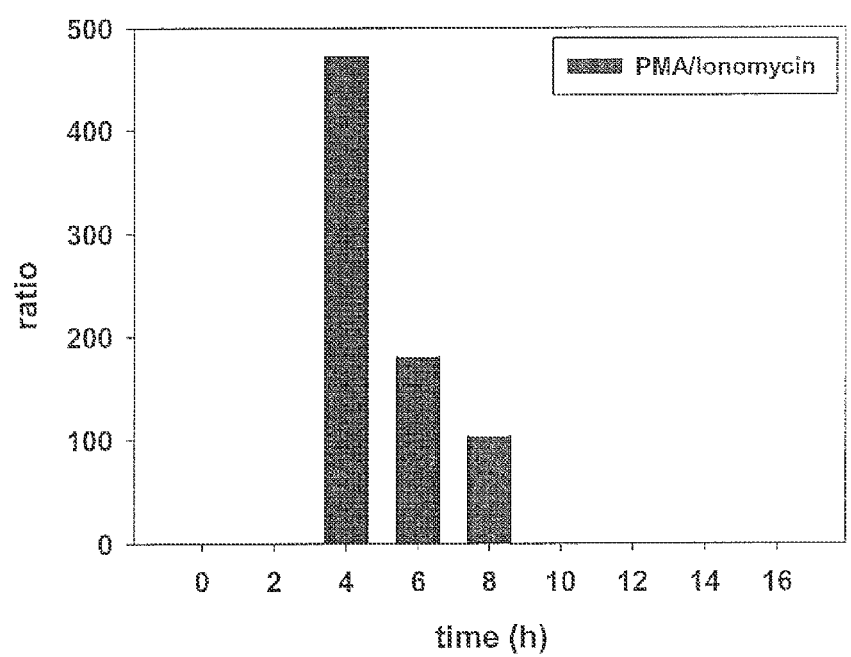
Figur 11 C

METHOD FOR DETECTION, DIFFERENTIATION AND QUANTIFICATION OF T CELL POPULATIONS BY WAY OF REVERSE TRANSCRIPTION QUANTITATIVE REAL TIME PCR (RT-QPCR) TECHNOLOGY

This application is a national phase application under 35 U.S.C. §371 of International Application No. PCT/DE2011/075225, filed Sep. 16, 2011, which claims priority to German Application No. DE 10 2010 037 622.1, filed Sep. 17, 2010. The entire text of each of the above referenced disclosures is specifically incorporated herein by reference.

BACKGROUND OF THE INVENTION

A. Field of the Invention

The present invention relates to methods for detection, differentiation and quantification of T cell populations, comprising the following steps a) contacting a first aliquot of a body fluid of an individual with at least one antigen, wherein the body fluid contains antigen presenting cells (APC) and T cells, b) incubating the first aliquot with the at least one antigen for a definite period of time, c) detection and differentiation of the T cell populations by detecting at least a first marker of the APCs induced by the T cells of a specific T cell population in the first aliquot and in a second aliquot of the body fluid of the individual, which has not been incubated with the at least one antigen, by way of reverse transcription quantitative real time polymerase chain reaction (RT-qPCR), and d) detection and quantification of the T cell populations by determining the ratio of the detected marker of the APCs in the first aliquot to the second aliquot, as well as a kit for performing the method.

B. Related Art

T cells play a key role in the complex network of immune defence against microbial infections and tumour diseases by coordinating the immune response and by controlling and eliminating pathogens as well as tumour cells through manifold direct and indirect effector functions. Interference with the complex T cell function may lead to an erroneous activation of autoaggressive T cells and concomitantly elicit severe autoimmune diseases such as multiple sclerosis (MS), rheumatoid arthritis (RA) and juvenile diabetes (type I diabetes).

In principle T cells exhibit phenotypically a large heterogeneity as well as a broad spectrum of effector functions. Thus, T cells may be roughly classified on basis of the expression of the surface proteins CD4 and CD8 as CD4 positive T cells (T helper cells (Th)) and CD8 positive cytotoxic T cells (CTL).

$CD4^+$ T cells play a key role in the activation, polarisation and coordination of the immune defence. $CD4^+$ T cells are activated due to a specific interaction of their T cell receptor with peptide loaded MHC class II molecules located on the surface of antigen presenting cells (APC) and govern subsequently via cell cell contact and/or secretion of various messenger molecules (for instance cytokines, chemokines) the production of antibodies by B cells (humoral branch of the immune response) and the activation of CTL (cellular branch of the immune response).

$CD4^+$ T cells can be subdivided on basis of the expression of characteristic surface proteins and the production of marker cytokines into T helper 1 (Th-1), T helper 2 (Th-2) and T helper 17 (Th17) cells. Th-1 cells are characterized by the production of the cytokines IFN-γ and TNF-α as well as the expression of the transcription factor T-bet. Th-1 cells support the mounting of an efficient cell-mediated immune response by stimulating the activation and differentiation of macrophages, $CD4^-CD8^+$ cytotoxic T cells, $CD4^+CD8^+$ cytotoxic T cells as well as of natural killer cells (NK cells) and NKT cells. Th-2 cells are characterized by the secretion of the cytokines IL-4, IL-5, IL-6, IL-10 and IL-13 as well as the production of the transcription factor GATA-3 and support the production as well as the class change of antibodies (humoral branch of the immune system) in B cells. Th-17 cells are characterized by the production of the cytokines IL-17, TNF-α, GM-CSF and IL-6 and seem to play an important role in rheumatologic autoimmune diseases. With regulatory T cells a further $CD4^+$ T cell population aside of Th-1, Th-2 and Th-17 cells was defined, which plays a significant role in the attenuation of immune responses, oral tolerance as well as in the prevention of autoimmune diseases. Regulatory T cells may be subdivided into $CD4^+$ $CD25^+$ $CTLA4^+$ natural regulatory T cells (Treg) as well as into Th-3 and Tr-1 cells, which are characterized by the production of the cytokines TGF-β (Th-3 cells) or IL-10 (Tr-1 cells).

CTL play a central role in combating cells and tissues infected with microorganisms and parasites as well as tumour cells by destroying them via direct effector mechanisms such as the release of cytotoxic substances (e.g. perforin, granzym) and triggering of apoptosis. In addition, by secreting immune stimulatory cytokines (IFN-γ, TNF-α, IL-15) and chemokines (MIP1α, MIP1β, Rantes) as well as various soluble antiviral factors (IFN-α, IFN-β, IFN-δ, CAF) CTLs exhibit further, to some extent very specific effector functions, which contribute very efficiently to restriction of pathogen replication and spreading. Furthermore, additional populations of cytotoxic T cells have been described, which exhibit a $CD4^+CD8^+$ phenotype ($CD4^+CD8^{dim}$, $CD4^{dim}CD8^{bright}$ or $CD4^{hi}CD8^{hi}$).

Thus, T cells represent an important protective mechanism of the acquired immune system for prevention and control of microbial- and in particular of virus-induced diseases as well as for the recognition and destruction of tumour cells.

The activation, polarization and regulation of specific T cells is governed by a strict control via APCs and is essentially defined by the subtype and maturation level of the APCs, by the mechanism of antigen uptake and presentation as well as by the intrinsic properties of the respective immunogen. Hereby the dose and localisation of a immunogen as well as the concentration of the immunomodulatory substances determine, whether a Th-1-, a Th-2- or a Th-17-mediated immune response develops or whether a tolerance is induced.

Professional APCs, such as dendritic cells (DC), monocytes and macrophages, but also B cells take a key position at the juncture between native and acquired immune system by specifically recognizing pathogens and tumour cells, taking these up and presenting fragments thereof together with MHC molecules of class I and class II to T cells. In addition fibroblasts of the skin, epithelial cells of the thymus and the thyroid gland, glial cells, beta cells of the pancreas as well as vascular endothelial cells may act as non-professional APC. Furthermore, current studies show that T cells may also act as APC. These APC T cells are created by the intercellular transfer of MHC class I and class II molecules as well as of costimulatory molecules, such as CD80, CD40 ligand (CD40L), OX40 ligand (OX40L) and 4-1BB ligand (4-1BBL, TNFSF9) due to contact with an APC, in particular a DC (Sokke Umeshappa et al. (2009), J. Virol. 182: 193-206).

For a successful stimulation of T cells by APCs three independent signals are required: the specific recognition of peptide loaded MHC molecules via the T cell receptor (TCR) (signal 1), the interaction of APC and T cell based costimulatory molecules with their ligands (signal 2), as well as the presence of T cell polarising cytokines, such as IFN-γ, IL-12, IL-4, IL-6 and TGF-β (signal 3).

Extracellular soluble proteins are usually degraded via the exogenic antigen processing pathway and the resulting peptides are presented complexed with MHC-II molecules on the surface of APCs. Peptides complexed with MHC class II molecules are recognized by $CD4^+$ T cells (T helper cells).

In contrast, degradation of cytosolic proteins occurs via the endogenous processing pathway, leading to presentation of the generated epitopes on MHC class 1 molecules. These peptide/MHC-I complexes are transported to the surface of APCs, where they are presented to cytotoxic T cells (CTL). Although the majority of epitopes presented on MHC class 1 molecules is derived from endogenous proteins and the majority of peptides complexed with MHC-II molecules is derived from exogenous proteins, this distinction is not absolute. For instance, various exogenously existing immunogens, such as particulate structures, various virus particles, immune complexes and lipoproteins end up via a mechanism called cross presentation on the endogenous processing pathway for antigen presentation on MHC I molecules.

For specific activation of naïve T cells is—aside of recognition of MHC molecules loaded with peptides (signal 1)—a second, costimulatory signal required (signal 2). This is triggered by interaction of various APC and T cell based costimulatory ligands with their receptors. Members of the TNF/TNF-receptor super family as well as of the immunoglobulin super family belong to the most important representatives of costimulatory molecules. In absence of the costimulatory signal the T cell becomes anergic. Anergy is the condition in which T cells do not propagate and do not react to an antigen.

The expression of costimulatory signal on APCs is essentially governed via exogenous stimuli, such as components of pathogens or traumatized tissues, as well as by cytokines. The activation and maturation of APCs results in an increased expression of pro-inflammatory and T cell polarising cytokines as well as of costimulatory molecules (CD80, CD86 and CD40), thereby drastically increasing the capability of APCs to activate cell mediated immune reactions. The specific antigen recognition by the TCR and the interaction with costimulatory molecules induces a targeted activation and proliferation of pathogen and disease specific naive T cells. This is accompanied by an increased secretion of IL-2 and the expression of CD40 ligand, which play an important role in the subsequent activation and expansion of other subpopulations of specific T cells. The polarisation of activated T cells in Th-1 or Th-2 effector cells occurs in dependence of the maturation level of the APCs, of the prevalent cytokine milieu as well as of the intrinsic properties and dose of the respective antigen.

The mounting of a specific T cell response in the course of an acute microbial infection usually occurs in three steps: during the effector phase antigen specific naive T cells are activated by contact with APCs loaded with antigen, which leads to a dramatic expansion of the specific T cells, the development of effector functions and the infiltration of activated effector T cells at the site of infection. This effector phase usually extends over a period of 1 to 2 weeks until elimination of the pathogen. In the subsequent contraction phase, which lasts several weeks, over 90% of the produced effector T cells die. Only a few antigen specific T cells survive and differentiate into long lasting memory T cells. In the memory phase these memory T cells persists in relatively stable cell numbers over many years in the body. These memory T cells can quickly be reactivated after a new contact with their antigen and exert their effector functions.

To avoid undesired immune reactions against the bodies own proteins and tissues autoreactive T cells are early on eliminated or inactivated by clonal deletion (anergy). The consequence is an antigen specific tolerance against the bodies own structures, such as proteins, cells, tissues and organs. In autoimmune diseases these protective mechanisms are inhibited or are only insufficiently developed. There is a number of hints that the autoimmune diseases are acquired via an innate "susceptibility", (genetic disposition), in combination with environmental influences such as microbial infections, pregnancy or due to the similarity of the body's own structures with pathogen and foreign tissue specific polypeptides, the so called molecular mimicry.

Besides, activated T cells play also a central role in the formation of chronic virus infections and the rejection of transplanted tissues and organs.

The determination of the phenotype, the frequency, the specificity, the functionality, the activation status of T cells represents an efficient strategy to gain information about the present course of disease or about diseases already overcome. Furthermore, such methods are of major importance for monitoring (monitoring) specific T cell responses in therapeutic and prophylactic vaccinations, as well as in the diagnostic detection of the number and functionality of T cells in chronic inflammations, autoimmune diseases and in transplant rejection.

In the past decades different technologies for detection of T cells have been developed, which may be roughly divided into two categories. The first group of methods relies on the direct identification and quantification of polypeptides specific T cells by using peptide-MHC multimeres, such as tetramers (Beckman Coulter), pentameres (Proimmune) and streptameres (IBA). This method allows the determination of epitope specific T cells with known MHC restriction. An analysis of the functionality of the T cells is not possible with this method. The most important limitation in using peptide MHC multimeres for the routine monitoring of disease or pathogen specific T cells ensue because the MHC/peptide multimeres are epitope as well as HLA specific. Thus, an exhaustive monitoring of pathogen as well as disease specific T cells in subjects with different HLA constellation requires the use of a broad spectrum of different peptide/MHC multimeres, which brings about high costs. In addition, these peptide/MHC multimeres are so far only available for a limited spectrum of MHC molecules.

A further method for determining specific T cells relies on the use of HLA molecules loaded with peptides, which are linked to green fluorescent protein (GFP). The epitope specific recognition and binding of these complexes by the T cell receptor leads to an internalisation of the GFP labelled peptide, whereby the respective CTL is visualized (Tomaru et al. (2003), Nat. Med. 9:469).

In contrast, the "functional" methods for monitoring specific T cells rely on the ex vivo stimulation of T cell and APC containing patient material with stimulator antigens and the subsequent detection of maturation processes, such as proliferation, production of marker cytokines, in specific reactivated T cells by way of various detection systems. The detection of specific $CD4^+$ T cells is accomplished here usually by stimulation of APC and T cell containing patient samples, such as heparinized whole blood or isolated peripheral mononuclear cells of the blood (PBMC) with proteins, polypeptides or peptides of a length of 15 to 25 amino acids and the detection of the specific T cell activation by determining the production of characteristic marker cytokines or the T cell proliferation. The cytokine detection is done for example with flow cytometry methods, such as intracellular cytokine staining and the cytokine secretion assay as well as with the ELISpot or ELISA technique. The determination of the T cell proliferation may for example be determined by bromodeoxyuridine (BrdU)- or carboxylfluorescein diacetate succinimidyl ester (CSFE) proliferation assays.

In contrast, the detection of specific $CD8^+$ T cells (CTL) is usually done by stimulating APC and T cell containing patient samples with short peptides of a length of 8 to 16 amino acids. Furthermore, CTLs may be detected specifically by infection with recombinant viruses or bacteria, which express the target structures of T cells intracellularly in APCs and the subsequent determination of the marker cytokines produced by the antigen specific T cells, usually IFN-$\gamma$ by way of flow cytometry methods, such as intracellular cytokine staining or by using the ELISpot or ELISA technology, respectively. In the alternative the specific detection of CTL may be done by means of $^{51}$chromium release assays or by using adequate non-radioactive methods, such as the lactate dehydrogenase cytotoxicity assay (for example from Clontech).

These available technologies allow the determination of disease and pathogen specific $CD4^+$ or $CD8^+$ memory T cells, but are not suitable or only very limited suitable for detection of activated T helper cells, which occur only transiently during the active course of disease.

$CD4^+$ T cells are transiently activated during active microbial infections and disease progression. Transient activation implies here that the T cells are only present for a defined, rather short period of time. Thus, activated T helper cells represent an important object for the detection of an active disease incident. A detection assay, which is as significant as possible, is required to determine activated T cells in the context of diagnosis of an active infectious diseases and auto-immune diseases accurately.

However, for certain applications in which discrimination between activated and non-activated T cells is required, such as in the detection of activated T cells during acute microbial infections and reactivations or the detection of activated autoaggressive T cells in the case of suspected multiple sclerosis or type 1 diabetes, are methods which are based on in vitro restimulation of memory T cells not or only very limited employable.

The methods hitherto available for detection of activated $CD4^+$ T cells exhibit so far only a low sensitivity and are thus disadvantageous. The reason for this low sensitivity is inter alia due to the fact that the pathogen or disease specific activated $CD4^+$ T cells are directly detected and are typically present only in small amounts in the patient material. However, this small number of available specific activated T cells hampers reliable and unambiguous detection which also satisfies diagnostic requirements, since the detection limit of these methods available hitherto is frequently undercut.

Thus, the methods available so far for the detection of antigen specific activated T helper cells usually rely for example on the flow cytometry determination of proteins which are transiently expressed on the surface of activated T cells. To these belong in particular the CD40 ligand and the CD25 protein. However, CD40 ligand is hardly detectable by flow cytometry, because the binding of antibodies leads to an internalisation of the CD40 ligand. In contrast, the CD25 protein may not only be found on activated T-helper cells but also on regulatory T cells and is thus not suitable for a reliable distinction between these two subpopulations of T helper cells. In addition, the enhanced expression of HLA-DR and CD69 as well as a reduced expression of CD27 represent further marker for activated T cells. The detection of activated antigen specific T cells requires here a parallel marker detection for determining the specificity, e.g. by using specific tetra-, penta- or streptamers, the phenotype, e.g. by determining characteristic surface markers, and/or the T cell activation, for instance via the production of marker cytokines, after a specific restimulation. A further disadvantage of the methods hitherto known is, that the reliable detection of some marker proteins by way of ELISA, ELISpot or FACS technology is impossible due to the membrane localisation of the marker proteins, the presence of preformed marker proteins in intracellular vesicles, and the high unspecific reactivity of the available antibodies with cellular proteins.

Thus, there exists a need for a method, which allows to detect, to differentiate and to quantify specific T cell populations, which are activated by bacterial, viral, parasitic or autoantigens, thereby enabling the assignment of these T cell populations to specific diseases and disease stages.

SUMMARY OF THE INVENTION

The problem to be solved by the present invention was thus to provide a method which allows a qualitative and sensitive as well as quantitative detection of pathogen or disease specific T cells of specific T cell populations.

A further problem to be solved by the present invention was to provide a method, which allows the distinction between specific T cells, such as antigen specific naive T cells, activated T cells and memory T cells, as different specific T cell populations.

Furthermore, a further problem to be solved by the present invention was to provide a kit for performing a method for detection of active pathogen specific infections and disease incidents, which relies on the indirect detection of activated pathogen or disease specific T cells.

A further problem to be solved by the present invention was to provide a kit for performing a method for differential diagnosis of active and latent infections and disease incidents, which relies on the indirect detection of activated pathogen or disease specific T cells and their distinction from naive and memory T cells.

The problem underlying the present invention is solved by the subject matter defined in the claims.

BRIEF DESCRIPTION OF THE DRAWINGS

The following figures serve the purpose of illustrating the invention.

FIG. 5 shows in (A) in a diagram the relative increase of the 4-1BBL mRNA production in PBMC loaded and not loaded with ESAT-6/CFP-10 due to cocluturing with ex vivo preactivated autologous ESAT-6/CFP-10 specific T helper cells as determined by RT-qPCR. $1 \times 10^6$ freshly isolated PBMCs of a donor with a latent tuberculosis were cocultured with 50,000 ex vivo preactivated ESAT-6/CFP-10 specific T helper cells in presence and absence of 10 µg/ml ESAT-6/CFP-10. At the indicated time points $2 \times 10^5$ cells were removed, pelleted and frozen in liquid nitrogen. The relative increase in 4-1BBL mRNA in specifically stimulated cell cultures in comparison to unstimulated cells was determined by RT-qPCR. The data of the RT-qPCR was analysed according to $2^{-\Delta\Delta Cq}$ method, wherein GAPDH served as reference gene and the unstimulated control as calibrator. (B) shows in a diagram the relative increase of the IFN-γ mRNA production in the course of the cocultivation of PBMC, loaded or not loaded with ESAT-6/CFP-10, with ex-vivo preactivated autologous ESAT-6/CFP-10 specific T helper cells as determined by RT-qPCR. $1 \times 10^6$ freshly isolated PBMC of a donor with a latent tuberculosis were cocultured with 50,000 ex vivo preactivated ESAT-6/CFP-10 specific T helper cells in presence and absence of 10 µg/ml ESAT-6/CFP-10. At the indicated time points $2 \times 10^5$ cells were removed, pelleted and the relative increase in IFN-γ mRNA in specifically stimulated cell cultures in comparison to non-stimulated cell cultures was determined by RT-qPCR. The data of the RT-qPCR were analyzed according to $2^{-\Delta\Delta Cq}$ method wherein GAPDH served as reference gene and the unstimulated control as calibrator.

FIG. 6 shows in a diagram the antigen specificity of the induction of the 4-1BBL mRNA synthesis by activated Th cells as determined by RT-qPCR technique. Pre-activated ESAT-6/CFP-10 specific T cells show in comparison to expander beads preactivated non-ESAT-6/CFP-10 specific T cells a significantly improved capability to induce the 4-1BBL mRNA production in with ESAT-6/CFP-10 stimulated versus non-stimulated cell cultures. With expander beads unspecifically activated and specifically preactivated ESAT-6/CFP-10 specific Th cells were cocultured with autologous PBMCs in presence and absence of 10 µg/ml ESAT-6/CFP-10, whereby different numbers of T cells with $1 \times 10^6$ freshly isolated PBMCs were used. At the indicated time points $2 \times 10^5$ cells were in each case removed, pelleted and the relative amount of 4-1BBL mRNA was quantified by RT-qPCR. The data of the RT-qPCR were analyzed according to $2^{-\Delta\Delta Cq}$ method, wherein GAPDH served as reference gene and the unstimulated control as calibrator.

FIG. 7 shows in a further diagram the antigen specificity of the induction of 4-1BBL mRNA synthesis by activated Th cells as determined by RT-qPCR technique. Preactivated ESAT-6/CFP-10 specific T cells induce only in ESAT-6/CFP-10 stimulated cell cultures, but not in EBV BZLF1 or CMV pp 65 protein stimulated cell cultures an increased induction of 4-1BBL mRNA production. $1 \times 10^6$ PBMCs of a donor with a persistent *M. tuberculosis* infection were cocultured with about 70,000 preactivated ESAT-6/CFP-10 specific Th cells in presence of 10 µg/ml ESAT-6/CFP-10, EBV BZLF1 or CMV pp 65. As a further control served unstimulated cocultures of preactivated T cells and PBMCs. At the indicated time points $2 \times 10^5$ cells were removed from the sample in each case and the relative content of 4-1BBL mRNA was quantified in a RT-qPCR. The data of the RT-qPCR were analyzed according to the $2^{-\Delta\Delta Cq}$ method, wherein GAPDH was used as reference gene and the unstimulated control was used as calibrator.

FIG. 8 shows in a further diagram the antigen specificity of the induction of 4-1BBL mRNA synthesis in activated Th cells as determined by RT-qPCR technique. Preactivated ESAT-6/CFP-10-, EBV BZLF1- and CMV pp 65-specific Th cells show only an increased induction of 4-1BBL mRNA production in cocultures stimulated with their respective target antigen. (A) to (C) show diagrams of the induction of 4-1BBL-mRNA synthesis by CMV pp 65, EBV BZLF1 and *M. tuberculosis* ESAT-6/CFP-10 specific Th cells in (A) with *M. tuberculosis* ESAT-6/CFP-10, (B) CMV pp 65 and (C) EBV BZLV1 loaded PBMC as determined by RT-qPCR. In each case $1 \times 10^6$/ml PBMC were cocultured with about 70,000 ex vivo expanded pp 65, BZLF1 and ESAT-6/CFP-10 specific Th cells in presence and—as a control—in absence of in each case 10 µg/ml ESAT-6/CFP-10, (B) pp 65 or (C) BZLF1. At the indicated time points $2 \times 10^5$ cells were removed from the sample, the total RNA isolated and transcribed into cDNA and the relative content of 4-1BBL mRNA quantified by way of RT-qPCR. Analysis was done according to the $2^{-\Delta\Delta Cq}$ method by using GAPDH as reference gene and the unstimulated control as calibrator.

FIG. 9 shows in a diagram the increase of the sensitivity of the inventive RTT method by using a MHC-I blocking antibody (W6/32), as determined by RT-qPCR. Unloaded PBMCs or loaded with 10 µg/ml EBV BZLF1 were cocultured with in vitro preactivated BZLF1-specific Th cells in presence and absence of 10 µg/ml of MHC-I blocking antibody W6/32. At the indicated time points $2 \times 10^5$ cells were removed and the RNA purified and analyzed with RT-qPCR technology. Data of the RT-qPCR were analyzed according to the $2^{-\Delta\Delta C_q}$ method, wherein GAPDH was used as reference gene.

FIG. 10 shows in (A) to (E) in diagrams, that donors with a (D) active tuberculosis exhibit in comparison to donors with (B) a latent *M. tuberculosis* infection, (C) a treated TB infection, as well as in comparison to (A) healthy donors a measurable increase of relative induction of 4-1BBL mRNA production in specifically stimulated PBMCs in comparison to unstimulated PBMCs. From freshly isolated, heparinized whole blood of three (A) healthy donors not infected with *M. tuberculosis* (p012, 010, p008), (B) healthy donors with a latent tuberculosis infection (p009, p006, p005), (C) donors, which have been treated with medicaments due to an active tuberculosis in the last 6 months prior to examination (p013, p014, p003) and (D) donors with an active tuberculosis prior to or shortly after initiation of the causal therapy (p001, p004, p007) PBMCs were isolated and incubated in presence or absence of 10 µg/ml ESAT-6/CFP-10. (E) As a control PBMCs of selected donors HIV seronegative donors were stimulated with 10 µg/ml HIV p24 capsid protein (p005, p008, p007, p006, p003) or bovine serum albumine (p001). At the indicated time points cells were harvested and the expression of 4-1BBL in stimulated and non stimulated cells was determined by RT-qPCR. The results were analyzed with the $2^{-\Delta\Delta C_q}$ method. GAPDH served as reference gene.

FIG. 11 shows in (A) to (C) in diagrams that tuberculin PPD stimulated PBMCs of a donor with an (A) active tuberculosis exhibit in comparison to PBMCs of a donor with (B) a latent *M. tuberculosis* infection or of (C) a healthy donor an increased relative induction of 4-1BB mRNA production in specifically stimulated PBMCs in comparison to unstimulated PBMCs. $1\times10^6$ freshly isolated PBMC/ml of donors with an (A) active TB, a (B) latent TB and (C) of a donor not infected with *M. tuberculosis* were stimulated in each case with 10 µg/ml ESAT-6/CFP-10 or tuberculin PPD, respectively, or—as a positive control—with 1 µg/ml PMA/Ionomycin. At the indicated time points $0.5\times10^6$ cells were removed and stored at −80° C. Total RNA was isolated from the cells and transcribed into cDNA and the content of 4-1BBL mRNA was quantified by RT-qPCR. The analysis was done according to the $2^{-\Delta\Delta C_q}$ method by using GAPDH as reference gene and the unstimulated control as calibrator.

DETAILED DESCRIPTION OF THE INVENTION

Figure 1:
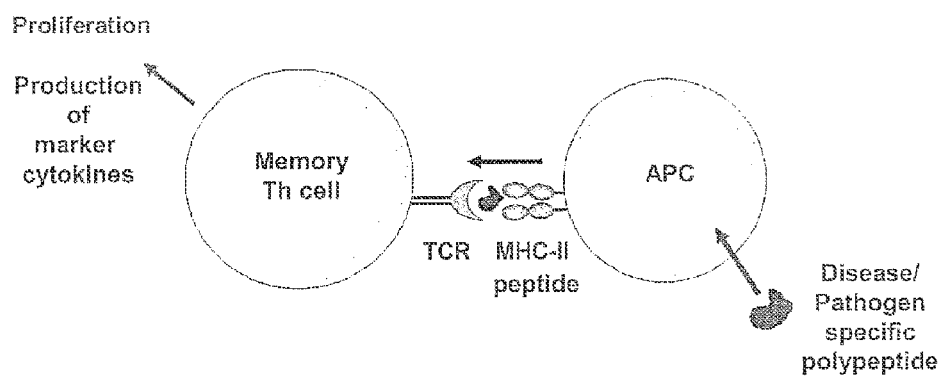
FIG. 1 shows a schematic representation (A) of the principle of hitherto used technologies according to the known prior art and (B) according to the inventive method for detection of specific T cells.
Figure 1:
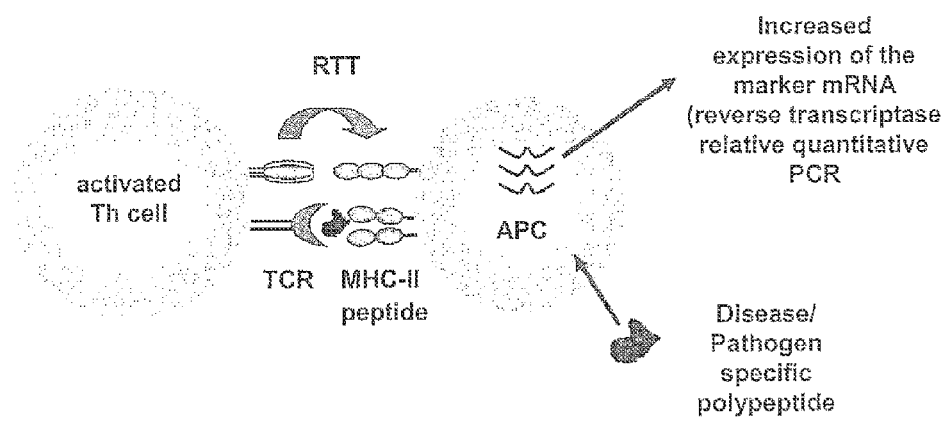

In the context of the present invention a "T cell population" is understood to be a defined group of T cells with a particular phenotype.

T cell populations according to the present invention are in particular naive T cells, activated T cells and memory T cells.

In the context of the present invention the term "T cells" is understood to refer to T lymphocytes, such as $CD4^+$ T cells or $CD8^+$ T cells or a mixture of $CD4^+$ T cells, and $CD8^+$ T cells, respectively. Herein the group of $CD4^+$ T cells encompasses, T helper cells, such as T helper (Th-1) cells, T helper 2 (Th-2) cells, T helper 17 (Th-17) cells, $CD4^+$ $CD25^+$ regulatory T cells (Treg), Tr 1 cells and T helper 3 (Th-3) cells. The group of $CD8^+$ T cells comprises $CD4^-$ $CD8^+$ cytotoxic T cells and T cells, which exhibit a $CD4^+$ $CD8^+$ phenotype ($CD4^+CD8^{dim}$, $CD4^{dim}CD8^{bright}$ or $CD4^{hi}CD8^{hi}$).

In the context of the present invention a naive "T cell" is understood to be a T cell, which exhibits a certain antigen specificity, which however has not yet had the first contact with its antigen. Naive T cells such as naive $CD4^+$ T cells exhibit for example CD45RA as marker on their surface.

In the context of the present invention an "activated T cell" is understood to be a T cell, which is on basis of a naive status prior to a first antigen challenge stimulated by the first antigen contact of the T cell receptor. The recognition of a peptide presented on MHC molecules by the T cell receptor leads to a so-called crosslinking (Crosslinking) of the T cell receptor. A further prerequisite for the activation of T cells is a second signal, which is mediated by the interaction of costimulatory molecules and their ligands on the APCs as well as on the T cells. This activation leads to a signal cascade within the T cells and eventually to a proliferation and the development of various effector functions. In addition, activated T cells are characterized by the transient expression of characteristic surface molecules such as the CD40 ligand, 4-1BB, CD69 and/or CD25. The activation of naive T cells towards activated T cells after the first antigen contact on the surface of a professional antigen presenting cell is also referred to as "priming". The term "activated T cell" is synonymous to the term "effector T cell" and comprises also memory T cells specifically reactivated in vivo by renewed contact with its antigen.

In the context of the present invention a "memory T cell" is understood to be a T cell, which already had specific antigen contact. Memory T cells are characterized by special surface markers such CD45RO, CD44 and L-selectin.

In the context of the present invention the term "antigen presenting cell" (APC) is understood to refer to cells which are capable of taking up polypeptides, processing them and presenting in combination with MHC I and MHC II proteins fragments of said polypeptides, the so-called epitopes, to the immune system. The "antigen presenting cell" comprises in particular so-called professional antigen presenting cells such as dendritic cells, monocytes, macrophages, non-professional APC, such as B cells, but also vascular endothelial cells, fibroblasts of the skin, epithelial cells of the thymus or the thyroid gland, glial cells of the brain, beta cells of the pancreas as well as vascular endothelium cells. Non-professional APCs express the MHC molecules of class I and II, which are required for the interaction with T cells, only after activation by cytokines such as IFN-γ. In addition, T cells may act also as APC. These APC T cells are generated by the intracellular transfer of MHC class I and II molecules as well as of costimulatory molecules, e.g. CD80, CD40 ligand (CD40L), OX40 ligand (OX40L) and 4-1BB ligand (4-1BBL, TNFSF9) due to contact with an APC, in particular a dendritic cell (DC).

In the context of the present invention "marker of the APC" and "marker of the T cell" respectively, is understood to be a nucleic acid, in particular an RNA or a DNA, or a nucleic acid fragment. Furthermore, a "marker of the APC" and a "marker of the T cell", respectively, is also understood to be a peptide, oligopeptide or a protein. According to the invention it is contemplated that the expression of the marker is detectably increased or reduced in the APC after a specific recognition of the antigen in complex with MHC molecules on the APC by an activated T cell. According to the invention it is thus contemplated, that the marker of the APC is induced by the antigen specific interaction of the activated T cells with the APC and thereby becomes detectable and quantifiable.

In the context of the present invention "induced" and "induction" of a marker, respectively, is understood to be the change in expression of the marker. In case the marker is a nucleic acid, "induction" is according to the invention understood to be the increased or decreased production of for example mRNA of a gene. Furthermore, "induction" is understood according to the present invention to be the modulation of a gene, for instance by way of methylation. Furthermore, in the context of the present invention "induced" is understood to refer to the increased or decreased expression of a protein. Hereby, the expression of the protein may occur on the cell as well as in the cell, i.e. intracellularly.

In the context of the present invention an "antigen" is particularly understood to be a protein, a polypeptide or a peptide. An antigen is in particular a polypeptide sequence, which is taken up by APCs, processed and whose fragments, the so-called epitopes, are presented on MHC molecules to T cells. An antigen is in particular also a peptide, which is presented together with MHC molecules to T cells. In addition, an antigen is understood to be a RNA, DNA or an expression plasmid which encodes a polypeptide.

The term "expression plasmid" or "expression vector", as used herein, refers to an artificially created construct for introducing and expressing nucleic acids in cells. Expression vectors are for example bacterial plasmids and MIDGES, virus derived plasmids, phagemids, cosmids, bacteriophages or artificially produced nucleic acids such as artificial chromosomes. Vectors may in addition contain one or more selection markers.

In the context of the present invention the term "polypeptide" is understood to be a polymer of amino acids of any length. The phrase "polypeptide" comprises also the terms target epitope, epitope, peptide, oligopeptide, protein, polyprotein and aggregate of polypeptides. Furthermore, the expression "polypeptide" also encompasses polypeptides, which exhibit posttranslational modifications such as glycosylations, acetylations, phosphorylations, carbamoylations and similar modifications. In addition, the expression "polypeptide" is understood to refer also to polypeptides, which exhibit one or more analogues of amino acids, such as for example non-natural amino acids, polypeptides with substituted linkages as well as other modifications known in the prior art, irrespective thereof, whether they occur naturally or are of non-natural origin.

The term "epitope" as used herein refers to a portion of a polypeptide, which exhibits antigenic properties and serves for example as recognition site of T cells or immunoglobulins. According to the present invention epitopes are for example those portions of polypeptides, which are recognized by immune cells such as for example $CD4^+$ T helper cells, $CD8^+$ cytotoxic T cells, $CD4^+CD8^{dim}$ cytotoxic T cells, $CD56^+CD8^+$ as well as $CD56^-CD57^+CD8^+$ NKT cells or $CD4^+CD25^+$ regulatory T cells. An epitope may comprise 3 or more amino acids. Usually, an epitope consists of at least 5 to 7 amino acids or, which occurs more frequently, of 8 to 11 amino acids, or of more than 11 amino acids, or of more than 20 amino acids, more seldom even more than 30 amino acids.

In the context of the present invention "reverse transcription quantitative real-time polymerase chain reaction, RT-qPCR" is understood to be a method, which is based on the conventional polymerase chain reaction (PCR). In addition, RT-qPCR allows, besides amplification, in addition also a quantification of the target mRNA. For this purpose the total RNA is isolated from the material to be examined and incubated with a antigen and is isolated in comparison from unstimulated material or material incubated with an irrelevant antigen, and is then transcribed into cDNA in a subsequent reverse transcription reaction. By using specific primers the target sequence is then amplified in the qPCR. For quantification of the target sequence several methods may be applied.

The most simple way of quantification is using intercalating fluorescent dyes, such as SYBR green or EVA green. These dyes fit themselves in the double stranded DNA molecules, which arise during the elongation of the specific products. The detection always takes place at the end of the elongation by detecting the emitted light after excitation of the fluorescent dye. With increasing amount of PCR product more dye is incorporated, thus the fluorescent signal increases.

A further possibility of quantification is the use of sequence specific probes. There are hydrolysis (TaqMan) or hybridisation (Light-Cycler) probes. Hydrolysis probes are labelled at the 5' end with a fluorescent dye and at the 3' end with a so-called quencher. Due to the spatial proximity to the reporter dye the quencher is responsible for the quenching of the fluorescence signal and is cleaved off during the synthesis of the complementary DNA in the elongation phase. As soon as the fluorescent dye is excited with a light source at the end of the elongation, light of a specific wave length is emitted, which may be detected.

Hybridisation probe systems consist of two probes, which bind to a target sequence next to each other. Both probes are labelled with a fluorescent dye. With a light source the first fluorescent dye at the 5' end of the first probe is excited. The emitted light is then transferred via fluorescence resonance energy transfer (FRET) to the second fluorescent dye at the 3' end of the second probe. Thereby the dye is excited, whereby light of a specific wave length is emitted, which may be detected. If in the course of the elongation of the complementary strand of the target sequence the first probe is degraded by the polymerase, the FRET may no more take place and the fluorescence signal subsequently decreases. In contrast to the afore-mentioned methods the quantification thus occurs here always at the beginning of the elongation process.

Frequently used fluorescent dyes are for example Fluophor 1, Fluorphor 2, aminocumarin, fluorescin, Cy3, Cy5, europium, terbium, bodipy, dansyl, naphtalene, ruthenium, tetramethylrhodamine, 6-carboxyfluorescein (6-FAM), VIC, YAK, rhodamine and Texas Red. Frequently used quenchers are for example TAMRA™, 6-carboxytetramethoylrhodamine, methyl red or dark quencher.

The term "real-time" refers to a distinct measurement within each cycle of PCR, i.e. in "real-time". The increase of the so-called target sequence correlates herein with the increase of the fluorescence from cycle to cycle. At the end of a run, which usually consists of several cycles, the quantification is then carried out in the exponential phase of the PCR on a basis of the obtained fluorescents signals. Hereby, the measurement of the amplification is usually done via Cq (quantification cycle) values, which described the cycle, in which the fluorescence rises for the first time significantly above the background fluorescence. The Cq value is determined on the one hand for the target nucleic acid and on the other hand for the reference nucleic acid. In this way it is possible to determine absolute or relative copy numbers of the target sequence.

In the context of the present invention the expression reference gene may be understood as a sequence on mRNA level as well as on the level of genomic DNA. These may also be non-transcriptional active under the stimulation conditions according to the present invention or they correspond to non coding DNA regions of the genome. According to the invention a reference gene may also be a DNA or RNA added to the target gene sample. The highest criterion of a reference gene is that it is not altered in the course of the stimulation and by the conditions of the inventive method. The experimental results may thus be normalized with respect to the amount of template used in different samples. The reference gene allows thus the determination of the relative expression of a target gene. Examples for reference genes are glyceraldyhde-3-phosphate-dehydrogenase (GAPDH), huPO (human acidic protein 0), porphobilinogen deaminase (PBGD), β-actin or tubulin.

In a first object of the present invention it is envisaged to provide a method for detection, differentiation and quantification of T cell populations, which comprises the following steps a) contacting a first aliquot of a body fluid of an individual with at least one antigen, wherein the body fluid contains antigen presenting cells (APC) and T cells, b) incubating the first aliquot with the at least one antigen for a defined period of time, c) detection and differentiation of T cell populations by detecting at least a first marker of APC induced by T cells of a specific T cell population in the first aliquot and in a second aliquot of the body fluid of the individual, which has not been incubated with the at least one antigen, by reverse transcription quantitative real time polymerase chain reaction (RT-qPCR), and d) detection and quantification of the T cell populations by determining the ratio of the detected marker of the APC in the first aliquot versus the second aliquot.

According to the invention it is thus envisaged, that detection, differentiation and quantification of T cells of a specific T cell population is carried out by detection and a relative quantification of at least one marker of APC in non-stimulated and/or non specifically and specifically stimulated cell culture samples with RT-qPCR. The inventive method envisages, that the detection and quantification is possible due to the fact that in particular activated T cells contribute via a feedback mechanism to the maturation of antigen presenting cells (APC). In the context of the present invention this feedback mechanism is also referred to as reverse T cell technology (RTT). Thus, antigen specific activated T cells, in particular T-helper cells, induce, mediated by recognition of antigen loaded MHC molecules via the TCR and the simultaneous further interaction of the T cell with the APC, an activation amongst others of for example promoters of various genes as markers of APC, the increased production of mRNA molecules and the increased expression of these marker proteins. Due to these maturation processes the APC obtains an increased capability for stimulating pathogen or disease specific cytotoxic T cells and low affinity T helper cells.

According to the invention it is thus contemplated, that the detection of T cells of a specific T cell population, such as activated T cells, may occur by indirect detection via a marker of the APC. Without being bound by any theory, it is contemplated according to the present invention, that APC present due to incubation with an antigen fragments of this antigen in combination with MHC class II or I molecules on their surface to activated T cells. Thereby a specific binding of the activated T cells to the antigen presenting APC occurs. Due to this specific T cell-APC-interaction the APC becomes specifically stimulated. As a consequence of this specific stimulation induction of a marker in the APC occurs. The determination of the marker in specifically stimulated APCs and in APCs, which are non-stimulated, by reverse transcription quantitative PCR(RT-qPCR) allows the detection, the differentiation and the quantification of activated T cells in form of specific T cell populations.

The inventive method allows a sensitive and reliable detection of T cells of a specific T cell population, such as naive, activated or memory T cells. The sensitivity of the method is in particular due to the fact, that a T cell elicits in the APC the stimulation of the marker inter alia in form of a multitude of mRNA copies. Furthermore, it is discussed, that possibly a larger number of APCs is stimulated by a T cell, the T cell so to say "jumping" from one APC to the other. All in all this leads to a signal enhancement and thereby to an increased sensitivity of the inventive method.

The inventive method thus renders the detection and differentiation of specific T cell populations possible and allows thereby in particular a distinction of activated T cells from memory T cells.

In a preferred embodiment of the invention the normalisation of the gathered real-time PCR data (real-time PCR data) is performed by using a fixed reference value, which is not influenced by the conditions of the experiment, in order to achieve a precise gene expression quantification. For this purpose the expression of a reference gene is also measured in order to perform a relative comparison of amounts.

According to the invention it is contemplated, that for the determination of the marker of the APC a first and a second aliquot of a body fluid of an individual is provided. In the context of the present invention "providing" is understood to imply that an aliquot of the body fluid is already present in a container. "Providing" may also mean according to the invention, that the aliquot of the body fluid is directly provided from a patient, for instance by sampling blood. The inventive method envisages that the first aliquot is stimulated with at least one antigen, while the second aliquot remains unstimulated. All in all it is thus envisaged, that the first and second aliquot are identical except for the contacting with the antigen. Hence, the second unstimulated aliquot serves as a kind of calibrator. The quantification is thus performed relative to the calibrator. For the determination and quantification of the marker it is envisaged, that the amount of marker in the first stimulated aliquot is divided by the amount of the marker in the second unstimulated aliquot. Thus, a n-fold difference in amount of the marker of the first stimulated aliquot relative to the calibrator, i.e. the second unstimulated aliquot, is detected. The inventive method represents a method which is exclusively carried out ex vivo.

The inventive method allows, in advantageous manner over known available methods, the detection of activated T helper cells with an increased sensitivity, speed and reliability of the experimental process. In addition, the inventive method allows in particular a discrimination as well as a differential determination of activated T cells versus memory T cells.

A significant difficulty for the ascertained detection of activated T cell during active microbial infections and in particular in autoimmune and tumour diseases is due to the very low numbers of disease and pathogen specific activated T cells present in the circulation. T cells are activated in lymphatic organs by contact with antigen loaded APCs, proliferate and migrate then via the blood or the lymph to the site of infection or disease, where they often remain and exert their effector functions.

The inventive method is based on the detection of T cell inducible components, such as RNA molecules or proteins, whose production in APCs is after antigen specific contact with an activated T cell measurably modulated, i.e. is increased, reduced or modified.

The determination of T cell induced maturation processes in APCs or APC containing cultures is carried out with previously known methods by detecting markers in form of proteins in cell cultures stimulated specifically with expression vectors using various protein detection methods, such as FACS, ELISpot or ELISA. These methods however turned out to be of only limited suitability or unsuitable for a reliable detection of activated T cells in diagnostic applications.

It is known, that T cell inducible marker molecules are produced in a multitude of different diseases and microbial infections in different cell populations, the subjects or patients to be examined thus exhibiting individually a sometimes strongly varying and partially already very high basic expression level of these marker proteins. Furthermore, APC frequently contain already larger amounts of preformed, i.e. already expressed marker molecules, which are present independent of an antigen specific stimulation by an activated T helper cell. Moreover, an activated T helper cell usually stimulates only one or only a few APCs, respectively, wherein only a limited increase in sensitivity may be achieved on cellular level. Because of these known circumstances it has so far been assumed, that a reliable determination of activated T cells by detecting specific markers on protein level in APCs stimulated by said activated T cells would not be possible on a diagnostically reliable scale.

Surprisingly it could be shown, that the inventive method can be carried out by determining the T cell induced production of, for example, mRNA molecules as markers in APCs. Due to the aforementioned difficulties with respect to the varying expression of certain marker molecules it has to be considered as being unexpected, that the inventive detection of a marker of APC on RNA level allows a reliable and sensitive determination of antigen specific activated T cells. For instance, the contact of an activated T cell with an APC induces the production of very high amounts of mRNA molecules which leads to a strong amplification of the marker and thus to a significantly increased sensitivity of the inventive method.

However, hitherto fundamental technical prejudices existed towards using T cell inducible markers, such as the production of mRNA molecules, in APC as means of detection of activated antigen specific T cells as marker for active disease incidents. These technical prejudices are based in particular on the fact, that specific markers in the APC exhibit individually a very fluctuating base expression. However, compensation of these fluctuations is obligatorily required for the definition of reliable threshold levels for a meaningful test result.

These technical prejudices were overcome in the inventive method in particular by determining the relative increase of the marker expression by detection of the marker of the APC in a first aliquot stimulated with at least one antigen and a second unstimulated aliquot of a body fluid of an individual and the determination of the ratio of the first aliquot to the second aliquot.

In a preferred embodiment of the invention a method is envisaged, wherein in step c) additionally at least a second marker is detected in the first and in the second aliquot, wherein the second marker is an induced marker of the T cells themselves, and wherein step d) comprises the detection and the quantification of T cell populations by determining the ratio of the detected first marker of the APC and the second marker of the T cell of the first aliquot to the second aliquot.

According to the invention it is envisaged for this method, that differentiation of naive T cells, activated T cells and memory T cells as individual T cell populations becomes possible. In that this inventive method provides the possibility of differential diagnosis in specific diseases. For instance, it is inter alia possible for a tuberculosis disease to distinguish by way of such differential diagnosis patients with an active disease and a concomitant need of treatment from patients with a latent infection without a specific need for treatment, and from healthy individuals. This differential diagnosis is enabled by the detection of a first and a second marker.

The first marker represents hereby the T cell induced marker of the APC. This marker is only induced during active disease incidents. The second marker is a marker of the T cell itself. This second marker is formed in presence of activated and memory T cells in the method sample.

In a further preferred embodiment of the invention a method is envisaged, wherein the method comprises in step a) a further step a') contacting the second aliquot with at least one antigen, and in step b) a further step b') incubating the second aliquot with the antigen for a defined period of time, wherein the period of time in step b') differs from the period of time in step b), and instead of step c) a step c') detection and differentiation of the T cell populations by detecting the first marker in the first and the second aliquot by RT-qPCR, and step d).

In a particularly preferred embodiment of the invention it is envisaged, that the period of time for incubation in step b') is 0 minutes. In a further particularly preferred embodiment of the invention the period of time is from 0 to 60 minutes, more preferably from 0 to 45 minutes, more preferably from 0 to 30 minutes, more preferably from 0 to 20 minutes, more preferably from 0 to 15 minutes, more preferably from 0 to 10 minutes, particularly preferred from 0 to 5 minutes. According to the invention it is envisaged, that the second aliquot is contacted with the antigen over a markedly shorter period of time in comparison to the period of time for the incubation of the first aliquot up to a so-called "zero sample", i.e. for a duration of 0 minutes. Thus it is envisaged, that within the incubation period of the second aliquot no marker has yet been formed or only very low amounts of marker are till then present. In particular it is according to the invention envisaged that the period of time in step b') is markedly shorter than the period of time in step b). According to the invention the incubation of the second aliquot with the antigen in step b') thus occurs only in a range of a few seconds up to a period of time lasting 0 minutes or occurs at least not over a prolonged period of time.

In a further preferred embodiment of the invention it is envisaged, that the second aliquot is contacted in step a') and incubated in step b') with an irrelevant antigen. According to the invention an irrelevant antigen is understood to be an antigen, for which the individual does not have activated or memory T cells. Such an irrelevant antigen may for example be albumin or an HIV protein in HIV seronegative persons.

In a preferred embodiment of the invention a method is envisaged, wherein step c') comprises the detection and differentiation of the T cell populations by detecting the first and the second marker.

In a further preferred embodiment of the invention a method is envisaged, wherein the aliquot of the body fluid is separated into an aliquot A containing only APCs and in an aliquot B containing T cells, and wherein step a) comprises a step a1) contacting the aliquot A with at least one antigen, and a subsequent step a2) contacting the aliquot A contacted with the at least one antigen with aliquot B.

According to the invention it is contemplated, that prior to adding the T cells the APC are first loaded with the antigen. According to the invention it is more preferably envisaged that the T cell containing aliquot B also contains unloaded APCs, i.e. APCs without prior antigen contact.

According to the invention it is envisaged, that the T cell populations contain naive T cells, activated T cells or memory T cells.

In a preferred embodiment of the invention it is envisaged, that the T cells of the T cell population are $CD4^+$ T cells, in particular Th-1 cells, Th-2 cells, Th-17 cells, $CD4^+CD25^+$ regulatory T cells, Th-3 cells, $CD^8$ T cells, in particular $CD4^-CD8^+$ cytotoxic T cells, $CD4^+CD8^+$ T cells, $CD161^+$ NKT cells and/or a mixture of various T cells.

According to the invention it is furthermore preferably envisaged, that the body fluid is blood, cerebrospinal fluid, lymph, pericardial fluid, a bronchial lavage, a bone marrow aspirate, a suspension of lymphatic tissue or a purified PBMC population.

In the context of the present invention "lymphatic tissue" is understood to be lymph nodes, spleen, tonsils as well as the lymphatic tissue of the gastrointestinal mucous membrane, such as peyers plaques, the lymphatic tissue of the respiratory organs and of the urinary tracts.

In a further preferred embodiment of the invention it is envisaged, that the body fluid contains additionally a separated APC population. Furthermore, according to the invention a so-called buffy-coat is preferred as body-fluid.

In a further preferred embodiment of the invention is envisaged, that the antigen is a peptide, oligopeptide, a polypeptide, a protein, an RNA or a DNA.

In a further preferred embodiment the antigen is an expression plasmid.

According to the invention the antigen is furthermore preferably a fragment, a cleavage product or a piece of an oligopeptide, of a polypeptide, of a protein, of an RNA or of a DNA.

According to the invention it is envisaged as preferred, that the antigen is an antigen from a bacteria, virus, plant, animal, fungi or parasite.

In a further preferred embodiment of the invention it is envisaged, that the antigen is a polypeptide of the cytomegalovirus (CMV), Epstein-Barr Virus (EBV), Hepatitis B virus (HBV), Hepatitis C virus (HCV), human immunodeficiency virus (HIV), parvovirus B19, Varicella Zoster virus (VZV), vaccinia virus, adenovirus, JC- and BK-virus, A, B, C type influenza virus, *Mycobacterium tuberculosis, borrelia, Toxoplasma gondii* or aspergilli or a tumour or auto antigen.

According to the invention the antigen is preferably an antigen from viruses with human pathogenic properties. In following examples according to the present invention are given for such viruses. This list shall not be considered as being limiting in the context of the present invention, but rather as representing merely examples. Polioviruses, Coxsachieviruses, echoviruses, enteroviruses, rhinoviruses, orthomyxoviruses, in particular type A, B, C influenza viruses, paramyxoviruses, in particular parainfluenzaviruses, mumps viruses, measles viruses, respiratory syncytial viruses (RS-virus), coronaviruses, flavivruses, in particular yellow fever-, dengue-, Japan B-enzephalitis-, tick-borne encephalitis (TBE) virus, the hepatitis C virus (HCV), togaviruses, in particular Alpha- and rubiviruses, bunyaviruses, in particular the bunya-, hanta-, nairo-, phlebo- and tospovirus, generaviruses, rubella viruses, rabies viruses, arenavirus, in particular the lymphocytic choriomeningitis virus (LCMV) and the lassa fever virus, gastroenteritis viruses, in particular rotaviruses, adenoviruses, caliciviruses, astroviruses, coronaviruses, retroviruses, in particular type A, B, C and D retroviruses, lentiviruses, in particular the human immune deficiency viruses type-1 (HIV-1) and -2 (HIV-2), the simian immunodeficiency virus (SIV), feline immunodeficiency virus (FIV), bovine immunodeficiency virus (BIV), spumaviruses, the human T cell-leukemia viruses type-1 (HTLV-1) and -2 (HTLV-2), parvoviruses, in particular parvovirus B19 and adeno-associated viruses (AAV), papovaviruses, in particular papillomaviruses, the virus of the progressive multifocal leukoencephalopathy (PML), BK-virus, adenoviruses, herpes viruses, in particular the Herpes Simplex virus type-1 (HSV-1) and -2 (HSV-2), the varicella zoster virus (VZV), cytomegalovirus (CMV) and Epstein-Barr virus (EBV), the human herpes viruses 6, 7 and 8 (HHV 6, 7 and 8), hepatitis viruses, in particular hepatitis A virus (HAV), hepatitis B virus (HBV), hepatitis C virus (HCV), hepatitis D virus (HDV), hepatitis E virus (HEV) and hepatitis G virus (HGV) as well as the transfusion transmitted virus (TTV) and poxviruses, in particular ortho-poxviruses, such as the human pox virus, vaccinia viruses, cowpox viruses, and parapox viruses. Furthermore, the polypeptides may be derived from viral pathogens of rare, subacute or chronic diseases, in particular Marburg and ebolaviruses, as well as bornaviruses.

According to the invention the antigen is particularly preferred a polypeptide of the human immunodeficiency virus (HIV), for example gp120, gp160, p17, p24, Pr55$^{gag}$, polymerase (Pol), reverse transcriptase (RT) and nef.

Furthermore, according to the invention the antigen is particularly preferred a polypeptide of the Epstein-Barr virus (EBV), such as EBNA1, EBNA2, EBNA3A, EBNA3B (EBNA4), EBNA3C (EBNA-6) BZLF1, BMLF1, BMRF1, BHRF1, BARF0, BRLF1, BI'LF4, gp85, gp110, gp220/350, VCA p150, EBNA-LB, LMP1 and LMP2 (e.g. compiled in Khanna et al. (2000), Annu. Rev. Microbiol. 54:19-48).

Furthermore, according to the invention the antigen is particularly preferred a polypeptide of the cytomegalovirus (CMV), such as UL123 (IE1), UL122 (IE-2), UL83 (pp 65), UL82, HL99, UL28, UL33, UL37, US3, UL94, UL16, UL55(gB), UL85, UL25, US18, UL45 and UL32 (pp 150) (e.g. compiled in Crough et al. (2009) Clin Microbiol Rev. 22:76-98).

Furthermore, according to the invention the antigen is particularly preferred a polypeptide of the varicella zoster virus (VZV), such as ORF1, ORF4, ORF10, ORF14, ORF29, ORF62 and ORF68 (gE).

Furthermore, according to the invention the antigen is particularly preferred a polypeptide of the hepatitis B virus, such as HBsAg and HBcAg.

Furthermore, according to the invention the antigen is particularly preferred a polypeptide of adenovirus, such as AdV5 hexon protein.

Furthermore, according to the invention the antigen is preferably an antigen of viruses pathogenic for animals, which are listed in the following. This list shall in the context of the present invention not be considered as being limiting but rather as representing merely examples. The equine morbillivirus (EMP), picornaviruses, in particular enteroviruses, aphthoviruses with the pathogen of the food and mouth disease (FMD), the vesicular stomatitis virus, paramyxoviruses, in particular morbilliviruses, avian paramyxoviruses, poxviruses, in particular capripoxviruses, bunyaviruses, reoviruses, in particular orbiviruses, flaviviruses, in particular pestiviruses, orthomyxoviruses, in particular the influenza A virus, herpesviruses, in particular alpha herpesviruses, rabies viruses, retroviren, in particular lentiviruses and C-type retroviruses, togaviruses, rhabdoviruses, birnaviruses, coronaviruses and caliciviruses.

A comprehensive list of currently described viruses has been compiled for example by the International Committee on Taxonomy of Viruses (International Committee on Taxonomy of Viruses (ICTV)) an may be accessed via the internet (world-wide-web at ncbi.nlm.nih.gov/Taxonomy/Browser/wwwtax.cgi?mode=Undef&name=Viruses&1fl=3&srchmode=1&keep=1&unlock).

Furthermore, according to the invention the antigen is preferably an antigen of bacteria. According to the invention particularly preferred are antigens of human pathogenic bacteria. In the following examples according to the invention for such bacteria are listed. This list shall not be considered in the context of the present invention to be limiting but rather as merely representing examples. Staphylococci, streptococci, enterococci, Neisseria, Enterobacteriaceae, in particular *Escherichia coli* (*E. coli*), including *E. coli* strains pathogenic for babys (EPEC), enteroaggregative *E. coli* strains (EAggEC), *Klebsiella, Enterobacter, Serratia, Proteus, Citrobacter* and typhoid *Salmonella*, Enteritis *Salmonella, Shigella, Yersinia, Vibrios*, in particular *Vibrio cholerae* and *Vibrio El Tor, Pseudomonia, Burkholderia, Stenotrophomas*,

*Acinetobacter, Campylobacter, Helicobacter*, in particular *Helicobacter pylori, Hemophilus, Bordetella, Legionella, Listeria, Brucella, Francisella, Erysipelothrix, Korynebakteria, Bacillus, Clostridia, Bacteroides, Prevotella, Porphyromonas, Fusobacteria, Anaerobiospirillum, Anaerorhabdus, Anaerovibrio, Butyrivibrio, Centripedia, Desulfomonas, Dichelobacter, Fibrobacter, Leprotricha, Megamonas, Mitsuokella, Rikenella, Sebaldella, Selenomonas, Succinovibrio, Succinimonas, Tisserella, Mycobacteria*, in particular *M. tuberculosis*, atypical Mycobacteria (MOTT) and *M. leprae, Nocardia, Treponema*, in particular *T. pallidum* and *T. carateum, Borrelia*, in particular *B. burgdorferi sensu lato, B. garinii, B. afzelii, B. valaisiana, B. lusitaniae* and *B. spielmanil* A14S and *B. recurrentis, Leptospira, Ricksettsia, Coxiella, Ehrlichia, Bartonella, Mycoplasma*, in particular *M. pneumoniae* and *M. hominis, Ureaplasma, Actinomyceta, Chlamydia*. Furthermore, according to the invention the antigens may preferably derived from further medical relevant bacteria, such as for example *Tropheryma*, *Pasteurella*, *Branhamella*, *Streptobacillus*, *Spirillum* and *Gardnerella*.

Furthermore, according to the invention the antigen is more preferably a polypeptide of *M. tuberculosis*, such as CFP-10, ESAT-6, TB7.7, TB37.6 and MPT63 or a polypeptide mixture, such as tuberculin PPD.

Furthermore, according to the invention the antigen is particularly preferred a polypeptide of *Borrelia* spec, such as VlsE, p58 (OppA-2), BBK32, p14, p20 (BBQ03), p21-24 (OspC), p37-38 (FlaA), p41 (Flagellin, FlaB), p19 (OspE), p18, Crasp3, BBA36, BB0323, p26 (OspF), p28 (OspD), p30, p39, (BmpA), p60-65 (common antigen, Hsp60), p83-100, p17 (Osp17), p31-32 (OspA) and p34 (Osp B) or *Borrelia* lipids or a lysate of *Borrelia* strains.

In further preferred embodiment of the invention the antigen is an antigen of bacteria pathogenic for animals. In the following examples according to the invention for such bacteria are listed. This list shall in the context of the present invention not be considered to be limiting, but rather as representing merely examples. *Mycoplasma*, *Bacillus*, in particular *Bacillus anthracis*, *Brucella*, *Mycobacteria*, in particular *M. tuberculosis* and *M. bovis*, *Campylobacter*, *Tritrichomonas*, *Leptospira*, *Rickettsia*, *Salmonella*, *Clostridia*, *Actinobacilli*, *Clamydia*, *Echinococci*, *Listeria*, *Yersinia*, *Corynebacteria* and *Francisella*. A comprehensive list of the currently described bacteria is accessible via the internet at world-wide-web at ncbi.nlm.nih.gov/Taxonomy/Browser/wwwtax.cgi?mode=Root.

In a further preferred embodiment of the invention the antigen is a fungal antigen. In a particularly preferred embodiment of the invention the antigen is derived from a fungus pathogenic for humans. In the following examples according to the invention for such fungi are listed. This list shall in the context of the present invention not be considered as being limiting but rather as representing merely examples. Yeast, in particular *Candida*, *Cryptococcus*, *Malassetia*, *Hyphomycetes*, in particular *Aspergillus*, *Trichphyton*, *Microsporum*, and *Epidermophyton*, dimorphic fungi, in particular *Histoplasma*, *Blastomyces*, *Coccidioides*, *Paracoccidioides*, *Sporothrix*, and *Pneumocystis*.

In a further embodiment of the invention the antigen is an antigen of a parasite. In a preferred embodiment of the invention the antigen is derived from a parasite pathogenic for humans. In the following examples according to the invention for such parasites are listed. This list shall in the context of the present invention not be considered as being limiting but rather as representing merely examples. Protozoa, such as *Trypanosoma*, *Leishmania*, *Trichomona*, *Giardia*, *Amoebae*, *Plasmodia*, *Toxoplasma*, *Cryptosporidia*, *Microsporidia*. Trematoda, such as *Schistosoma*, as well as Cestoda, such as tape worms and Echinococci, as well as Nematoda, such as *Trichuris*, *Trichinella*, *Strongyloides*, *Ancyclostoma*, *Necator*, *Enterobius*, *Ascaris* and *Filarioidea*. In a further preferred embodiment of the invention the antigen is a polypeptide of parasites pathogenic for animals. In the following examples according to the present invention for such parasites pathogenic for animals are listed. This list shall in the context of the present invention not be considered as being limiting but rather as representing merely examples. Protozoa, in particular Protomonas, Diplomonas, Polymastigidia, Amoebae, *Toxoplasma* and Coccisidia, Microspora, Helminthes, Trematora, Cestoda and Nematoda.

In a further preferred embodiment of the invention it is envisaged, that the antigen is a tumour antigen or an autoantigen. In the context of the present invention an "autoantigen" is understood be a antigen, which exhibits structures in the form of peptide fragments, which represent the bodies own structures. In cases in which T cells are present, which exhibit reactivity against such autoantigens, the presence of an autoimmune disease is possible. Autoantigens are also termed self antigens or autoimmune antigens.

In the context of the present invention it is envisaged, that activated T cells, which indicate a tumour disease or an autoimmune disease, respectively, may be detected by incubation with a tumour associated or an autoimmune antigen.

In a preferred embodiment of the present invention the antigen is a human tumour antigen. According to the invention particularly preferred are the prostate-specific antigen (PSA), HER-2/neu, Mucin-1, overexpressed wild-type p53 as well as p53 exhibiting point mutations, MAGE antigen and CEA (Carcino-Embyonic-Antigen).

In a further preferred embodiment the antigen is an autoimmune antigen. According to the invention preferred is an autoimmune antigen for multiple sclerosis (MS), such as the myelin basic protein (MBP), the myelin oligodendrocytes glycoprotein (MOG), the myelin proteolipid protein (PLP), myelin, the MBP/PLP fusion protein (MP4), the myelin associated basic protein of oligodendrocytes (MOBP), the oligodendrocytes specific protein (OSP), the myelin-associated glycoprotein (MAG) as well as glycoprotein P0, the peripheral myelin protein 22 (PMP-22/PAS-II), the p170k/SAG (Schwann Cell Membrane glycoprotein), the oligodendrocyte myelin glycoprotein (OMgp), the Schwann cell myelin protein (SMP), the transaldolase, S 100B, Alpha B crystallin, 2',3'-cyclic nucleotide 3' phosphodiesterase (CNP), the ciliar neurotrophe factor (CNF) and the glial fibrous acidic protein (GFAP).

Furthermore, according to the invention an autoimmune antigen for type 1 diabetes (juvenile diabetes mellitus), such as insulin B, preproinsulin (PPI), the tyrosine phosphatase IA-2, the glutamic acid decarboxylase 65 (GAD65), the heat shock protein Hsp60, the islet cell protein ICA69, IGRP, cd4, chromogranin A (ChgA) (see also Velthuis et al. (2010) Diabetes) is preferred.

In a particularly preferred embodiment of the invention the antigen is selected from the group consisting of PSA, HER-2/neu, mucin-1, MAGE, CEA, myelin basic protein (MBP), myelin oligodendrocyte glycoprotein (MOG), myelin proteolipid protein (PLP), myelin, insulin B, pre-pro-insulin, IA-2, GAD65, Hsp60, ESAT-6, CFP-10, TB7.7, TB37.6, MPT63, tuberculin PPD, p14, OspC, p37-38 (FlaA), p41, OspE, OspF, OspD, p39, Osp17, OspA, OSP B, Pr55$^{gag}$, p24, p17, POL, RT, nef, pp 65, IE1, IE2, BZLF1, EBNA3, EBNA2, EBNA6, BMLF1, EBNA1, ORF1, ORF4, PRF62, ORF68, HBsAg, HBcAg and AdV5.

In a further preferred embodiment of the invention the antigen is selected from polypeptides, which contain epitopes of T helper cells.

In a further preferred embodiment of the invention it is envisaged, that the period of time for contacting in step a) and the incubation in step b) is from 0 hours to 72 hours, preferably 4, 6 or 8 hours. Furthermore it is envisaged as being preferred, that the period of time in step a) and/or step b) is from 0 hours to 72 hours, preferably 4, 6 or 8 hours. Furthermore, preferably according to the invention the period of time in step a) and/or step b) is a period of time from 0 to 48 hours, more preferably from 0 to 36 hours, more preferably from 0 to 34 hours, more preferably from 0 to 32 hours, more preferably from 0 to 30 Hours, more preferably from 0 to 28 hours, more preferably from 0 to 26 hours, more preferably from 0 to 24 hours, more preferably from 0 to 22 hours, more preferably from 0 to 20 hours, more preferably from 0 to 18 hours, more preferably from 0 to 16 hours, more preferably from 0 to 15 hours, more preferably from 0 to 14 hours, more preferably from 0 to 12 hours, more preferably from 0 to 10 hours, more preferably from 0 to 9 hours, more preferably from 0 to 8 hours, more preferably from 0 to 7 hours, more preferably from 0 to 6 hours, more preferably from 0 to 5 hours, more preferably from 0 to 4 hours, more preferably from 0 to 3 hours, more preferably from 0 to 2 hours and more preferably from 0 to 1 hour. In a further preferred embodiment of the invention the period of time in step a) and/or step b) is 0 to 60 minutes, more preferably 0 to 50 minutes, more preferably from 0 to 40 minutes, more preferably 0 to 30 minutes, more preferably 0 to 20 minutes, more preferably 0 to 15 minutes, more preferably 0 to 10 minutes and more preferably 0 to 5 minutes.

According to the invention it is furthermore envisaged as preferred, that the first marker of APC and the second marker of the T cell is a nucleic acid or a protein, in particular an RNA, a DNA, a nucleic acid fragment, a peptide or a peptide fragment, and is induced by contact and incubation with the at least one antigen.

In a further preferred embodiment of the invention it is envisaged, that the marker of the APC is 4-1BB Ligand (4-1BBL), OX40 ligand (OX40L), TNFSF (CD70), B7.1 (CD80), B7.2 (CD86), FcγRIII (CD16), FcγRII (CD32), FcγRI (CD64) or a further representative of the TNF/TNF-receptor and/or immunoglobulin superfamily or a member of the CXCL family e.g. CXCL9, CXCL10, CXCL11 or a member of the chemokine (C-C motif) ligand family e.g. CCL2, CCL 7, CCL8, CCL10 or IL1RN.

In a further preferred embodiment of the invention it is envisage, that the marker of the T cell is IFN-β, INF-γ, TNF-α, IL-2, IL-4, IL-5, IL-6, IL-10, IL-12, IL-β, GM-CSF, TGF-β, MIP1a, MIP1b, 4-1BB, CD25, perforin and/or granzyme. Furthermore, according to the invention it is envisaged that the marker of the T cell is a further cytokine or chemokine produced by activated T cells or reactivated memory T cells.

Preferred markers according to the invention are in particular nucleic acids, which are naturally detectibly increased in their production in an APC after epitope-specific recognition of the APC by a T cell. Examples for such nucleic acids being inventive markers of the APC are mRNA molecules of 4-1BB ligand (4-1BBL) and the OX40 ligand (OX40L) (Oshima et al. 1997, J. Immunol. 159, 3838-3848; den Haan and Bevan; 2000, PNAS 97, 12950-12952). Furthermore, according to the invention preferred are mRNA molecules of the costimulatory proteins B7.1 (CD80), B7.2 (CD86) and of Fas ligand (FasL), as well as other proteins of the TNF/TNF receptor family and immunoglobulin superfamily, as well as various Fc-receptors and mRNA molecules of cytokines and chemokines. In addition, according to the invention preferred are nucleic acids of any polypeptide, whose production is detectably increased or reduced in an APC due to specific recognition of a polypeptide presented together with MHC proteins on the surface of the same APC by an activated T cell.

In a further preferred embodiment of the invention it is envisaged, that the detection and the quantification in step c) and d) is carried out additionally by PCR quantitative PCR (qPCR) microarray, FACS, ELISpot and/or ELISA.

A further subject matter of the present invention relates to a kit for carrying out the inventive methods comprising at least one antigen and a primer pair for amplification of the first marker.

In a further preferred embodiment of the invention the kit comprises furthermore a pair of primers for amplification of the second marker. In a further preferred embodiment the kit comprises furthermore a pair of primers for amplification of the reference gene. Furthermore, it is according to the invention preferred if the kit contains additionally probes as well as a cell culture media.

In a further preferred embodiment according to the invention the kit additionally comprises RNA-stabilising reagents, a RT-master mix, a qPCR-master mix, a positive control, and a positive reagent. According to the invention a "positive control" is understood to be a defined amount of the marker DNA to be amplified. According to the invention a "positive reagent" is understood to be a reagent, which stimulates the marker of the APC unspecifically even in the absence of the activated T cell. Inventive examples for a "positive reagent" are PMA/Ionomycin or an activating anti-CD40 antibody in combination with prostaglandin E2 ($PGE_2$).

EXAMPLES

In a preferred embodiment of the invention it is envisaged, that the kit comprises furthermore primer, which allow the detection of markers of the APC by PCR, qPCR or mircoarray.

In the following the invention is illustrated by the subsequent examples. These examples are to be considered as specific embodiments of the invention and shall not be considered to be limiting.

In order to establish the method for detection, differentiation and quantification of specific T cell populations, such as activated T cells, T cell induced maturation processes in antigen-presenting cells (APC) were analysed. For this purpose a cell culture model was developed, which is based on the coculture of antigen-loaded APC with ex vivo expanded, activated antigen-specific T helper cells. In this model system cocultures of (i) unloaded APCs or of APCs loaded with an irrelevant antigen with pre-activated antigen-specific T helper cells and (ii) antigen-loaded APCs with un-specifically activated T cells or activated T helper cells with a specificity for an irrelevant antigen serve as negative controls. The detection of antigen specific T helper cells (Th cells) is done in this system by comparative quantification of the marker mRNA production in specifically stimulated an unstimulated culture samples by reverse transcription quantitative real time polymerase chain reaction (RT-qPCR).

a) Ex Vivo Expansion of Antigen-Specific Th Cells

For the generation of ESAT-6/CFP-10-specific activated Th cells CD4$^+$ T cells of donors with a latent *Mycobacterium tuberculosis* infection were expanded for a period of 3-4 weeks in vitro. For this purpose the blood of the donors was extracted in a heparinized syringe, diluted with $PBS_{without}$ (phosphate buffered saline without bivalent ions; Lonza) and then the blood cells were separated according to their density via a density centrifugation gradient using Pancoll (Pan Biotech) for 30 min at 20° C. and 800×g. Subsequently the PBMCs were isolated from the gradient and washed two times with $PBS_{without}$ for 10 min at 300×g. Then the CD4$^+$ T cells were isolated by using the MACS technique (CD4$^+$ T cell isolation kit II, Miltenyi) and cultured by weekly stimulation with an ESAT-6/CFP-10 fusion protein (A G Lindner, Institute for medical Microbiology and Hygiene, University Hospital Regensburg) loaded, autologous APC (mature dendritic cells, PBMC) in a ratio of 1:3 (Th cells: APC) in complete R5 media (RPMI 1640 (Pan Biotech), 5% human AB serum (produced from the blood of donors with blood group AB), 1% penicillin/streptavidin (PAN Biotech)). For this purpose the APC were loaded with 10 μg/ml of the ESAT-6/CFP-10 fusion protein in a concentration of 1×10⁷ cells/ml in complete R5 media for 3 hours (h) at 37° C. in humidified atmosphere with 5% $CO_2$ and were subjected γ-radiation of 30 Gy prior to culturing with the isolated Th cells. For an optimal proliferation of the Th cells 50 U/mL recombinant IL-2 (Proleukin S, Novartis) were added to the cultures. The proliferation of the Th cells was weekly determined by detection of the total cell number of vital cells by using a hemocytometer. The specificity of the culture was likewise determined weekly by detecting the number of IFN-γ and CD40L positive T cells after stimulation with irradiated PBMCs loaded with ESAT-6/CFP-10. For this purpose the Th cells of the expansion culture were incubated in a ratio of 1:1 with freshly isolated autologous PBMCs for 6 h at 37° C. and 5% $CO_2$ in presence of 10 μg/ml ESAT-6/CFP-10. After two hours of incubation brefeldin A was added to abolish the cytokine release from the cells. Samples stimulated in each case with 1 μg/ml PMA/Ionomycin and unstimulated samples, respectively, served as positive and negative controls. 1 μg/ml costimulatory monoclonal anti-CD49d and anti-CD28 antibodies were added to each stimulation sample. Subsequent to the incubation followed a single washing step. For this purpose 9 ml $PBS_{without}$ were added to the cells and the cells centrifuged at 4° C. and 300×g for 8 minutes. The supernatant was discarded and the cells were resuspended in the reflux. Then the surface molecules were labelled with in each case 5 μl of the following fluorophor-conjugated antibodies: anti-CD3 allophycocyanin-H7 (BD), anti-CD4 allophycocyanin (BD), anti-CD8 peridinin chlorphyll protein (BD). The surface staining was done for 20 min in the dark at room temperature. Then the cells were washed and fixed with 500 μl 2% paraformaldehyde (PFA) (Sigma Aldrich) in $PBS_{without}$ for 10 min at room temperature in the dark. After a further washing step the staining of the intracellular IFN-γ as well as of the intracellular CD40L was done 30 min at room temperature in the dark in presence of 10 μl 2% saponin (Carl Roth) in $PBS_{without}$ for permeabilisation of the cells by using 1 μl anti-IFN-γ-fluorescein isothiocyanate (BD) and 10 anti-CD40L R-phycoerythrin (BD). Then the cells were washed twice with 0.1% saponin in $PBS_{without}$ and resuspended in 300 μl 1% PFA in $PBS_{without}$. The stained cells were analysed in a FACS CANTO II flow cytometer (BD). For this purpose the cell populations were first separated according to forward scatter light and side scatter light. The lymphocyte populations were then analysed with respect to their expression of CD3. All CD3⁺ cells were then analyzed with respect to expression of the CD4 and CD8 protein. CD4⁺ T cells were then analyzed with respect to expression of IFN-γ and CD40L.

For this purpose the percentage of activated ESAT-6/CFP-10 as specific T helper cells was determined on basis of the expression of IFN-γ and CD40L (data not depicted). In the expansion cultures a continuous proliferation of T helper cells was observable, which was accompanied by an increase of ESAT-6/CFP-10 specific Th cells. Thus, after 3-4 weeks 5 to 18% specific Th cells could be generated in the expansion cultures. The generation and characterisation of EBV-(BZLF1) and CMV- (pp 65) specific Th cells was done analogous to the aforementioned experimental procedure by using blood samples of EBV- and CMV-seropositive donors, respectively.

b) Cocultures of Ex Vivo Preactivated ESAT-6/CFP-10 Specific Th Cells with Freshly Prepared Autologous PBMCs Loaded with ESAT-6/CFP-10 Fusion Protein.

Freshly prepared PBMCs of donors with latent tuberculosis were cocultured in B cell media (Iscove's Modified Dulbecco's Medium (IMDM) (Lonza), 10% human AB serum, 6 ng/ml IL-4 (Miltenyi Biotech), 50 ng/ml transferrin (Roche), 5 μg/ml insulin (Roche) in a ratio of 1:1 with a total cell number of 1×10⁶ cells/ml in presence and absence of 10 μg/ml ESAT-6/CFP-10 fusion protein with ex vivo preactivated ESAT-6/CFP-10 specific Th cells of the expansion culture. The cells were incubated for 10 h at 37° C. in 5% $CO_2$, wherein samples of in each case 2×10⁵ cells were removed at different time points (e.g. after 0; 0.5; 1; 2; 3; 4; 6; 8 and 10 h). These were swiftly centrifuged, the supernatant discarded and the pellet immediately frozen in liquid nitrogen. Until further processing the samples were stored at −80° C. Beforehand in one coculture of the freshly prepared PBMCs with the autologous ex vivo preactivated Th cells the presence of the activation marker CD40L on the surface of the Th cells was analyzed over time after stimulation with ESAT-6/CFP-10. These analyses show, that specifically in vitro restimulated Th cells exhibit a transient expression of CD40L on their surface, wherein the highest number of CD40L expressing cells was observable after 6 hours of coculture with antigen loaded APCs (data not shown).

c) Quantification of 4-1BBL mRNA in PBMCs Using RT-qPCR as Indirect Detection Of Antigen Specific Activated Th Cells Using the peqLab peq GOLD total RNA kit (peqLab), the total RNA was isolated from the cell samples. DNA contaminations were removed using the peqGOLD DNaseI Digest Kit (peqLab). The total RNA was eluted in 60 μl DEPC water (1 L distilled water plus 1 ml diethylpyrocarbonate (Sigma); incubation for 1 h at 37° C. and subsequent autoclaving for 15 min at 121° C.

For the reverse transcription (RT-PCR) into cDNA 10 μl of the eluted RNA were mixed with 10 μl of the RT-PCR master mix. The RT-PCR master mix contains in DEPC water 50 mM buffer A (TaqMan 1000 RXN Gold with buffer A (Applied Biosystems), 5 mM $MgCl_2$ (TaqMan 1000 RXN Gold with buffer A (Applied Biosystems)), 2.5 mM randomized hexamer primer (MWG Operons/Eurofins), 5 mM dNTP, 2.5 U/μl MuLV reverse transcriptase (Applied Biosystems), 1 U/μl RNase inhibitor (Applied Biosystems). The reverse transcription was done for 15 min at 23° C., 5 min at 95° C. and 30 min at 42° C. and by using a PTC-200 Peltier thermocycler (MJ Research). Then 24 μl qPCR mastermix (50 mM buffer A, 6.875 mM $MgCl_2$, 0.308 μM 4-1BBL forward primer GAGGGTCCCGAGCTTTCG, biomers, represented in SEQ ID NO:1; 0.308 μM 4-1BBL reverse primer GCCCATCGATCAGCAGAAC, biomers, represented in SEQ ID NO:2; 0.2525 μM 4-1BBL probe FAM-CCACCAGCTGCGCAAACATGC-TMR, TIB Molbiol, represented in SEQ ID NO:3; 0.308 μM GAPDH forward primer GAAGGTGAAGGTCGGAGTC, biomers, represented in SEQ ID NO:4; 0.308 μM GAPDH reverse primer GTAAACCATGTAGTTGAGGTC, biomers, represented in SEQ ID NO:5; 0.2525 μM GAPDH probe YAK-TCATTGATGGCAACAATATCCACT-TMR, TIB Molbiol, represented by SEQ ID NO:6; 0.003125 U/μl TaqGold polymerase in DEPC water were mixed with 6 μl of the generated cDNA. The temperature profile of the qPCR comprised a 10 minutes step at 95° C. and subsequently 50 cycles consisting of 15 s at 95° C. and 1 min at 60° C. and was done with a StepOnePlus real time PCR system (Applied Biosystems).

THP-1 cells, which constitutively express 4-1BBL mRNA, served as positive control and reference. These were treated in the test in the same manner as the samples. Subsequently a relative quantification of the 4-1BBL mRNA was done by using the likewise previously amplified glyceraldehyde 3-phosphate dehydrogenase (GAPDH) as reference gene according to the following formula:

$$R = 2^{-\Delta\Delta Cq}$$

ΔΔCq=[(Cq 4-1BBL(S)–Cq GAPDH(S)]–[(Cq 4-1BBL (NK)–Cq GAPDH(NK)] The results are given as ratio of the marker mRNA production of the stimulated sample and the corresponding negative control, which have been previously normalized with GAPDH. For each sample the analysis was done in triplicate.

Figure 3:
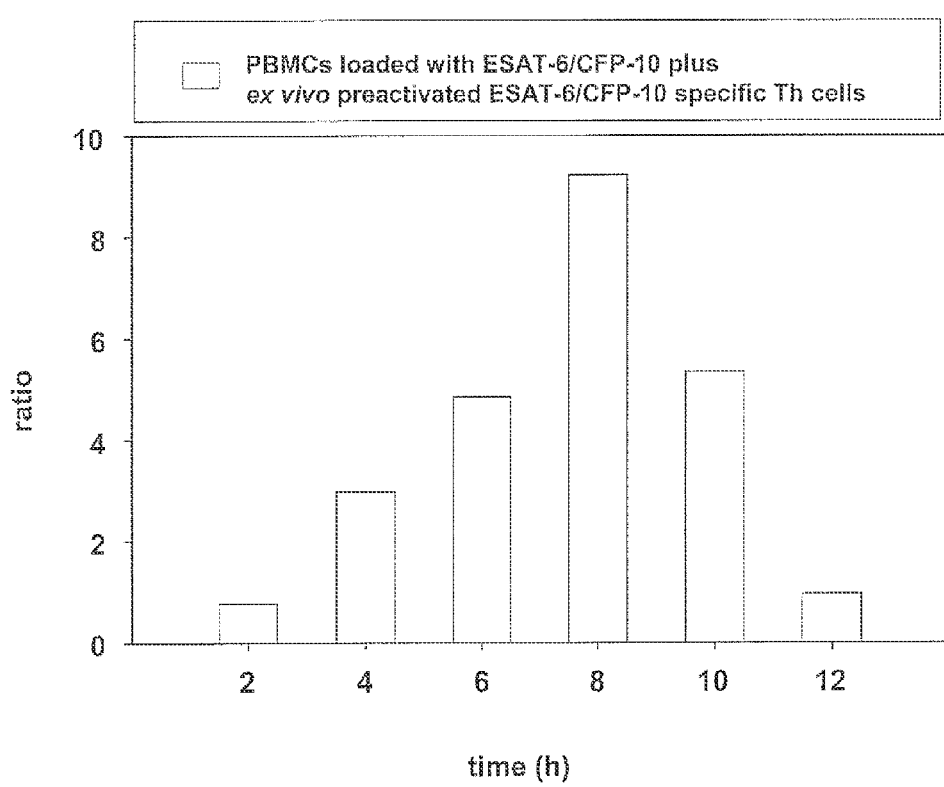
FIG. 3 shows in a diagram the relative increase of the 4-1BBL mRNA synthesis in ESAT-6/CFP-10 loaded PBMCs in comparison to unloaded PBMCs after coculture with autologous in vitro expanded preactivated ESAT-6/CFP-10 specific T helper cells, as determined by RT-qPCR. Freshly isolated PBMCs of a donor with a latent *M. tuberculosis* infection were incubated for 12 hours with 10 µg/ml ESAT-6/CFP-10 and subsequent thereto cocultivated in a ratio of 1:1 with ex vivo expanded autologous ESAT-6/CFP-10 specific T helper cells. A coculture of ESAT-6/CFP-10 specific Th cells and unloaded PBMCs served as negative control. At the indicated time points the stimulation samples were harvested and the relative increase in 4-1BBL mRNA expression was determined by RT-qPCR in specifically stimulated versus not stimulated cell cultures. The data of the RT-qPCR were analyzed according to the $2^{-\Delta\Delta Cq}$ method, wherein GAPDH served as reference gene and the unstimulated control as calibrator.

These analyses showed, that ESAT-6/CFP-10-specific, preactivated Th cells in cocultures with autologous, ESAT-6/CFP-10 protein-loaded PBMCs induce in comparison to unloaded PBMCs a measurably increased 4-1BBL mRNA production (FIG. 3).

Example 2

Correlation of Induction of 4-1BB Ligand mRNA Production in Cocultures of ESAT-6/CFP-10 Protein-Loaded PBMCs with the Number of Ex Vivo Expanded ESAT-6/CFP-10 Protein-Specific Th Cells ESAT-6/CFP-10 specific Th cells of subjects latently infected with *Mycobacterium tuberculosis* were expanded ex vivo as described in example 1 under item a) and were subsequently cocultured with freshly prepared autologous PBMCs as described in example 1 under item b). In this process the number of ESAT-6/CFP-10 specific Th cells cocultured with $1\times10^6$ PBMCs was titrated in a semi logarithmic concentration series (concentration steps: none, 117, 370, 1170, 3700, 11700, 37000, 117000 preactivated Th cells per $1\times10^6$ PBMCs). After 0; 0.5; 1; 2; 3; 4; 6; 8 and 10 hours of incubation $2\times10^5$ cells were removed, pelleted for 5 min at 300 g and the pellet was immediately frozen in liquid nitrogen. Until further use the cells were stored at –80° C. The total RNA was isolated according to the protocol in example 1 under c) and analysed in the RT-qPCR with respect to the production of 4-1BBL mRNA.

Figure 4:
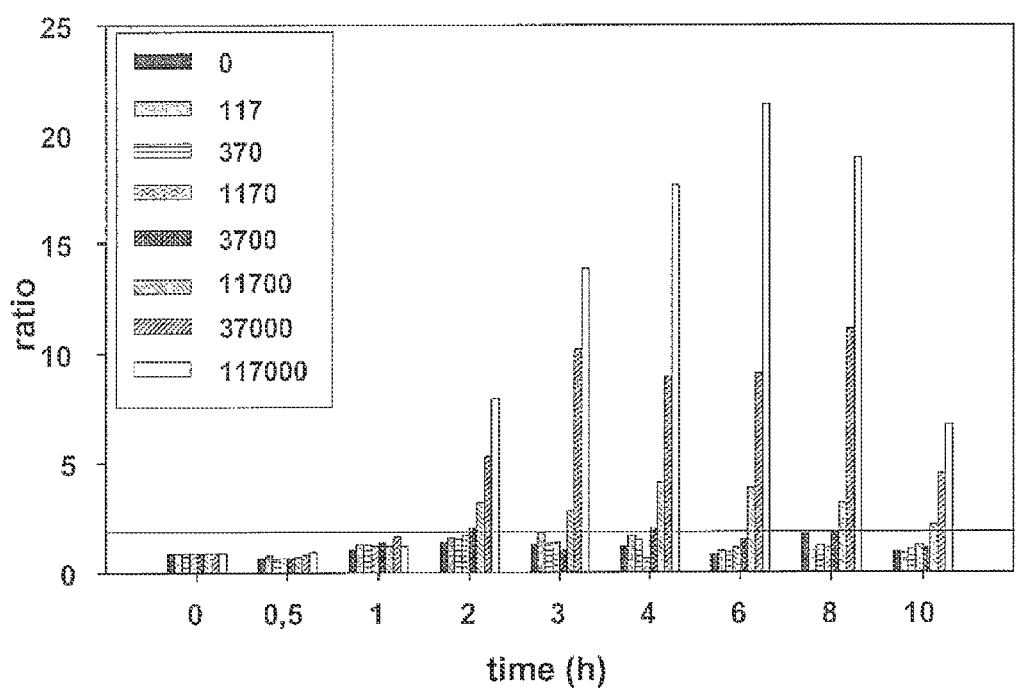
FIG. 4 shows in a diagram the correlation of the relative increase of the 4-1BBL mRNA production in ESAT-6/CFP-10 loaded PBMCs versus unloaded PBMCs with the number of antigen specific activated ESAT-6/CFP-10 specific T helper cells as determined by RT-qPCR. $1 \times 10^6$ freshly isolated PBMCs of a donor with a latent *M. tuberculosis* infection were cultivated with an increasing number of ex vivo expanded ESAT-6/CFP-10 specific T helper cells in presence of 10 µg/ml ESAT-6/CFP-10. Non-stimulated cocultures of autologous PBMCs and preactivated ESAT-6/CGP-10 specific Th cells served as control. At the indicated time points $2 \times 10^5$ cells were harvested and the relative increase of the 4-1BBL mRNA concentration in specifically stimulated cells in comparison to unstimulated cells was determined by RT-qPCR. The data of the RT-qPCR were analyzed according to the $2^{-\Delta\Delta Cq}$ method, wherein GAPDH served as reference gene and the unstimulated control as calibrator.

In these analyses a clear correlation between the number of preactivated ESAT-6/CFP-10 specific Th cells and the signal strength of the marker (increased production of 4-1BBL mRNA) was observable (FIG. 4).

Example 3

Induction of 4-1BBL as Well as of IFN-γ mRNA Production in Cocultures of Non-Stimulated and of with ESAT-6/CFP-10 Stimulated PBMCs and of Autologous Ex Vivo Preactivated *M. tuberculosis* ESAT-6/CFP-10 Specific Th Cells ESAT-6/CFP-10 specific Th cells of patients latently infected with *Mycobacterium tuberculosis* were expanded ex vivo as described in example 1 under item a) and were subsequently cocultured with freshly prepared autologous PBMCs as described in example 1 under item b). in this process 50,000 ex vivo preactivated ESAT-6/CFP-10 specific Th cells were cocultured with $1\times10^6$ PBMCs. In intervals of 2 hours over a period of from 0 to 32 hours $2\times10^5$ cells were removed in each case from the culture sample, pelleted for 5 min at 300×g and the pellet was immediately frozen in liquid nitrogen. Until further use the cells were stored at –80° C. The total RNA was isolated according to the protocol in example 1 under c) and analysed in the RT-qPCR with respect to the production of 4-1BBL mRNA.

In addition, the production of the mRNA of the cytokine IFN-γ, which is released by the T cell after antigen specific contact of APC with specific T cells, was likewise analysed as described in example 1 under c). For this purpose the following primer probe system was used, wherein GAPDH was likewise used as reference gene: IFN-γ forward primer GTGGAGACCATCAAGGAAGACAT, biomers, represented by SEQ ID NO:7; IFN-γ reverse primer GGCGACA-GTTCAGCCATCA, biomers, represented by SEQ ID NO:8; IFN-γ probe FAM-TTCATGTATTGCTTTGCGTTGGA-CATTCAA-TMR, represented by SEQ ID NO:9.

In persons latently infected with *M. tuberculosis M. tuberculosis* specific Th cells are present in the PBMC mixture, which partially exhibit also a specificity for ESAT-6/CFP-10. In contrast, activated ESAT-6/CFP-10 specific Th cells occur transiently during an acute disease and are only then found in the PBMC mixture. Adding by titration ex vivo preactivated ESAT-6/CFP-10-specific T h cells to PBMCs imitates an acute *M. tuberculosis* infection. These analyses show, that aside of an increase of the production the of 4-1BBL mRNA also a relative increase in IFN-γ mRNA is detectable in the coculture of ex vivo preactivated ESAT-6/CFP-10 specific Th cells with autologous PBMCs of a donor with latent tuberculosis (FIGS. 5A and 5B).

Example 4

Induction of 4-1BBL mRNA Production in Cocultures of ESAT-6/CFP-10 PBMC Loaded PBMCs with ESAT-6/CFP-10 Specific Activated Th-Cells or with Unspecifically Preactivated Th Cells For verification of the antigen specificity of the RTT method PBMCs of a donor with latent tuberculosis were stimulated in presence and absence of ESAT-6/CFP-10 protein with preactivated ESAT-6/CFP-10 specific activated Th-cells or with activated Th-cells not specific for ESAT-6/CFP-10 and the relative increase of 4-1BBL production in ESAT-6/CFP-10 stimulated in comparison to non stimulated cell cultures was determined at different time points by using the RT-qPCR technique. For this purpose Th cells were isolated as described in example 1 under item a) and thus obtained Th cells were cultured with commercially available T cell expander beads (Dynabeads, Invitrogen) in a ratio of 2:1 in R5 medium for 14 days in a humidified atmosphere at 37° C. and 5% $CO_2$. The activation of the T cells was determined by flow cytometry by monitoring the expression of CD40L. This analyses proved, that more than 40% of Th cells displayed after 14 days of stimulation with expander beads the CD40L on their surface (data not shown).

Subsequently $1\times10^6$ freshly prepared autologous PBMCs/ml were cocultured in presence and absence of 10 μg/ml ESAT-6/CFP-10 with in each case 0, 210, 6636 or 66360 ex vivo prestimulated ESAT-6/CFP-10 specific Th-cells (generated as described in example 1 under a)) or unspecifically activated Th cells (generated as in example 1 under b)). After 0; 0.5; 1; 2; 3; 4; 6 and 8 hours $2\times10^5$ cells were in each case removed from the cocultures and analysed as described in example 1 under c) in a RT-qPCR with respect to the production of 4-1BBL mRNA.

These experiments showed direct correlation between the number of preactivated ESAT-6/CFP-10 specific Th cells and the relative increase of 4-1BB1 expression in specifically stimulated in comparison to non-stimulated coculture samples. In contrast, in coculture samples with unspecifically preactivated Th cells a markedly reduced relative increase of the production of mRNA of 4-1BBL was observable (FIG. 6).

Example 5

Specifity of the Induction of 4-1BBL mRNA Production in Cocultures of PBMCs from Selected *M. tuberculosis*-, EBV- and CMV-Positive Donors and Ex Vivo Preactivated *M. Tuberculosis*-ESAT-6/CFP-10-, EBV BZLF1- or CMV-Pp 65-Specific Th Cells in Presence and Absence of ESAT-6/CFP-10, BZLF1 or pp 65

In a further experiment it was analysed, whether (i) the loading of PBMCs with *M. tuberculosis* ESAT-6/CFP-10, EBV BZLF1 and CMV pp 65 protein per se induces an unspecific activation of 4-1BBL mRNA and whether (ii) the induction of the RTT marker occurs due to an interaction of an APC with an activated Th cell in antigen specific manner. For this purpose by using isolated Th cells of EBV- and CMV-seropositive donors with a latent with *M. tuberculosis* infection ex vivo expanded and preactivated as described in example 1 under item a). 70000 of the ex vivo expanded T helper cells were subsequently cocultured in presence and absence of 10 µg/ml ESAT-6/CFP-10, BZLF-1 or pp 65 with in each case 1×10. After incubation for 0; 0.5; 1; 2; 3; 4; 6; 8 and 10 hours 2×10$^5$ cells were removed in each case from the cocultures, pelleted for 5 min at 300×g and the pellet immediately frozen in liquid nitrogen. Until further use the cells were stored at −80° C. The total RNA was isolated as described in the protocol according to example 1 under c) and analysed for production of the 4-1BBL mRNA by using the RT-qPCR technique.

These analyses verified, that the stimulation of APC containing PBMCs with various stimulator antigens does not elicit an unspecific activation of 4-1BBL mRNA. In addition these analyses verified that an increased production of 4-1BBL mRNA in APCs occurs exclusively after antigen specific contact of activated Th cells with APC. If *M. tuberculosis* specific Th cells were cocultured with autologous PBMCs, they elicited solely in presence of ESAT-6/CFP-10 an induction of 4-1BBL mRNA production, but not in presence of BZLF1 or pp 65 or in absence of an antigen (FIGS. 7 and 8a). In addition in vitro preactivated BZLF1- and pp 65-specific Th cells, respectively, induced only in those cultures of autologous PBMCs an increased production of 4-1BBL mRNA, which had been loaded with the respective target structures of the respective activated T cells (FIGS. 8b and 8c).

Furthermore, the executed analyses indicate, that the efficiency of the induction of 4-1BBL mRNA is inversely correlated with the number of antigen specific CTLs present in the PBMCs. In the blood of TB patients usually very few ESAT-6/CFP-10 specific CTLs may be found, while in CMV- and in particular in EBV-seropositive subjects a significant proportion, or a dominating proportion, respectively, of the existing memory T cells is attributable to the subpopulation of cytotoxic T cells (CTL). In cocultures of ESAT-6/CFP-10 specific preactivated Th cells with ESAT-6/CFP-10 loaded PBMCs the strongest activation of 4-1BBL was observable and in cocultures of BZLF1 specific preactivated Th cells with BZLF1 loaded PBMCs the lowest activation of 4-1BBL was observable. This finding may be explained by the lysis of signal giving APCs by specific CTL.

Example 6

Modulation of the Induction of 4-1BB Ligand mRNA Production in Cocultures of BZLF1 Loaded PBMCs and Ex Vivo Activated BZLF1-Specific Th Cells by Addition of a Blocking Anti-MHC Class 1 Antibody

*M. tuberculosis* infections are predominantly controlled by Th cells. In addition also cytotoxic T cells (CTL) play a role in combating the pathogen by recognizing and destroying cells infested by pathogens. In certain infections, i.e. an Epstein Barr virus (EBV) infection, CTLs represent the dominant T lymphocyte population. In case of the inventive method, based on the so-called reverse T cell technology, RTT, it is possible, that CTLs also recognize and destroy APCs loaded with pathogen specific target structures even before these express the marker of the APC, the RTT marker. Thereby the number of possible signal giving APCs and thus the sensitivity of the test is lowered. In order to investigate the influence of cytotoxic T cells on the sensitivity of the RTT method, coculture experiments with in vitro preactivated BZLF1 specific Th cells (generation as in example 1 under a)) with BZLF1 loaded autologous PBMCs were carried out in presence and absence of an MHC-I blocking antibody (10 µg/ml) (HLA ABC antibody, Cat. No. MCA81EL; clone W6/32 AbD Serotec) as described in example 1 under b). Due to the binding of the antibody to an MHC-I molecule on antigen presenting cells their recognition by CTLs is prevented, with the result that no killing of protein loaded APCs occurs. 1×10$^6$ cells/ml were cocultured in BZM, wherein per 1×10$^6$ PBMCs 70000 BZLF1-specific preactivated Th cells were used. At the time points 0, 1, 2, 3, 4, 6, 8 and 10 h 2×10$^5$ cells per sample were in each case removed, pelleted and immediately frozen in liquid nitrogen. Until further processing the samples were stored at −80 C. Then the content of 4-1BBL mRNA, as described in example 1 under c), was analysed in a RT-qPCR.

By using a MHC class 1 blocking antibody it was possible in these experiments to significantly increase the induction of 4-1BBL mRNA in the coculture of BZLF1-specific Th cells with BZLF1-loaded PBMCs (FIG. 9).

Example 7

Analysis of the Specific Induction of 4-1BB Ligand mRNA Production in PBMCs of Patients with Active and Latent Tuberculosis, as Well as of Healthy Donors for Indirect Detection of Activated Th Cells In order to elucidate, whether the inventive method, RTT method, is useful for identification of patients with active tuberculosis and their discrimination from patients with latent tuberculosis and healthy donors, blood was removed in a heparinized syringe from in each case three (i) healthy donors not infected with *M. tuberculosis* (p012, 010, p008), (ii) healthy donors with a latent tuberculosis (p009, p006, p005), (iii) donors, which had been treated due to an active tuberculosis in the last 6 months prior to the analysis with medicaments (p013, p014, p003) and (iv) donors with an active tuberculosis prior to or shortly after the start of a causal therapy (p001, p004, p007) and PBMCs were freshly isolated therefrom. Then in each case 1×10$^6$ cells/mL were incubated with 10 µg/mL ESAT-6/CFP-10 in humidified atmosphere at 37° C. and 5% CO$_2$. In addition PBMCs of selected donors were incubated with the control antigens, HIV p24 (capsid antigen) (healthy: p008; latent: p005 and p006; treated: p003; active: p007 and p001) or bovine serum albumin (p001) or as a further negative control in absence of any antigen. In each case $2\times10^5$ cells were removed after 0.5; 1; 2; 3; 4; 6; 8 and 10 hours of incubation, pelleted and immediately frozen in liquid nitrogen. Until further processing the cells were stored at −80° C. As described in example 1 under c), then the content of 4-1BBL mRNA was analysed in a RT-qPCR.

It was shown, that the stimulation with ESAT-6/CFP-10 in PBMCs of healthy donors did not lead to an induction of 4-1BBL mRNA (FIG. 10a). Likewise no induction of 4-1BBL mRNA was measurable in PBMCs of subjects latently infected with M. tuberculosis (FIG. 10b) or in subjects, which had been treated with medicaments 6 months prior to the analysis due to an active tuberculosis (FIG. 10c). Merely in PBMCs of acutely diseased subjects prior or shortly after the start of a causal therapy it was possible to observe after stimulation with ESAT-6/CFP-10 a significantly increased induction of 4-1BBL mRNA in specifically stimulated in comparison to unstimulated cell cultures (FIG. 10d). The stimulation of the PBMCs with the irrelevant antigens BSA and p24 did likewise not result in an increased induction of 4-1BBL mRNA (FIG. 10e).

Example 8

Induction of 4-1BBL mRNA Production in PBMCs of Donors with Acute and Latent Tuberculosis as Well as of Healthy Subjects with Tuberculin PPD In order to investigate, whether the induction of 4-1BBL mRNA in PBMCs of acute tuberculosis patients can be increased by using a broader antigen spectrum, blood was removed in a heparinized syringe in each case from a patient with an active and a latent tuberculosis, as well as from a healthy donor, and PBMCs were freshly isolated therefrom. Then $1\times10^6$ cells/mL were either incubated with 10 μg/mL ESAT-6/CFP-10 or tuberculin PPD (Statens Serum Institut, Denmark) in humidified atmosphere at 37° C. and 5% $CO_2$. In addition aliquots of the PBMCs were incubated as negative control without antigens and as positive control for the inducibility of 4-1BBL mRNA production with in each case 1 μg/mL phorbol-12-myrestate-13-acetate (PMA) (Sigma Aldrich) and ionomycin (Sigma Aldrich). $2\times10^5$ cells were removed after 0, 2, 4, 6, 8, and 10 hours of incubation, pelleted and immediately frozen in liquid nitrogen. Until further processing the cells were stored at −80° C. As described in the example 1 under c), then the content of 4-1BBL mRNA was analysed in a RT-qPCR.

It could be shown, that the stimulation with tuberculin PPD elicited a many fold higher induction of 4-1BBL mRNA production in PBMCs of the patient with an acute tuberculosis than ESAT-6/CFP-10 (FIG. 11a, upper image). In parallel, no significantly increased induction of 4-1BBL mRNA production was observable in PBMCs of the latently infected and of the healthy subject after stimulation with tuberculin PPD as well as with ESAT-6/CFP-10 (FIGS. 11b and 11c upper images). In addition, in with PMA/ionomycin stimulated aliquots of PBMC of all three donors in comparison to unstimulated aliquots of PBMC a significantly increased production of 4-1BBL mRNA was observable, thus verifying the functionality of the PBMC for the production of this RTT marker (FIGS. 11a-c, lower images).

Example 9

Time Course of the Induction of 4-1BB Ligand Expression in PBMCs of a Healthy Donor after Stimulation with the Combinations of PMA/Ionomycin or PGE2/Anti-CD40

For the identification of positive controls for the inventive RTT method for detection of activated T cells it was investigated, whether, and to what intensity, the combinations of PMA/ionomycin or PGE2/anti-CD40 do elicit an unspecific induction of the 4-1BBL mRNA expression. For this purpose $1\times10^6$ PBMC/mL of a healthy donor were incubated in each case with 1 μg/mL PMA and ionomycin or a combination of 5 μg/mL $PGE_2$ (Alexis Biochemicals) and a 2 μg/mL CD40-antibody (LEAF-anti CD40; Biozol). As negative control served non-stimulated PBMCs. $5\times10^5$ cells were removed after 0, 2, 4, 6 and 8 hours of incubation, pelleted and immediately frozen in liquid nitrogen. Until further use the cells were stored at −80° C. As described in example 1 under c), then the content of 4-1BBL mRNA was analysed in a RT-qPCR.

Figure 12A:
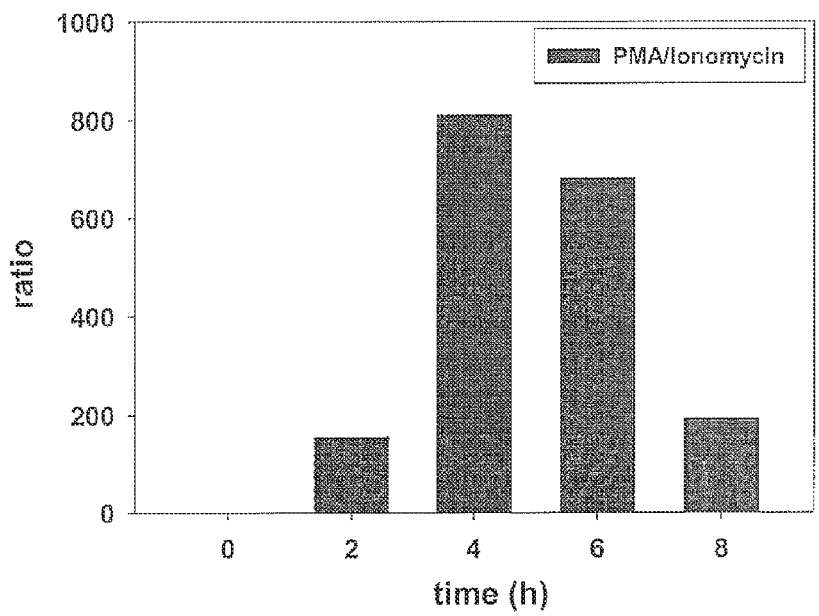
FIG. 12 shows in (A) and (B) in diagrams the unspecific induction of 4-1BBL mRNA production in PBMCs of a healthy volunteer after stimulation with 1 µg/ml PMA/Ionomycin in (A), or PGE2/α-CD40 in (B), in comparison to the unstimulated control, as determined by RT-qPCR. Freshly isolated PBMCs of a healthy volunteer were incubated with in each case 1 µg/ml PMA/Ionomycin in (A) or with 5 µg/mL PGE$_2$ and 2 µg/mL α-CD40 (B). At the indicated time points $0.5\times10^6$ cells were removed, peletted and stored at −80° C. until further use. Total RNA was isolated from the cells and transcribed into cDNA. Then the amount of 4-1BBL cDNA was determined in a RT-qPCR. Analysis was done according to the $2^{-\Delta\Delta C_q}$ method by using GAPDH as reference gene and the unstimulated control as calibrator.
Figure 12B:
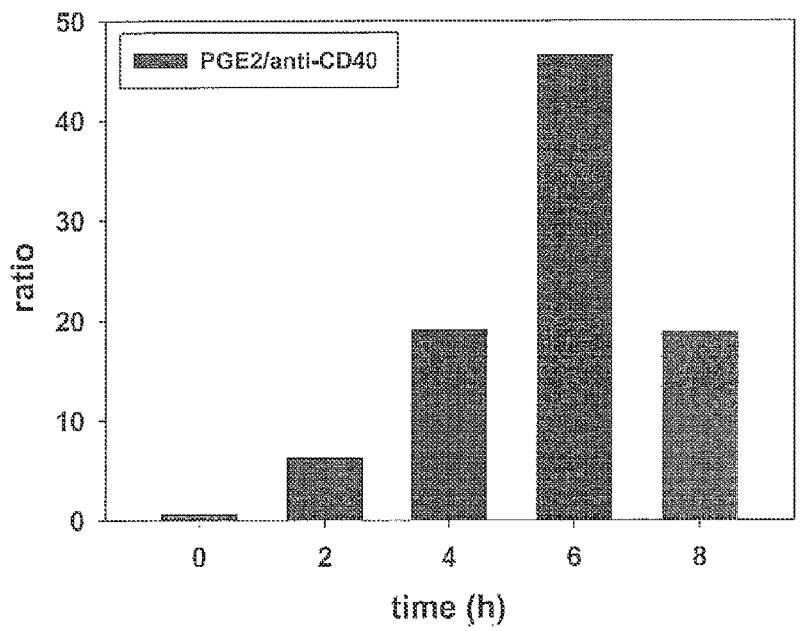

These analyses showed, that PMA and ionomycin (FIG. 12a) represent a significantly more efficient unspecific inducer of 4-1BBL mRNA production than the combination of $PGE_2$ and the CD40-antibody (FIG. 12b).

Example 10

Comparative Determination of the Relative Induction of 4-1BBL mRNA Production in Non-Stimulated and in with ESAT-6/CFP-10 Stimulated Cocultures of In Vitro Preactivated M. Tuberculosis-Specific Th Cells and Autologous PBMCs Using Different Reference Genes For the identification of suitable reference genes for the inventive RTT method the reference genes GAPDH, huP0 and PBGD were amplified in the cDNA samples described in example 3, by using the respective primer/probe system, for normalising the amount of 4-1BBL mRNA. For this purpose the primer/probe systems for the amplification of the genes were used according to the RT-qPCR conditions described in example 1 under c).

For this purpose the following primer/probe system was used:
huP0 forward primer GTGGTGCTGATGGGCAAGA, biomers, represented by SEQ ID NO:10; huP0 reverse primer GCAGCAGTTTCTCCAGAGCTG, biomers, represented by SEQ ID NO:11; huP0 probe FAM-ACCATGAT-GCGCAAGGCCATCC-TMR, TIB Molbiol, represented by SEQ ID NO:12; PBGD forward primer CCAGCTCCCT-GCGAAGAG, biomers, represented by SEQ ID NO:13; PBGD reverse primer CACTGAACTCCTGCTGCTCG, biomers, represented by SEQ ID NO:14; PBGD probe FAM-CCCAGCTGCAGAGAAAGTTCCCGC-TMR, TIB Molbiol, represented by SEQ ID NO:15. The analysis was done according to the $2^{-\Delta\Delta C_q}$ method by using GAPDH, huP0 and PBGD as reference gene and the unstimulated control as calibrator.

Figure 13:
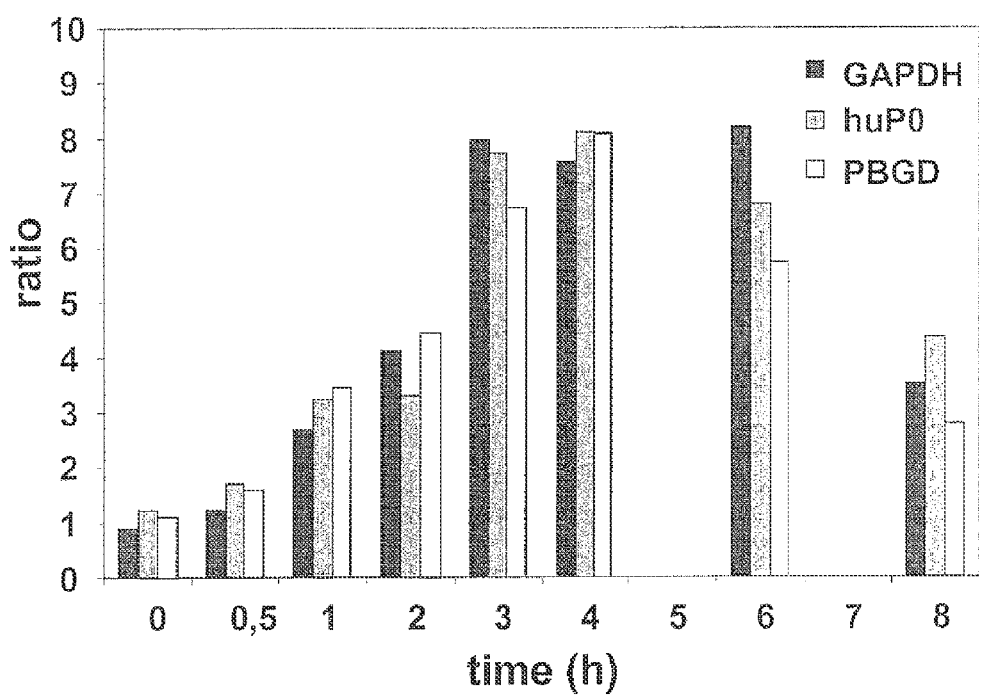
FIG. 13 shows in a diagram the influence of various reference genes on the determined relative increase of 4-1BBL mRNA production in ESAT-6/CFP-10 stimulated versus unstimulated cocultures of ESAT-6/CFP-10 specific activated T cells and autologous PBMCs of a donor with a persisting tuberculosis as determined by RT-qPCR. Freshly isolated PBMCs of a donor with a persistent tuberculosis were incubated with preactivated ESAT-6/CFP-10 specific Th cells in presence and absence of 10 µg/ml ESAT-6/CFP-10 protein. At the indicated time points $0.5\times10^6$ cells were removed, peletted and stored at −80° C. until further use. Total RNA was isolated from the cells and transcribed into cDNA. Then, the content of 4-1BBL cDNA was determined by RT-qPCR. Analysis was done according to the $2^{-\Delta\Delta C_q}$ method by using GAPDH, hu P0 and PBGD as reference gene and the unstimulated control as calibrator.

These analyses revealed, that the content of 4-1BBL mRNA can be normalized with all three reference genes without significant influence on the final result (FIG. 13). Although differences in the strength of induction of 4-1BBL mRNA were observable when normalizing with the three reference genes, the tendency was comparable.

Example 11

Determination of 4-1BB Ligand Expression in Cocultures of ESAT-6/CFP-10-Loaded PBMCs and of Ex Vivo Expanded ESAT6/CFP-10-Specific Th Cells by Flow Cytometry In vitro expanded activated ESAT-6/CFP-10 specific Th cells (generation as in example 1 under a)) were mixed 1:1 with autologous PBMCs and cocultured in presence and absence of recombinant ESAT-6/CFP-10 in a concentration of $1\times10^6$ cells/ml in R5 for 28 h. During the last 26 h the protein secretion was inhibited by brefeldin A. Then the protein expression of 4-1BBL in B cells was intracellularly labelled according to the protocol in example 1 under a) and then determined by flow cytometry. For the surface staining 5 µl of anti-CD19 R-pycoerythrin cyanine 7 (PeCy7) (BD) and for the intracellular staining of 4-1BBL 20 µl anti-4-1BBL PE (BD) were used.

Figure 2:
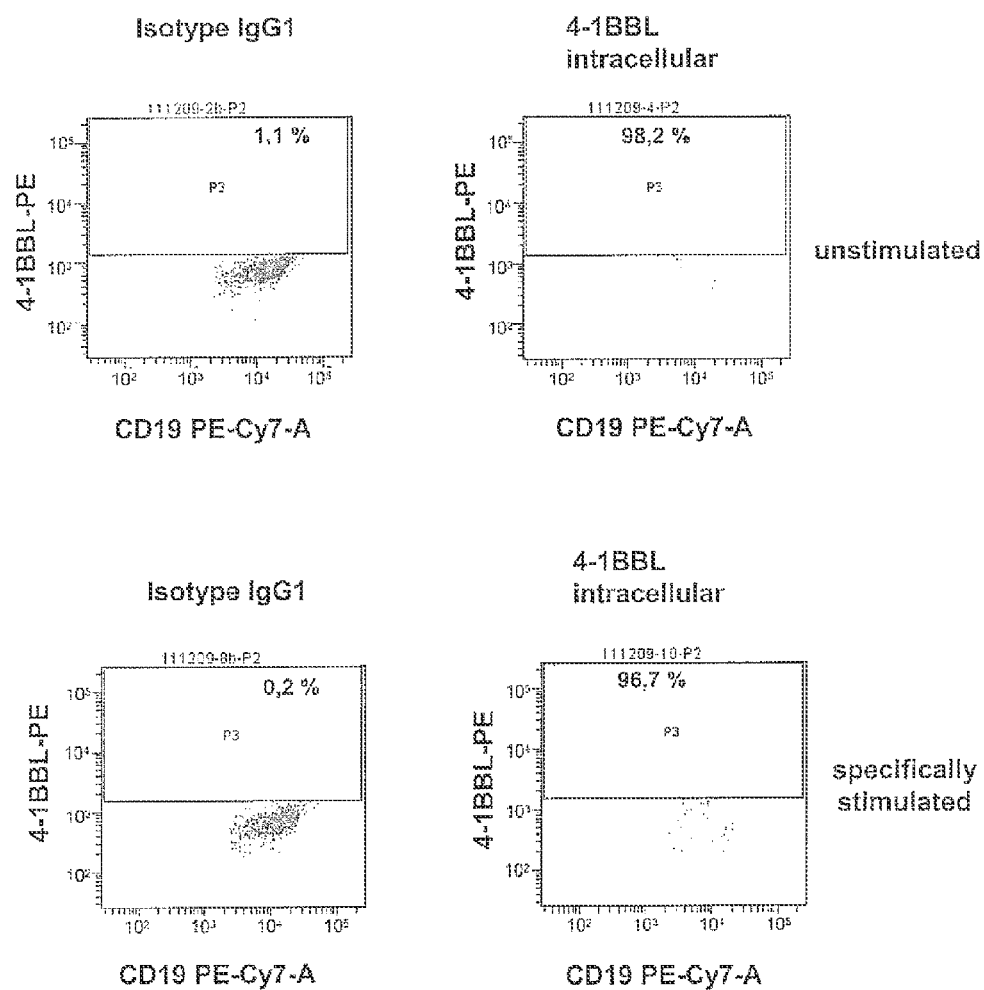
FIG. 2 shows in a dot blot graph the number of B cells with intracellularly detectable 4-1BBL protein in cocultures of ex vivo preactivated ESAT-6/CFP-10 specific T cells and PBMCs of a blood donor with latent tuberculosis, wherein the cocultures were stimulated or not stimulated with ESAT-6/CFP-10 fusion protein. In vitro expanded preactivated ESAT-6/CFP-10 specific T helper cells were mixed 1:1 with autologous PBMCs and were cocultured in presence or absence of 10 μg/ml ESAT-6/CFP-10 for 18 h. During the last 16 h the protein secretion was inhibited with brefeldin A. The detection of intracellular 4-1BBL in B cells was done by flow cytometry.

These analyses showed, that already unstimulated B cells exhibit a very high content of intracellularly existing 4-1BBL; thus no further induction of 4-1BBL expression on the protein level can be detected after stimulation with ESAT-6/CFP-10 (FIG. 2). These analyses prove, that the detection of T cell induced maturation processes on protein level is due to the variable and partially very high content of the RTT marker only possible with limitations when using flow cyctometry or the ELISA and ELISpot technique.

Example 12

Identification of Reference Genes for the RTT Method for Normalising the RT-qPCR. Variations in the Expression Levels in Various Reaction Mixtures, which are not Caused by the Biological Change in the Expression in the Cell, Shall Hereby be Corrected For the identification of reference genes, which are suitable in the RTT method for the analysis of clinical samples, PBMC samples of various subject groups were stimulated under three different conditions and the RT-qPCR results for the reference genes were compared with the results of the respective unstimulated sample. Sodium heparine blood samples of two patients actively infected with TB, of one latently infected TB patient, as well as of one healthy and one healthy BCG vaccinated subject were processed. For this purpose the PBMCs were isolated as indicated in example 1 under a). Then $6\times10^6$ PBMCs per 6 ml sample were stimulated in B cell medium. The stimulations were done either with ESAT6/CFP10 (10 µg/ml), tuberculin PPD (10 µg/ml) or unspecificially with PMA/ionomycin (in each case 1 µg/ml) over a period of time of 6 h in humidified atmosphere at 37° C. and 5% $CO_2$. After incubation the cells were pelleted at 300×g for 10 min, the supernatant discarded, the pellet lysed in RLT buffer (QIAGEN) with 1% β-mercaptoethanol and immediately frozen in liquid nitrogen. The RNA was isolated with the RNeasy Mini Kit (QIAGEN) including a DNase digest on the column according to the manufacturer's instructions. The cDNA synthesis was carried out with the QuantiTect Reverse Transcription Kit of QIAGEN. The qPCR was carried out with the Custom TaqMan® Gene Expression Array 96-Well Fast Plates (Applied Biosystems) and the TaqMan Fast Universal Master Mix (Applied Biosystems) on a ABI StepOnePlus Real Time PCR system (Applied Biosystems) according to the manufacturer's instructions.

The expression level of a well suited reference gene for a RT-qPCR should under all applied experimental conditions and under the stimulations contemplated therein remain constant. In addition, the expression level of the reference gene should correspond to the expression level of the target gene. Likewise, the qPCR efficiency should be similar to the one of the target genes. For all five samples the results were compared and analysed.

Figure 14:
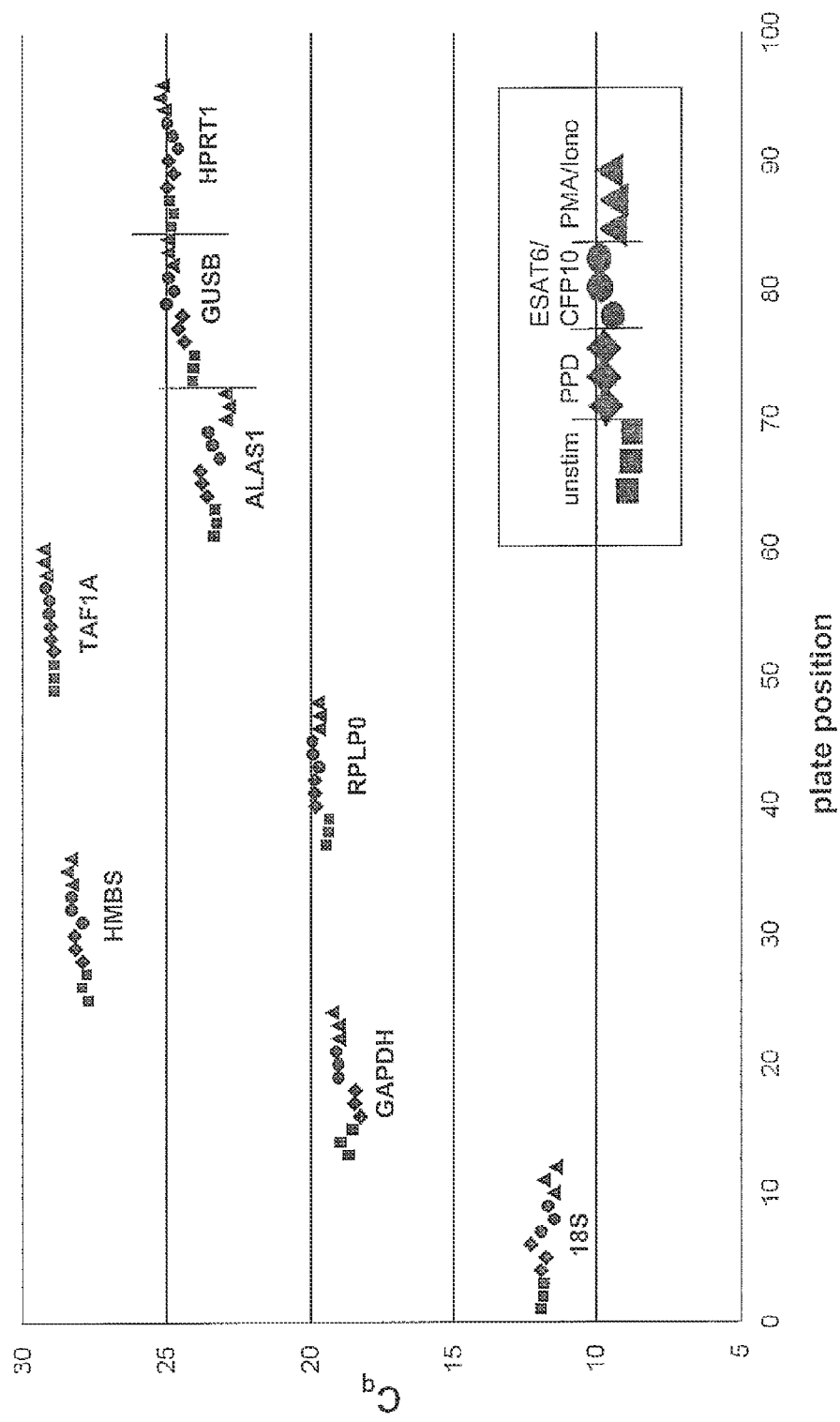
FIG. 14 shows an amplification plot of a real time PCR for the identification of a suitable reference gene for the RTT method. On the y-axis the quantification cycles ($C_q$) for 7 potential reference genes under 4 stimulation conditions (unstimulated, tuberculin (PPD), ESAT6/CFP10, PMA/Ionomycin) are exemplarily illustrated in triplicates for one sample. The enlarged section shows the sequence of stimulation conditions for each of the 12 data points. On the x-axis the plate position on the 96-well plate is indicated. 18S: eukaryotic 18S ribosomal RNA; ALAS: aminolevulinate, delta-, synthase 1; GAPDH: glyceraldehyde-3-phosphate dehydrogenase; GUSB: glucuronidase, beta; HMBS: hydroxymethylbilane synthase; HPRT1: hypoxanthine phosphoribosyltransferase 1; Iono: Ionomycin; PMA: Phorbol-12-myristat-13-acetat; PPD: Tuberkulin PPD; RPLPO: ribosomal protein, large, P0; TAF1A: TATA box binding protein (TBP)-associated factor, RNA polymerase I, A, 48 kDa; unstim: unstimulated.

The result is depicted in FIG. 14. The expression of the RTT marker gene TNFSF9 and IFNG for the various stimulation conditions was detected between $C_q$ 23 and $C_q$ 30 (not shown). The genes TAF1A and HMBS are suitable as reference genes for the RTT marker RNA of 4-1BBL—also termed TNFSF9—and IFN-γ—also termed IFNG due to the constant expression for all stimulations conditions as well as due to the expression level at $C_q$ 28-$C_q$ 29 and due to the similar efficiency of the RT-qPCR in comparison to the one of the target genes (not shown). For alternative markers with higher expression HPRT1 or RPLP0 may be considered as suitable reference genes.

Altogether thus several suitable reference genes could be identified in these analyses, whose expression level remains constant in all experimental conditions. Depending on the expression level of the RTT marker gene TAF1A, HMBS can be used as reference gene for low expression, HPRT1 for a medium expression or RPLP0 for a high expression. For the marker TNFSF9 and IFNG TAF1A is suitable as reference gene.

Example 13

Figure 15:
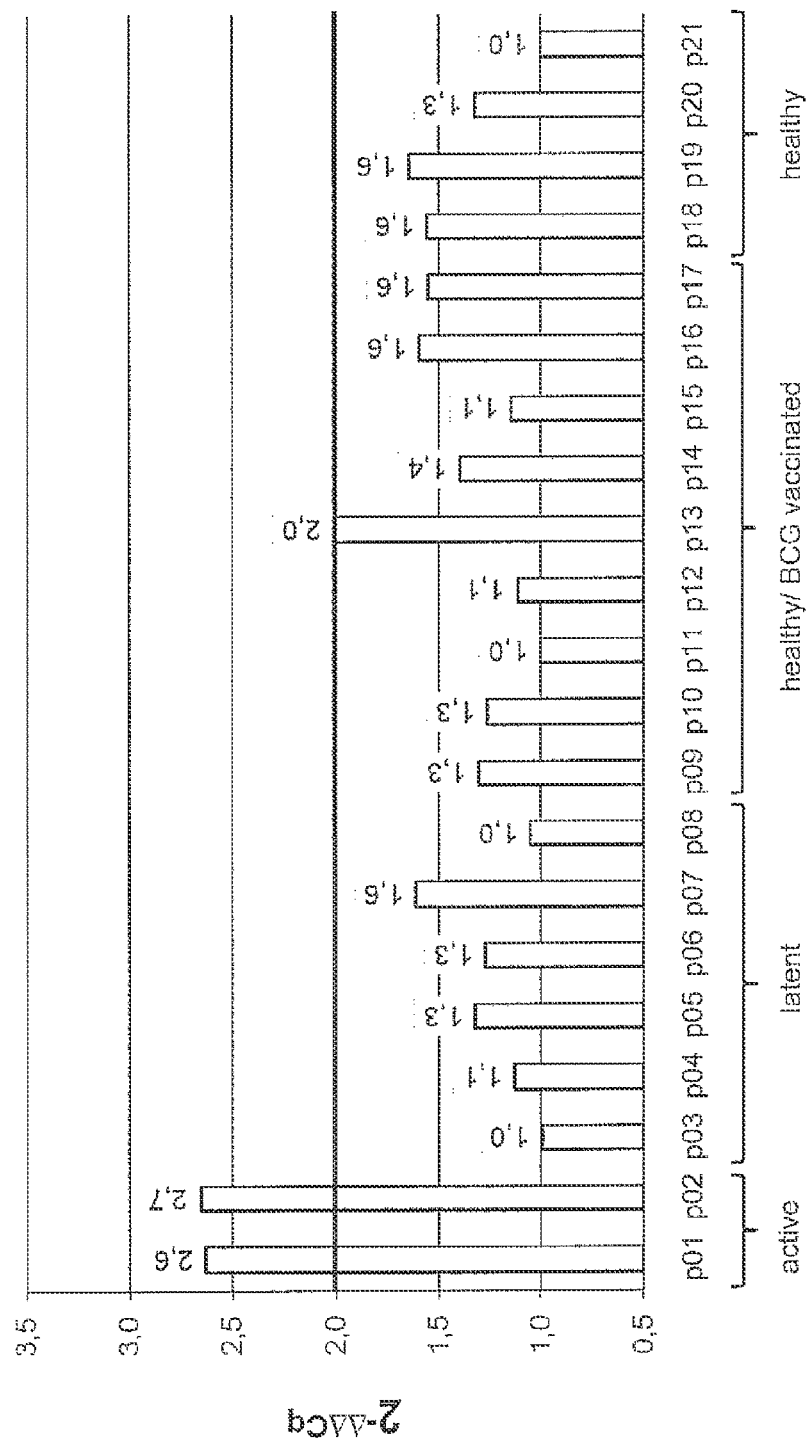
FIG. 15 shows the increase of the relative expression of the RTT marker gene 4-1BBL—also termed TNFSF9—in samples of actively or latently infected TB patients as well as of healthy BCG vaccinated or healthy non vaccinated volunteers after stimulation with tuberculin PPD in comparison to the respective unstimulated samples. The values were normalized against the reference gene TAF1A ($2^{-\Delta\Delta C_q}$). Per sample $5\times10^6$ PBMCs were stimulated in B cell medium with 10 µg/ml tuberculin PPD. Active: patients with an active tuberculosis; latent: patients with a latent tuberculosis; BCG: *Bacillus* Calmette-Guérin, attenuated live vaccine against tuberculosis.

Determination of the 4-1BBL—Also Termed TNFSF9—Expression in Tuberculin PPD Stimulated PBMCs in Comparison to Non-Stimulated Samples from Various Subjects for Determination of Background Expression of the RTT Marker and of a Threshold Value for the Discrimination Between Patients With an Active TB Infection and Healthy Persons The inventive RTT method was carried out on blood samples of 21 subjects in order to obtain information about the average background expression of the RTT marker 4-1BBL—also termed TNFSF9—in healthy subjects and in patients with a latent TB. For this purpose the PBMCs were isolated as indicated in example 1 under a). Per sample $5\times10^6$ PBMCs were incubated in B cell medium in presence and absence of 10 µg/ml tuberculin PPD for a period of time of 6 h in humidified atmosphere at 37° C. and 5% $CO_2$. The stimulations were done in duplicate and processed independently. After incubation the cells were pelleted, lysed in RLT buffer (QIAGEN GmbH, Hilden, Germany) with 40 mM DTT and the lysate was immediately frozen in liquid nitrogen. The RNA was isolated with the RNeasy Mini Kit of QIAGEN including a DNase digest on the column according to the manufacturer's instructions. cDNA syntheses were done with in each case 1 µg RNA with the QuantiTect Reverse Transcription Kit (QIAGEN) according to the manufacturer's instructions. The qPCR was carried out with 1 µl cDNA in 10 µl total reaction volume by using the TaqMan® Fast Universal PCR Master Mix of Applied Biosystems. The master mix had the following composition: 300 nM TNFSF9 forward primer GAGGGTC-CCGAGCTTTCG, represented by SEQ ID NO:1; 300 nM TNFSF9 reverse primer GCCCATCGATCAGCAGAAC, represented by SEQ ID NO:2; 200 nM TNFSF9 probe FAM-CCACCAGCTGCGCAAACATGC-TMR, represented by SEQ ID NO:3; 1× TaqMan® Fast Universal PCR Master Mix, 1× TaqMan® Gene Expression Assay TAF1A VIC dye labelled MGB Probe (primer limited) of Applied Biosystems. The temperature profile of the qPCR comprised 20 s denaturing at 95° C. and then 40 cycles consisting of 3 s at 95° C. and 30 s at 60° C. The qPCR was performed on the StepOnePlus Real-Time PCR system (Applied Biosystems). The mean values of the results from in each case two independent stimulations of the comparative $C_q$ analysis ($2^{-\Delta\Delta C_q}$) for the 21 samples are depicted in FIG. 15. These analyses showed, that the relative increase in expression of the RTT marker TNFSF9 after stimulation was for subjects with a latent TB, healthy individuals and BCG vaccinated healthy individuals below or at most 2-fold, while actively infected TB patients showed an increase in expression of more than 2-fold. Thus, a preliminary threshold value of $2^{-\Delta\Delta C_q}=2.0$ could be determined. A differentiation between actively infected TB patients and healthy individuals or subjects with a latent TB, respectively, is thus possible with the RTT method.

Example 14

Improvement of the Expression of IFN-γ—Also Termed IFNG—by Using Alternative, Partially Synthetic Serum Free Media In order to investigate, whether the IFN-γ—also termed IFNG—signal may be increased by using alternative cell culture media, several in part synthetic media were tested. The conventionally used B cell medium contains IL-4, which may lead to inhibition of the IFNG signal. In addition the medium contains self-made AB serum, which means that standard conditions, i.e. constant conditions without variations in quality, can not be optimally adhered to. With blood samples of three subjects with a latent TB and of three healthy individuals the inventive RTT method was performed. For this purpose the PBMCs were isolated as indicated in example 1 under a). Per sample $5\times10^6$ PBMCs were incubated in 2.5 ml of the various cell culture media in presence and absence, respectively, of 10 µg/ml tuberculin PPD for 6 h in humidified atmosphere at 37° C. and 5% $CO_2$. The following media were tested: B cell medium (BZM+), B-cell medium without IL-4 (BZM-), serum free UltraCULTURE™ medium (Ultra) of LONZA and AIM V medium (AIMV) of Invitrogen. Cell lysis, RNA extraction, cDNA synthesis and qPCR were performed as described in example 13. The increase in expression was assessed for IFNG and 4-1BBL—also termed TNFSF9 (see FIG. 16 and FIG. 17). The master mix for IFNG had the following composition: 300 nM IFNG forward primer GTGGAGAC-CATCAAGGAAGACAT (biomers), represented by SEQ ID NO:7; 300 nM IFNG reverse primer GGCGACAGTTCA-GCCATCA (biomers), represented by SEQ ID NO:8; 200 nM IFNG probe FAM-TTCATGTATTGCTTTGCGTTG-GACATTCAA-TMR (TIB MOLBIOL), represented by SEQ ID NO:9; 1× TaqMan® Fast Universal PCR Master Mix, 1× TaqMan® Gene Expression Assay TAF1A VIC dye labelled MGB probe (primer limited) of Applied Biosystems. The master mix for TNFSF9 had the following composition: 300 nM TNFSF9 forward primer GAGGGTC-CCGAGCTTTCG (biomers), represented by SEQ ID NO:1; 300 nM TNFSF9 reverse primer GCCCATCGATCAGCA-GAAC (biomers), represented by SEQ ID NO:2; 200 nM TNFSF9 probe FAM-CCACCAGCTGCGCAAACATGC-TMR (TIB MOLBIOL), represented by SEQ ID NO:3; 1× TaqMan® Fast Universal PCR Master Mix, 1× TaqMan® Gene Expression Assay TAF1A VIC dye labelled MGB probe (primer limited) of Applied Biosystems. The temperature profile of the qPCR comprised 20 s denaturation at 95° C. and then 40 cycles consisting of 3 s at 95° C. and 30 s at 60° C. The qPCR was performed on a StepOnePlus Real-Time PCR system (Applied Biosystems).

Figure 16:
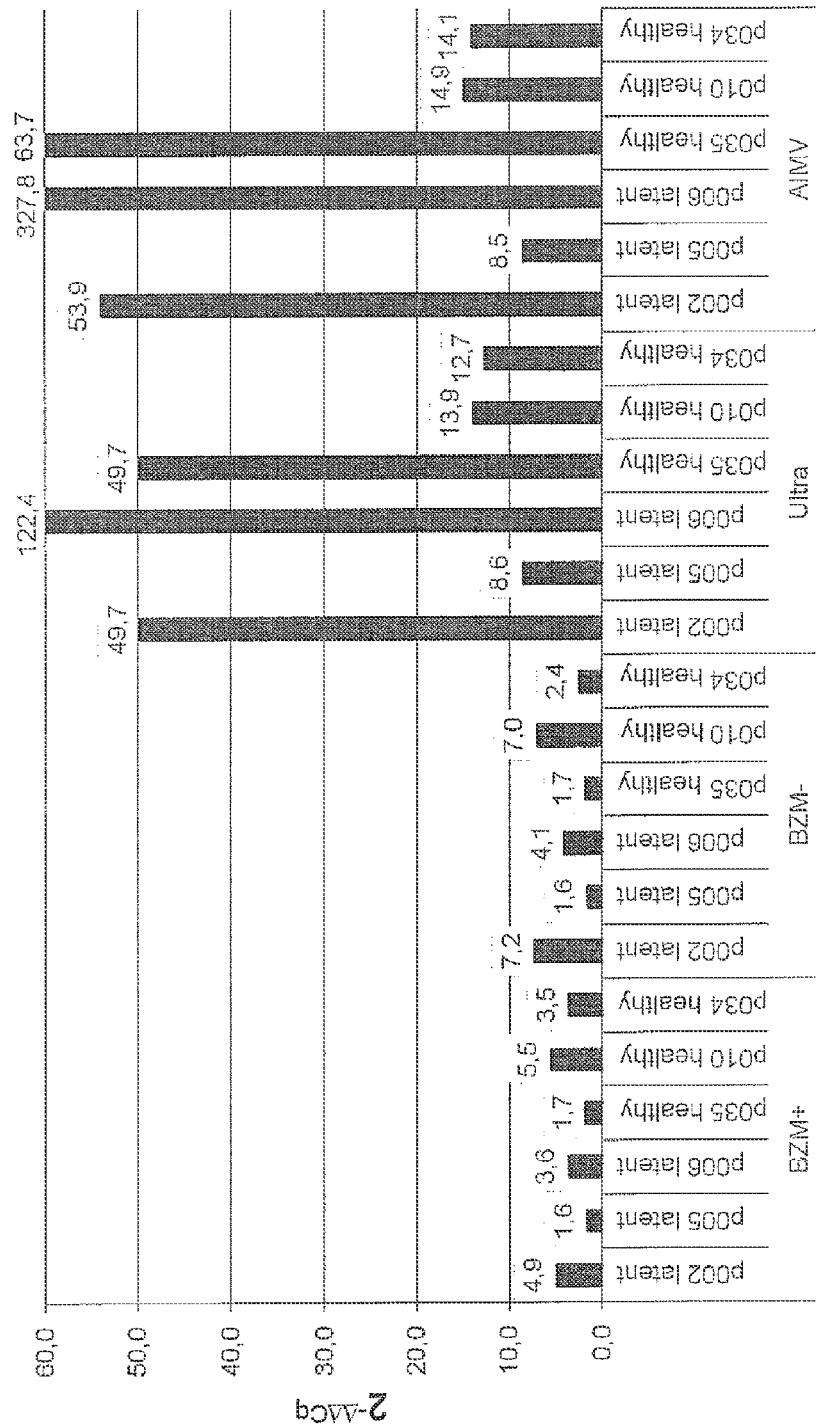
FIG. 16 shows the influence of different cell culture media on the relative increase of the expression signals of IFN-γ—also termed IFNG—in PBMCs of patients with a latent TB and healthy volunteers after stimulation with tuberculin PPD in comparison to unstimulated samples and normalisation against TAF1A. B cell medium (BZM+), B cell medium without IL-4 (BZM-), serumfree UltraCULTURE™ medium (Ultra) of LONZA and AIM V medium (AIMV) of Invitrogen were used.
Figure 17:
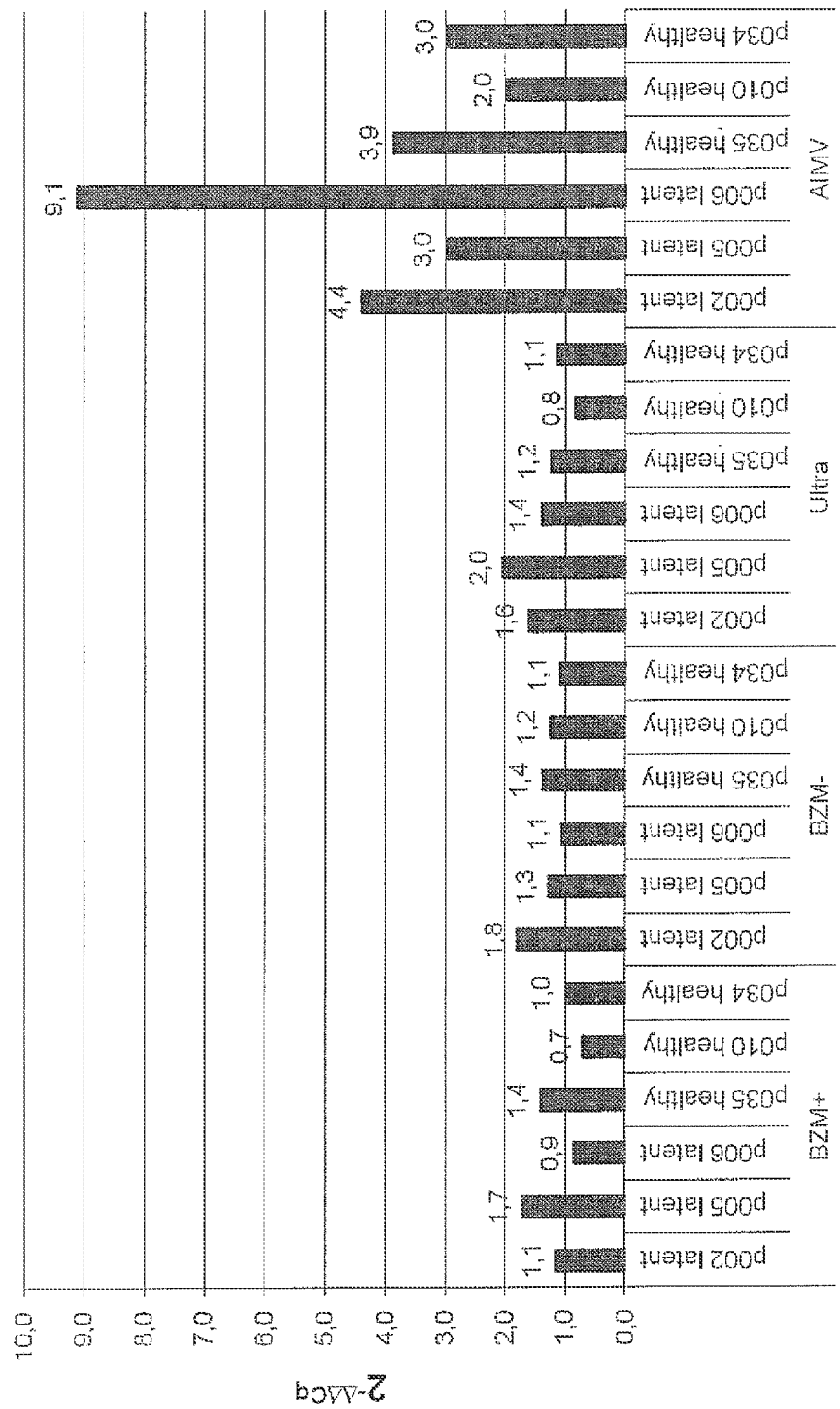
FIG. 17 shows the influence of different cell culture media on the relative increase of the expression signal of 4-1BBL—also termed TNFSF9—in PBMCs of patients with a latent TB and healthy volunteers after stimulation with tuberculin PPD in comparison to unstimulated samples and normalization against TAF1A. B cell medium (BZM+), B cell medium without IL-4 (BZM-), serum-free UltraCULTURE™ medium (Ultra) of LONZA and AIM V medium (AIMV) of invitrogen were used.

The relative increase in IFNG expression ($2^{-\Delta\Delta C_q}$) was in UltraCULTURE™ as well as in AIM V medium after stimulation significantly stronger than in conventional BZM+. Removal of IL-4 from the B cell medium (BZM-) did not lead to a signal enhancement (FIG. 16). For the stimulation in UltraCULTURE™ a relative increase in expression of TNFSF9 was not detectable in samples of patients with a latent TB and of healthy subjects. In contrast, the stimulation in AIM V medium resulted in comparison to the B cell medium and the UltraCULTURE™ medium, respectively, in a strong unspecific induction of TNFSF9 RNA expression (FIG. 17). These analyses show, that the choice of medium may have strong influence on the relative expression of RTT marker genes. The use of serum free UltraCULTURE™ medium of LONZA led to a significant enhancement of the IFNG signal in samples of subjects with a latent TB at constant background expression of the RTT marker gene TNFSF9.

Example 15

Figure 18:
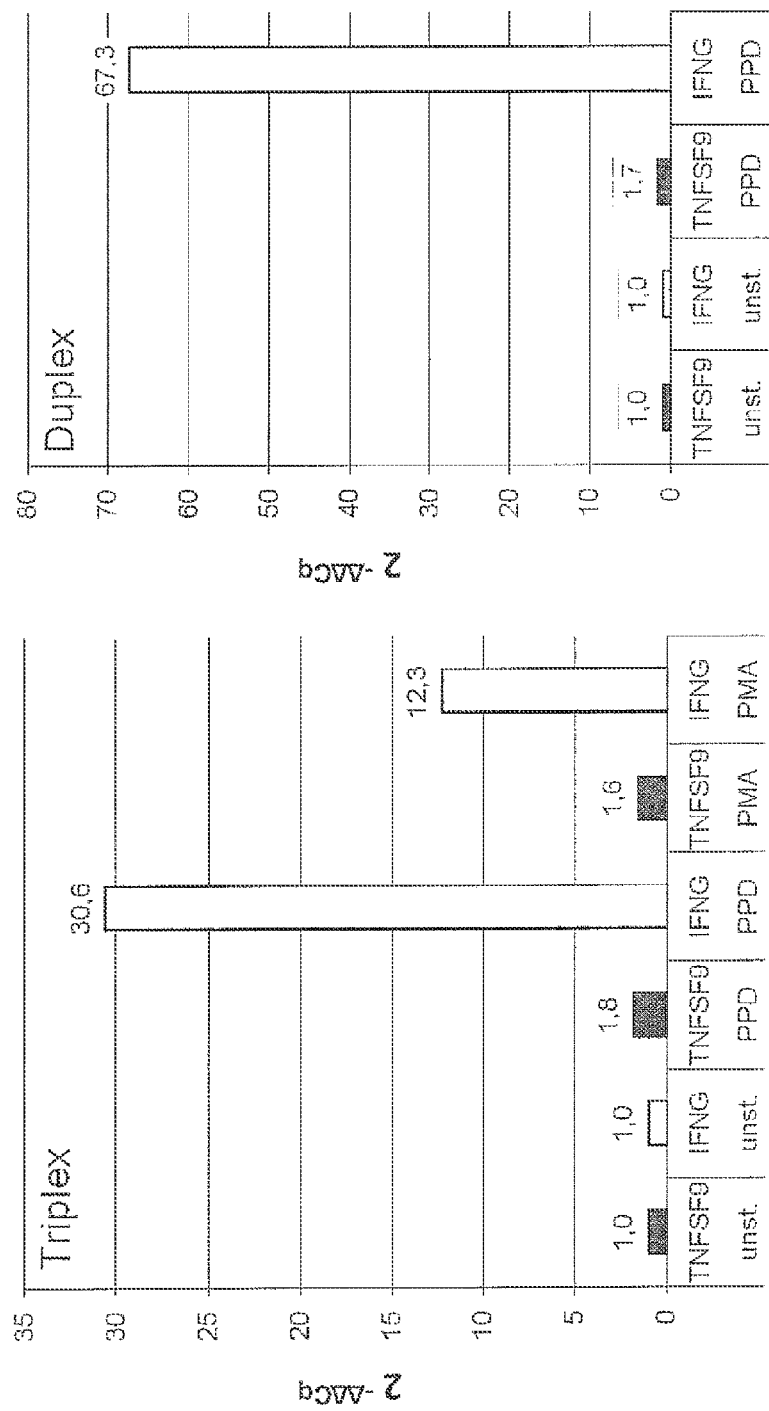
FIG. 18 shows the results for the simultaneous detection of the relative increases in expression of TNFSF9 and IFNG with normalization against TAF1A as reference gene in a triplex qPCR sample (left) in comparison to the respective duplex reactions (right). Unst.: non-stimulated; PPD: tuberculin PPD; PMA: phorbol-12-myristate-13-acetate/ionomycin.

Synchronous Detection of Two RTT Marker Genes with Simultaneous Normalisation Against a Reference Gene by Using a Triplex qPCR For simplification and improvement of the practicability as well as for the extension of the range of application of the inventive RTT method a triplex RT-qPCR was developed, which allows to detect simultaneously in one reaction sample the RTT marker 4-1BBL—also termed TNFSF9—and the marker for the detection of a latent TB infection IFN-γ—also termed IFNG—and allows additionally to normalize the signals by using a reference gene. A sample of a subject with a latent TB was processed according to the inventive method, as described in example 12. The qPCR was done with 1 µl cDNA in 10 µl total reaction volume using TaqMan® Fast Universal PCR Master Mix of Applied Biosystems. The master mix had the following composition: 150 nM TNFSF9 forward primer GAGGGTC-CCGAGCTTTCG (biomers), represented by SEQ ID NO:1; 150 nM TNFSF9 reverse primer GCCCATCGATCAGCA-GAAC (biomers), represented by SEQ ID NO:2; 200 nM TNFSF9 probe FAM-CCACCAGCTGCGCAAACATGC-BBQ (TIB MOLBIOL), represented by SEQ ID NO:3; 300 nM IFNG forward primer GTGGAGACCAT-CAAGGAAGACAT (biomers), represented by SEQ ID NO:7; 300 nM IFNG reverse primer GGCGACAGTTCA-GCCATCA (biomers), represented by SEQ ID NO:8; 200 nM IFNG Sonde BoTMR-TTCATGTATTGCTTTGCGT-TGGACATTCAA-BBQ (TIB MOLBIOL), represented by SEQ ID NO:9; 1× TaqMan® Fast Universal PCR Master Mix, 1×TaqMan® Gene Expression Assay TAF1A VIC dye labelled MGB Probe (primer limited) of Applied Biosystems. The temperature profile of the qPCR comprised 20 s denaturation at 95° C. and then 40 cycles consisting of 3 s at 95° C. and 30 s at 60° C. The qPCR was performed on a StepOnePlus Real-Time PCR system (Applied Biosystems). In FIG. 18 are depicted the results of the comparative $C_q$ analysis ($2^{-\Delta\Delta C_q}$) for one sample of a subject with a latent TB. Given are the results of the triplex (left) and as comparison the results of the respective duplex qPCRs (right). The samples of the duplex qPCR were prepared as described in example 14. These comparative analysis shows, that the detection of RTT markers is in principle possible in a multiplex reaction with simultaneous normalization of the values with a reference gene.

Example 16

Figure 19:
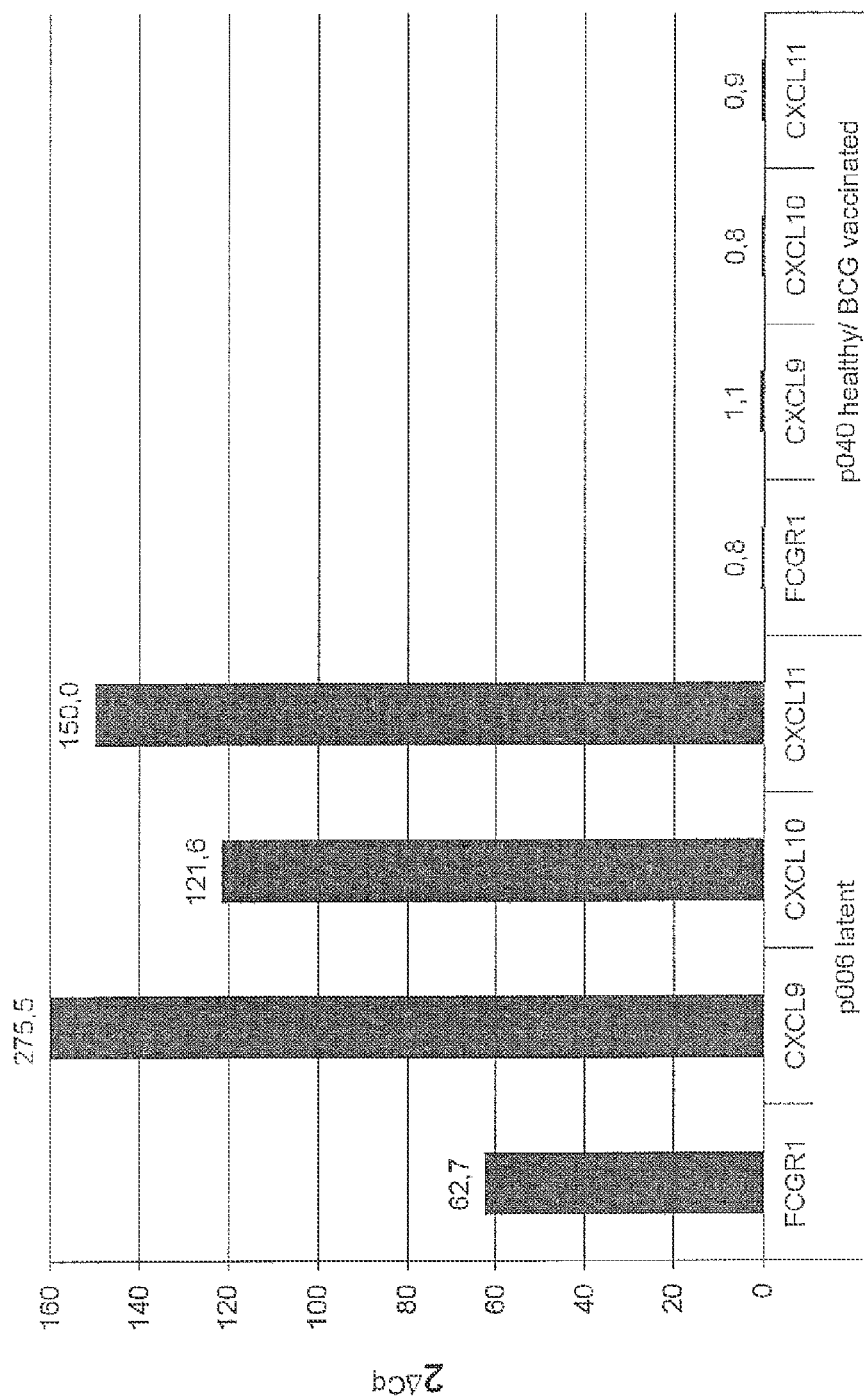
FIG. 19 shows the relative increase in expression of the genes FCGR1ABC, CXCL9, CXCL10, CXCL11 in samples of a healthy volunteer and of a patient with a latent TB after stimulation with tuberculin PPD in comparison to the respective unstimulated samples. The real time qPCR was performed using the SYBR green system. On the x-axis the genes and individuals, respectively, are plotted. The y-axis shows the relative increase in expression ($2^{\Delta Cq}$). BCG: Bacillus Calmette-Guérin, attenuated living vaccine against tuberculosis; CXCL9 to 11: chemokine (C-X-C motif) ligand 9 to 11; FCGR1ABC: Fc gamma receptor 1 A, B, C.

Determination of the Expression of Further Marker Genes for the Inventive RTT Method in Tuberculin PPD Stimulated PBMCs in Comparison to Non-Stimulated Samples of Two Subjects In order to achieve a higher sensitivity of the inventive RTT method, further marker genes were tested in a RT-qPCR with the SYBR Green system. For this purpose in each case a sample of a patient with a latent TB and of a healthy subject were processed according to the inventive method as described in example 12. The qPCR was carried out with 1 µl cDNA in 20 µl total reaction volume using the Brilliant III Ultra-Fast SYBR Green QPCR Master Mix of Agilent Technologies. The master mix had the following composition: 300 nM forward primer, 300 nM reverse primer, 1× Brilliant III Ultra-Fast SYBR Green QPCR Master Mix, 300 nM reference dye. The following primer pairs were used: FCGR1A/B/C forward primer GAAGGGGTGCACCGGAA (TIB MOLBIOL), represented by SEQ ID NO:16; FCGR1A/B/C reverse primer CTCACGGGGAGCAAGTGG (TIB MOLBIOL), represented by SEQ ID NO:17; CXCL9 forward primer GAGTGCAAGGAACCCCAGTAGT, represented by SEQ ID NO:18; CXCL9 reverse primer GGTGGATAGTCCCTTGGTTGGT, represented by SEQ ID NO:19; CXCL10 forward primer TCCACGTGTTGAGATCATTGC, represented by SEQ ID NO:20; CXCL10 reverse primer TCTTGATGGCCTTCGATTCTG, represented by SEQ ID NO:21; CXCL11 forward primer CAAGGCTTCCCCATGTTCA, represented by SEQ ID NO:22; CXCL11 reverse primer CCCAGGGCGTATGCAAAGA, represented by SEQ ID NO:23 (all CXCL primers are from the doctoral thesis of Theresa Knoblach, 2010, Das Cytomegalievirus IE1-Protein als Regulator des humanen Transkriptoms and Zielstruktur RNAi-basierter Therapiestrategien, University of Regensburg). The temperature profile of the qPCR comprised 3 min denaturation at 95° C. and then 40 cycles consisting of 5 s at 95° C. and 10 s at 60° C. The qPCR was performed on a StepOnePlus Real-Time PCR system (Applied Biosystems). The results of the comparative $C_q$ analysis ($2^{\Delta C_q}$) are given for both samples in FIG. 19.

This comparative analysis of stimulated and non-stimulated samples of a latently infected TB patient and a healthy individual, respectively, indicate, that these genes may be suitable as marker for the detection of latent TB diseases.

The invention claimed is:
1. A method for the detection, differentiation and quantification of T cell populations, comprising the following steps:
   a) contacting a first aliquot of a body fluid of an individual with at least one antigen, wherein the body fluid contains antigen presenting cells (APC) and T cells;
   b) incubating the first aliquot with the at least one antigen over a certain period of time;
   c) detecting and differentiating the T cell population by detecting in the first aliquot and in a second aliquot of the body fluid of step a), which has not been incubated with the at least one antigen, at least a first marker of the APC induced by the T cells in a specific T cell population using reverse transcription quantitative real-time polymerase chain reaction (RT-qPCR), and
   d) detecting and quantifying the T cell population by determining the ratio of the detected marker of the APC of the first aliquot to the second aliquot.

2. The method according to claim 1, wherein in step c) additionally at least a second marker is detected in the first and in the second aliquot, wherein the second marker is an induced marker of the T cells themselves, and step d) comprises the detection and quantification of the T cell population by determining the ratio of the detected first marker of the APC and the second marker of the T cell in the first aliquot to the second aliquot.

3. The method according to claim 1, wherein the method comprises in step a) a further step a') contacting the second aliquot with at least one antigen, and comprises in step b) a further step b') incubating the second aliquot for a certain period of time, wherein the period of time in step b') is different from the period of time in step b), and comprises instead of step c) a step c') detection and differentiation of the T cell population by detecting the first marker in the first and second aliquot by RT-qPCR, and comprises step d).

4. The method according to claim 3, wherein step c') comprises the detection and—differentiation of the T cell populations by detecting the first and the second marker.

5. The method according to claim 1, wherein the aliquot of the body fluid is separated into an aliquot A containing only APCs and into an aliquot B containing T cells, and wherein step a) comprises a step a1) contacting the aliquot A with at least one antigen, and a subsequent step a2) contacting the aliquot A contacted with the at least one antigen with aliquot B.

6. The method according to claim 1, wherein the T cell populations contain naive T cells, activated T cells or memory T cells.

7. The method according to claim 1, wherein the T cells of the T cell populations are CD4$^+$ T cells, Th-1 cells, Th-2 cells, Th-17 cells, CD4$^+$CD25$^+$ regulatory T cells, Th-3 cells, CD8$^+$ T cells, CD4$^-$CD8$^+$ cytotoxic T cells, CD4$^-$CD8$^+$ T cells, CD161$^+$ NKT cells and/or a mixture of various T cells.

8. The method according to claim 1, wherein the body fluid is blood, cerebrospinal fluid, lymph, pericardial fluid, a bronchial lavage, a bone marrow aspirate, a suspension of lymphatic tissue or a purified PBMC population.

9. The method according to claim 1, wherein the antigen is a peptide, oligopeptide, a polypeptide, a protein, a RNA or a DNA.

10. The method according to claim 1, wherein the antigen is an antigen of a bacterium, virus, plant, animal, fungi or parasite.

11. The method according to claim 1, wherein the antigen is selected from the group consisting of PSA, HER-2/neu, Mucin-1, MAGE, CEA, myelin basic protein (MBP), myelin oligodendrocytes glycoprotein (MOG), myelin proteolipid protein (PLP), myelin, insulin B, preproinsulin, IA-2, GAD65, Hsp60, ESAT-6, CFP-10, TB7.7, TB37.6, MPT63, tuberculin PPD, VlsE, p58 (BBQ03), p14, p21-24 (OspC), p37-38 (FlaA), p41, p19 (OspE), p18, Crasp3, BB0323, p26 (OspF), p28 (OspD), p30, p39 (BmpA), p60-65 (common antigen, Hsp60), p83-100, p17 (Osp17), p31-32 (OspA), p34 (Osp B), *borrelia* lipids, a lysate of *borrelia* strains, Pr55$^{gag}$, p24, p17, POL, RT, nef, pp65, IE1, IE2, BZLF1, EBNA3, EBNA2, EBNA6, BMLF1, EBNA1, ORF1, ORF4, PRF62, ORF68, HBsAg, HBcAg and AdV5.

12. The method according to claim 1, wherein the period of time for contacting in step a) and incubation in step b) is 0 hours to 72 hours.

13. The method according to claim 1, wherein the first marker of the APC and the second marker of the T cell, respectively, is a nucleic acid or a protein, and is induced by said contacting and incubating with the at least one antigen.

14. The method according to claim 1, wherein the marker of the APC is 4-1BB ligand (4-1BBL), OX40 ligand (OX40L), TNFSF (CD70), B7.1 (CD80), B7.2 (CD86), FcγRIII (CD16), FcγRII (CD32), FcγRI (CD64) or a further representative of the TNF/TNF receptor or immunoglobulin superfamily.

15. The method according to claim 1, wherein the marker of the T cell is INF-β, INF-γ, TNF-α, IL-2, IL-4, IL-5, IL-6, IL-10, IL-12, IL-13, GM-CSF, TGF-β, MIP1a, MIP1b, 4-1BB, CD25, perforin and/or granzyme.

16. The method of claim 12, wherein said time period is 4, 6 or 8 hours.

17. The method of claim 13, wherein the nucleic acid or protein is a RNA, a DNA, a nucleic acid fragment, a peptide or a peptide fragment.

18. The method according to claim 1, wherein the detection and the quantification in step c) and d) is performed additionally by using PCR, quantitative PCR (qPCR), microarray, FACS, ELISpot or ELISA.

* * * * *

SEQUENCE LISTING

<160> NUMBER OF SEQ ID NOS: 23

<210> SEQ ID NO 1
<211> LENGTH: 18
<212> TYPE: DNA
<213> ORGANISM: Artificial Sequence
<220> FEATURE:
<223> OTHER INFORMATION: 4-1BBL Forward Primer

<400> SEQUENCE: 1
gagggtcccg agctttcg                                                 18

<210> SEQ ID NO 2
<211> LENGTH: 19
<212> TYPE: DNA
<213> ORGANISM: Artificial Sequence
<220> FEATURE:
<223> OTHER INFORMATION: 4-1BBL Reverse Primer

<400> SEQUENCE: 2
gcccatcgat cagcagaac                                                19

<210> SEQ ID NO 3
<211> LENGTH: 21
<212> TYPE: DNA
<213> ORGANISM: Artificial Sequence
<220> FEATURE:
<223> OTHER INFORMATION: 4-1BBL Sonde

<400> SEQUENCE: 3
ccaccagctg cgcaaacatg c                                             21

<210> SEQ ID NO 4
<211> LENGTH: 19
<212> TYPE: DNA
<213> ORGANISM: Artificial Sequence

```
<220> FEATURE:
<223> OTHER INFORMATION: GAPDH Forward Primer

<400> SEQUENCE: 4
gaaggtgaag gtcggagtc                                                  19

<210> SEQ ID NO 5
<211> LENGTH: 21
<212> TYPE: DNA
<213> ORGANISM: Artificial Sequence
<220> FEATURE:
<223> OTHER INFORMATION: GAPDH Reverse Primer

<400> SEQUENCE: 5
gtaaaccatg tagttgaggt c                                               21

<210> SEQ ID NO 6
<211> LENGTH: 24
<212> TYPE: DNA
<213> ORGANISM: Artificial Sequence
<220> FEATURE:
<223> OTHER INFORMATION: GAPDH Sonde

<400> SEQUENCE: 6
tcattgatgg caacaatatc cact                                            24

<210> SEQ ID NO 7
<211> LENGTH: 23
<212> TYPE: DNA
<213> ORGANISM: Artificial Sequence
<220> FEATURE:
<223> OTHER INFORMATION: IFNG Forward Primer

<400> SEQUENCE: 7
gtggagacca tcaaggaaga cat                                             23

<210> SEQ ID NO 8
<211> LENGTH: 19
<212> TYPE: DNA
<213> ORGANISM: Artificial Sequence
<220> FEATURE:
<223> OTHER INFORMATION: IFNG Reverse Primer

<400> SEQUENCE: 8
ggcgacagtt cagccatca                                                  19

<210> SEQ ID NO 9
<211> LENGTH: 30
<212> TYPE: DNA
<213> ORGANISM: Artificial Sequence
<220> FEATURE:
<223> OTHER INFORMATION: IFNG Sonde

<400> SEQUENCE: 9
ttcatgtatt gctttgcgtt ggacattcaa                                      30

<210> SEQ ID NO 10
<211> LENGTH: 19
<212> TYPE: DNA
<213> ORGANISM: Artificial Sequence
<220> FEATURE:
<223> OTHER INFORMATION: huP0 Forward Primer

<400> SEQUENCE: 10
gtggtgctga tgggcaaga                                                  19
```

```
<210> SEQ ID NO 11
<211> LENGTH: 21
<212> TYPE: DNA
<213> ORGANISM: Artificial Sequence
<220> FEATURE:
<223> OTHER INFORMATION: huP0 Reverse Primer

<400> SEQUENCE: 11
gcagcagttt ctccagagct g                                              21

<210> SEQ ID NO 12
<211> LENGTH: 22
<212> TYPE: DNA
<213> ORGANISM: Artificial Sequence
<220> FEATURE:
<223> OTHER INFORMATION: huP0 Sonde

<400> SEQUENCE: 12
accatgatgc gcaaggccat cc                                             22

<210> SEQ ID NO 13
<211> LENGTH: 18
<212> TYPE: DNA
<213> ORGANISM: Artificial Sequence
<220> FEATURE:
<223> OTHER INFORMATION: PBGD Forward Primer

<400> SEQUENCE: 13
ccagctccct gcgaagag                                                  18

<210> SEQ ID NO 14
<211> LENGTH: 20
<212> TYPE: DNA
<213> ORGANISM: Artificial Sequence
<220> FEATURE:
<223> OTHER INFORMATION: PBGD Reverse Primer

<400> SEQUENCE: 14
cactgaactc ctgctgctcg                                                20

<210> SEQ ID NO 15
<211> LENGTH: 24
<212> TYPE: DNA
<213> ORGANISM: Artificial Sequence
<220> FEATURE:
<223> OTHER INFORMATION: PBGD Sonde

<400> SEQUENCE: 15
cccagctgca gagaaagttc ccgc                                           24

<210> SEQ ID NO 16
<211> LENGTH: 17
<212> TYPE: DNA
<213> ORGANISM: Artificial Sequence
<220> FEATURE:
<223> OTHER INFORMATION: FCGR1A/B/C Forward Primer

<400> SEQUENCE: 16
gaaggggtgc accggaa                                                   17

<210> SEQ ID NO 17
<211> LENGTH: 18
<212> TYPE: DNA
<213> ORGANISM: Artificial Sequence
<220> FEATURE:
<223> OTHER INFORMATION: FCGR1A/B/C Reverse Primer
```

```
<400> SEQUENCE: 17
ctcacgggga gcaagtgg                                                    18

<210> SEQ ID NO 18
<211> LENGTH: 22
<212> TYPE: DNA
<213> ORGANISM: Artificial Sequence
<220> FEATURE:
<223> OTHER INFORMATION: CXCL9 Forward Primer

<400> SEQUENCE: 18
gagtgcaagg aaccccagta gt                                               22

<210> SEQ ID NO 19
<211> LENGTH: 22
<212> TYPE: DNA
<213> ORGANISM: Artificial Sequence
<220> FEATURE:
<223> OTHER INFORMATION: CXCL9 Reverse Primer

<400> SEQUENCE: 19
ggtggatagt cccttggttg gt                                               22

<210> SEQ ID NO 20
<211> LENGTH: 21
<212> TYPE: DNA
<213> ORGANISM: Artificial Sequence
<220> FEATURE:
<223> OTHER INFORMATION: CXCL10 Forward Primer

<400> SEQUENCE: 20
tccacgtgtt gagatcattg c                                                21

<210> SEQ ID NO 21
<211> LENGTH: 21
<212> TYPE: DNA
<213> ORGANISM: Artificial Sequence
<220> FEATURE:
<223> OTHER INFORMATION: CXCL10 Reverse Primer

<400> SEQUENCE: 21
tcttgatggc cttcgattct g                                                21

<210> SEQ ID NO 22
<211> LENGTH: 19
<212> TYPE: DNA
<213> ORGANISM: Artificial Sequence
<220> FEATURE:
<223> OTHER INFORMATION: CXCL11 Forward Primer

<400> SEQUENCE: 22
caaggcttcc ccatgttca                                                   19

<210> SEQ ID NO 23
<211> LENGTH: 19
<212> TYPE: DNA
<213> ORGANISM: Artificial Sequence
<220> FEATURE:
<223> OTHER INFORMATION: CXCL11 Reverse Primer

<400> SEQUENCE: 23
cccagggcgt atgcaaaga                                                   19
```